United States Patent
Cha et al.

(10) Patent No.: US 9,309,542 B2
(45) Date of Patent: Apr. 12, 2016

(54) **RECOMBINANT *CALDICELLULOSIRUPTOR BESCII* AND METHODS OF USE**

(71) Applicant: UNIVERSITY OF GEORGIA RESEARCH FOUNDATION, INC., Athens, GA (US)

(72) Inventors: Minseok Cha, Athens, GA (US); Janet Westpheling, Bogart, GA (US); Daehwan Chung, Athens, GA (US)

(73) Assignee: University of Georgia Research Foundation, Inc., Athens, GA (US)

( * ) Notice: Subject to any disclaimer, the term of this patent is extended or adjusted under 35 U.S.C. 154(b) by 0 days.

(21) Appl. No.: 13/969,199

(22) Filed: Aug. 16, 2013

(65) Prior Publication Data

US 2014/0120592 A1     May 1, 2014

Related U.S. Application Data

(60) Provisional application No. 61/684,430, filed on Aug. 17, 2012.

(51) Int. Cl.

| | |
|---|---|
| *C12P 7/10* | (2006.01) |
| *C12P 7/54* | (2006.01) |
| *C12P 3/00* | (2006.01) |
| *C12P 7/06* | (2006.01) |
| *C12N 9/04* | (2006.01) |
| *C12N 9/22* | (2006.01) |
| *C12N 15/74* | (2006.01) |

(52) U.S. Cl.
CPC ................. *C12P 7/54* (2013.01); *C12N 9/0006* (2013.01); *C12N 9/22* (2013.01); *C12N 15/74* (2013.01); *C12P 3/00* (2013.01); *C12P 7/065* (2013.01); *C12P 7/10* (2013.01); *C12P 2203/00* (2013.01); *Y02E 50/16* (2013.01); *Y02E 50/17* (2013.01)

(58) Field of Classification Search
USPC .......... 435/252.3, 254.2, 471, 69.1, 140, 161, 435/6.18, 255.1, 166, 200, 252.7, 91.4; 536/23.2
See application file for complete search history.

(56) References Cited

U.S. PATENT DOCUMENTS

| | | |
|---|---|---|
| 5,872,238 A | 2/1999 | Weber et al. |
| 8,278,087 B2 | 10/2012 | Remmereit et al. |
| 8,420,358 B2 | 4/2013 | Claassen et al. |
| 8,420,375 B2 | 4/2013 | Osterhout et al. |
| 8,435,770 B2 | 5/2013 | Hogsett et al. |
| 8,470,566 B2 | 6/2013 | Trawick et al. |
| 8,486,687 B2 | 7/2013 | Atkinson et al. |
| 8,497,128 B2 | 7/2013 | VanKranenburg et al. |
| 2012/0252072 A1 | 10/2012 | Westpheling et al. |

OTHER PUBLICATIONS

Hamilton-Brehm et al (*Caldicellulosiruptor obsidiansis* sp. nov., an Anaerobic, Extremely Thermophilic, Cellulolytic Bacterium Isolated from Obsidian Pool, Yellowstone National Park Applied and Environmental Microbiology, Feb. 2010, p. 1014-1020 (first available on line on Dec. 2009)).*

F.A. Rainey Description of *Caldicellulosiruptor saccharolyticus* gen. nov., sp. nov: An obligately anaerobic, extremely thermophilic, cellulolytic bacterium. FEMS Microbiology Letters 120 (1994) 263-266.*

ATCC 27405 American Type Culture Collection. ATTC No. 27405 *Clostridium thermocellum*. Nucleic Acid Product Sheet. 2 pages.

Benson et al. "Gen Bank" 2011. vol. 39, Database Issue. D32-D37. *Nucleic Acids Research*. 6 pages.

Blumer-Schuette et al. "*Caldicellulosiruptor* core and pangenomes reveal determinants for noncellulosomal thermophilic deconstriation of plant biomass". 2012. J. Bacteriol. 194(15):4015-4028.

Brown et al. Mutant alcohol dehydrogenase leads to improved ethanol tolerance in *Clostridium thermocellum*. 2011. Proc. Natl. Acad. Sci. USA. 108(33):13752-13757.

Chung et al. "Methylation by a Unique a-class Nr-Cytosine Methyltransferase Is Required for DNA Transformation of Caldicellulosiruptor bescii DSM6725" PLo One. 2012 7:e43844. 9 pages.

Chung et al. "Construction of a Stable Replicating Shuttle Vector for *Caldicellulosiruptor* Species: Use for Extending Genetic Methodologies to Other Members of This Genus". 2013. PLoS One. 8(5):e62881. 10 pages.

Chung et al. "Identification and characterization of Cbel, a novel thermostable restriction enzyme from *Caldicellulosiruptor bescii* DSM 6725 and a member of a new subfamily of HaeIII-like enzymes". Journal of Industrial Microbiology & Biotechnology. 2011. 38:1867-1877.

Chung et al. "Overcoming restriction as a barrier to DNA transformation in *Caldicellulosiruptor* species results in efficient marker replacement" 2013. *Biotech. Biofuels*. 6:82. 9 pages.

Chung et al. "Detection of a novel active transposable element in *Caldicellulosiruptor hydrothermalis* and a new search for elements in this genus" 2013. *J. Ind. Microbiol. Biotechnol*: 40:517-521.

Clausen et al. "Cloning, sequencing, and sequence analysis of two novel plasmids from the thermophilic anaerobic bacterium *Anaerocellum thermophilum*" 2004. *Plasmid*. 52:131-138.

Dam et al. "Insights into plant biomass conversion from the genome of the anaerobic thermophilic bacterium *Caldicellulosiruptor bescii* DSM 6725" 2011. *Nucleic Acids Res*. 39(8):3240-3254.

(Continued)

*Primary Examiner* — Kagnew H Gebreyesus
(74) *Attorney, Agent, or Firm* — Mueting, Raasch & Gebhardt, P.A.

(57) ABSTRACT

This disclosure describes recombinant *Caldicellulosiruptor bescii* microbes designed to produce greater amounts of acetate, $H_2$, and/or ethanol than a comparable wild type control. this disclosure also describes methods that generally include growing such recombinant microbes under conditions effective for the recombinant microbes to produce acetate, $H_2$, and/or ethanol.

11 Claims, 22 Drawing Sheets

(56) References Cited

OTHER PUBLICATIONS de Vrije et al. "Glycolytic pathway and hydrogen yield studies of the extreme thermophile *Caldicellulosiruptor saccharolyticus*" 2007. *Appl. Microbiol. Biotechnol.* 74:1358-1367.

Donahue et al. "Overcoming the restriction barrier to plasmid transformation of *Helicobacter pylori*" 2000. *Molecular Microbiology*. 37(5):1066-1074.

Espinosa et al. "Plasmid rolling circle replication and its control" 1995. *FEMS Microbiol Lett.* 130:111-120.

Farkas et al. "Improved growth media and culture techniques for genetic analysis and assessment of biomass utilization by *Caldicellulosiruptor bescii*" 2013. *Journ. Of Industrial Microbiology & Biotechnology.* 40:41-49.

Grogan. "Cytosine Methylation by the SuaI Restriction-Modification System: Implications for Genetic Fidelity in a Hyperthermophilic Archaeon". *Journal of Bacteriology.* 2003. 185:4657-4661.

Hamilton-Brehm et al. "*Caldicellulosiruptor obsidiansis* sp. Nov., an Anaerobic, Extremely Thermophilic, Cellulolytic Bacterium Isolated from Obsidian Pool, Yellowstone National Park". 2010. *Applied and Environmental Microbiology*. 76(4):1014-1020.

Himmel et al. "Biomass recalcitrance: engineering plants and enzymes for biofuels production". 2007. *Science*. 315:804-807.

Lipscomb et al. "Natural competence in the hyperthermophilic archaeon *Pyrococcus furiosus* facilitates genetic manipulation: construction of markerless deletions of genes encoding the two cytoplasmic hydro genases". 2011. *Appl. Environ. Microbiol.* 77(7):2232-2238.

McCann et al. "Designing the deconstruction of plant cell walls". 2008. *Current Opinion in Plant Biology*. 11:314-320.

Roberts et al. "REBASE—a database for DNA restriction and modification: enzymes, genes and genomes". *Nucleic Acids Research*. 2010. 38:D234-236.

Sambrook. Molecular Cloning: A Laboratory Manual. Cold Spring Harbor Laboratory Press. 2001. Title Page, Copyright Page, Table of Contents.

Svetlichnyi et al. "*Anaerocellum thermophilum* Gen. Nov> Sp. Nov.: An Extremely Thermophilic Celluloytic Eubacterium Isolated from Hot Springs in the Valley of Geysers" *Microbiol.* 1990. 59:598-604.

Wilson. "Three microbial strategies for plant cell wall degradation". 2008. *Annals of the New York Academy of Sciences*. 1125:289-297.

Yang et al. "Efficient degradation of lignocellulosic plant biomass, without pretreatment, by the thermohilic anaerobe *Anaerocellum thermophilum*". 2009. DSM 6725. Applied and Environmental Microbiology. 75(14):4762-4769.

* cited by examiner

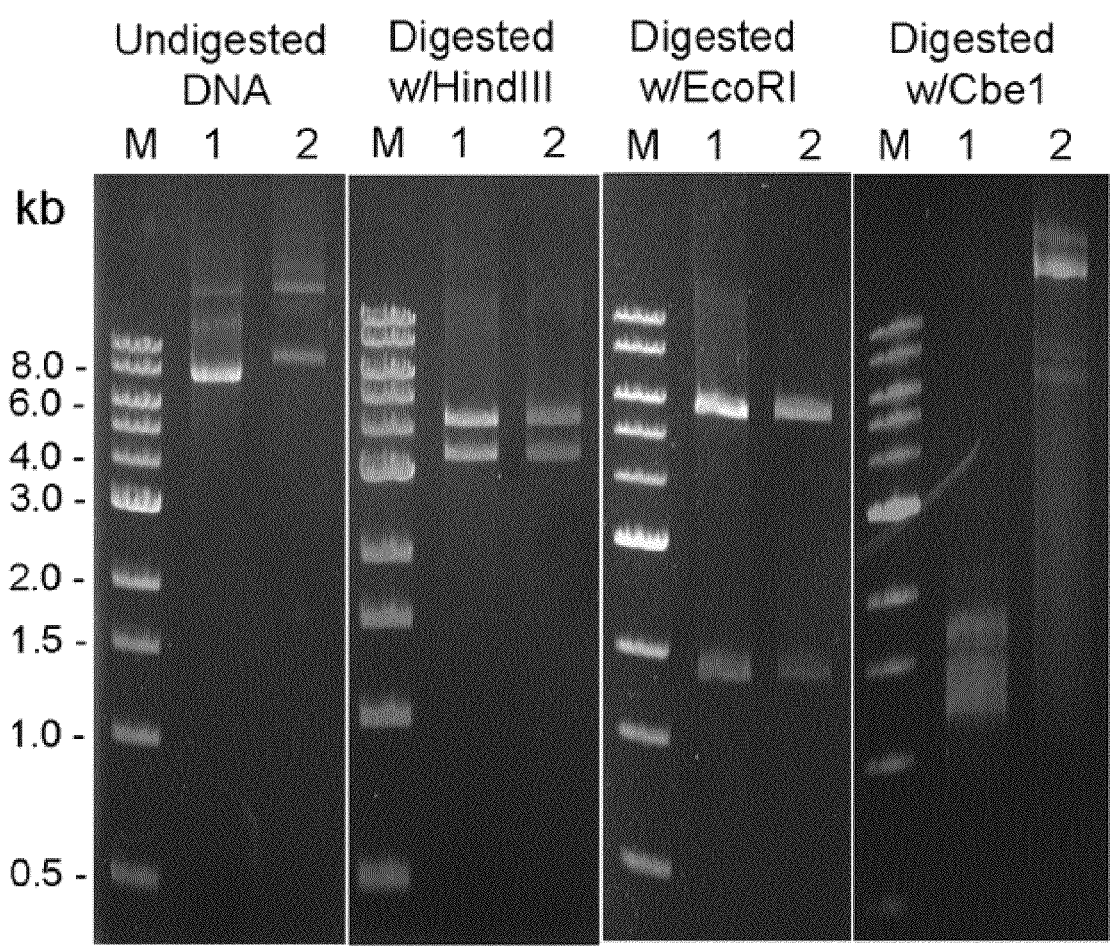

RECOMBINANT *CALDICELLULOSIRUPTOR BESCII* AND METHODS OF USE

CROSS-REFERENCE TO RELATED APPLICATION

This application claims priority to U.S. Provisional Patent Application No. 61/684,430, filed Aug. 17, 2012, which is incorporated herein by reference.

GOVERNMENT FUNDING

This invention was made with government support under DE-AC05-00OR-22725 awarded by the DOE/BioEnergy Science Center (BESC). The government has certain rights in the invention.

SEQUENCE LISTING

This application contains a Sequence Listing submitted electronically via EFS-Web to the United States Patent and Trademark Office as an ASCII text filed entitled "235-02120101_SequenceListing_ST25.txt" having a size of 15 kilobytes and created on Jan. 3, 2014. The information contained in the Sequence Listing is incorporated by reference herein.

SUMMARY

This disclosure describes, in one aspect, a recombinant *Caldicellulosiruptor bescii* that produces a greater amount of acetate than a comparable wild type control.

In another aspect, this disclosure describes a recombinant *Caldicellulosiruptor bescii* that produces a greater amount of $H_2$ than a comparable wild type control.

In another aspect, this disclosure describes a recombinant *Caldicellulosiruptor bescii* that produces a greater amount of ethanol than a comparable wild type control.

In some embodiments of each aspect, the recombinant *Caldicellulosiruptor bescii* produces lactate in an amount less than a comparable wild type control. In some of these embodiments, the recombinant *Caldicellulosiruptor bescii* can include a deletion of at least a portion of a lactate dehydrogenase coding region. In certain embodiments, the recombinant *Caldicellulosiruptor bescii* can include a deletion of at least a portion of Cbes_1918.

In another aspect, this disclosure describes a method that generally includes growing a recombinant *Caldicellulosiruptor bescii* designed to produce acetate in a greater amount than a comparable wild type control, and doing so under conditions effective for the recombinant *Caldicellulosiruptor bescii* to produce acetate. In some embodiments, the method can further collecting at least a portion of the acetate.

In another aspect, this disclosure describes a method that generally includes growing a recombinant *Caldicellulosiruptor bescii* designed to produce $H_2$ in a greater amount than a comparable wild type control, and doing so under conditions effective for the recombinant *Caldicellulosiruptor bescii* to produce $H_2$. In some embodiments, the method can further collecting at least a portion of the $H_2$.

In another aspect, this disclosure describes a method that generally includes growing a recombinant *Caldicellulosiruptor bescii* designed to produce ethanol in a greater amount than a comparable wild type control, and doing so under conditions effective for the recombinant *Caldicellulosiruptor bescii* to produce an alcohol (e.g., ethanol). In some embodiments, the method can further collecting at least a portion of the alcohol.

The above summary of the present invention is not intended to describe each disclosed embodiment or every implementation of the present invention. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

Figure 1:
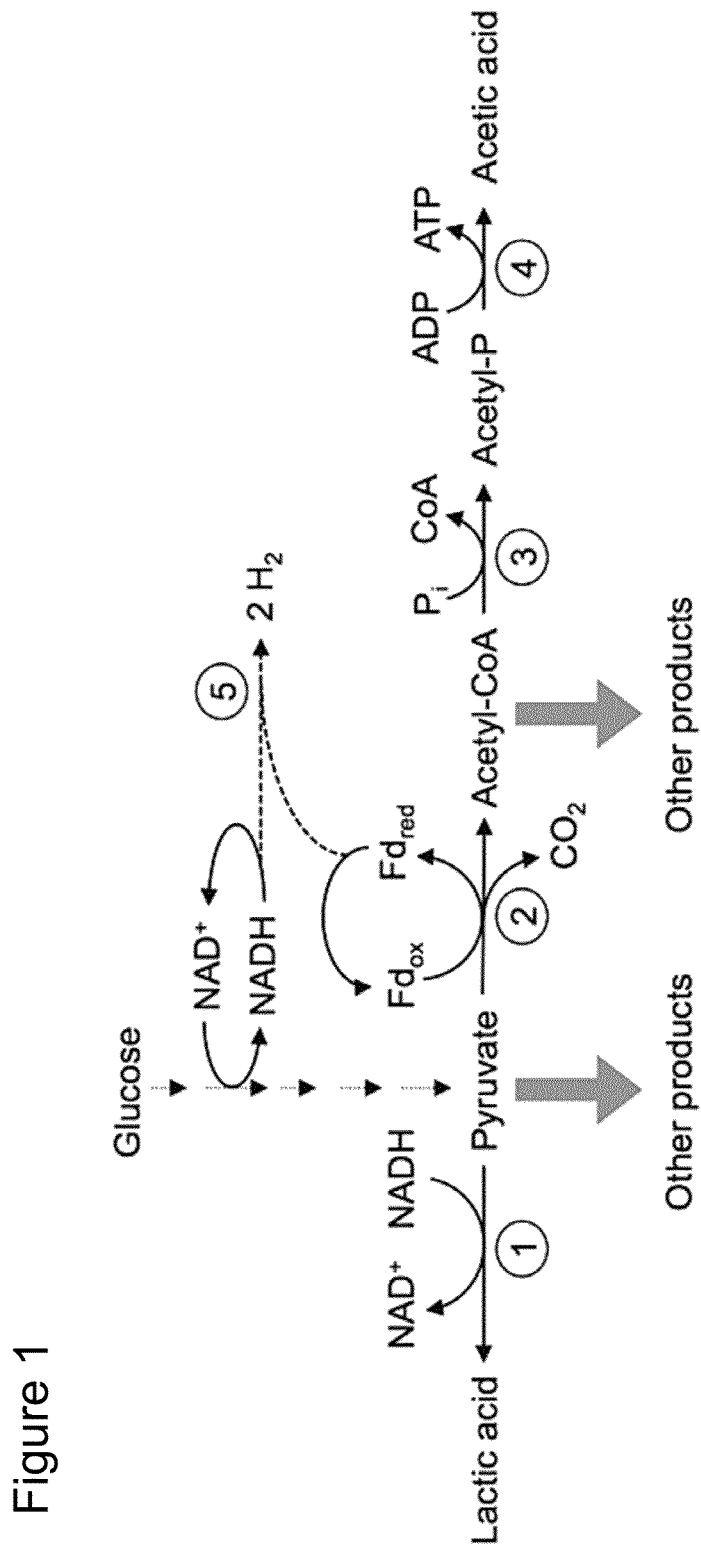
FIG. 1 shows a simplified version of predicted metabolic pathways for fermentation, glycolysis and electron transfer in *Caldicellulosiruptor bescii*. (1) L-Lactate dehydrogenase; (2) Pyruvate-ferredoxin oxidoreductase; (3) Phosphotransacetylase; (4) Acetate kinase; (5) Bifurcating (reduced ferredoxin: NADH-dependent) hydrogenase. The thick grey arrows represent potential heterologous pathways that do not exist in *Caldicellulosiruptor* species but could be used for renewable fuel and chemical production.

This requires a double crossover and results in markerless deletion of the ldh coding region.

FIG. 4 shows the deletion of the ldh coding region in *Caldicellulosiruptor bescii*. (A) A deletion cassette for the ldh coding region was constructed in a non-replicating plasmid that contained a wild type copy of the pyrF coding region, resulting in plasmid pDCW121. The cassette contained ldh 5' and 3' flanking DNA fragments. The plasmid was transformed into JWCB005, and uracil prototrophs were selected (resulting from plasmid insertion). Counter-selection with 5-FOA selected for strains that underwent a second recombination event, resulting in deletion of the marker and ldh to produce strain JWCB017. (B) Agarose gel showing PCR products amplified from the ldh locus in the wild type (lane 2), JWCB005 (ΔpyrFA parent strain, lane 3) and JWCB017 (ΔpyrFA, lane 4). Lane 1: DNA MW standards; Lane 5: no template PCR control. Expected bands: wild type ldh locus—3 kb; ldh deletion—2.0 kb.

FIG. 5 shows fermentation products by *Caldicellulosiruptor bescii* mutant strains. (A) Lactic acid and (B) acetic acid production were measured during growth on 0.5% maltose by the parent strain (JWCB005 ΔpyrFA; filled circles) and JWCB017 (ΔpyrFA Δldh; open circles). (C) Production of lactic and acetic acids by wild type and JWCB017 were further measured by NMR analysis after 48 hours incubation. (D) End products of *C. bescii* wild-type and mutant strains were measured by HPLC on cellobiose after 30 hours incubation, and (E) switchgrass after 120 hours incubation. Acetate, Black; Lactate, Light gray; Hydrogen, Dark gray.

Figure 6A:
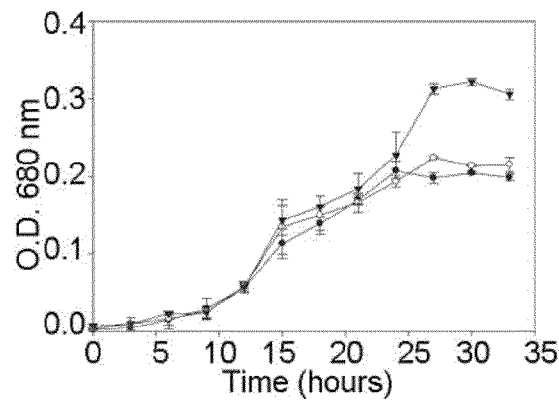
Figure 6B:
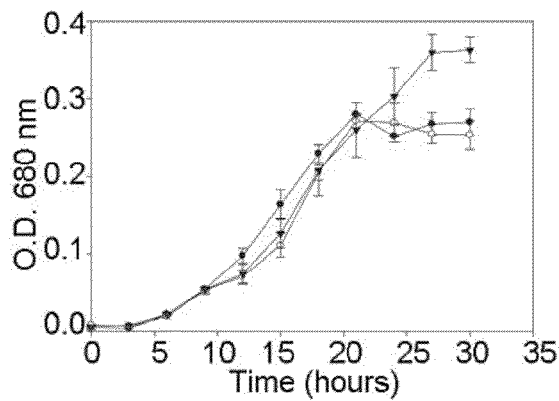

FIG. 6 shows growth (O.D.$_{680\,nm}$) of wild-type and mutant strains on (A) 0.5% of maltose and (B) 0.5% cellobiose as the carbon source; filled circles, Wild-type; open circles, ΔpyrFA (JWCB005); filled triangles, ΔpyrFA Δldh (JWCB017). Error bars based on three biologically independent experiments.

Figure 7A:
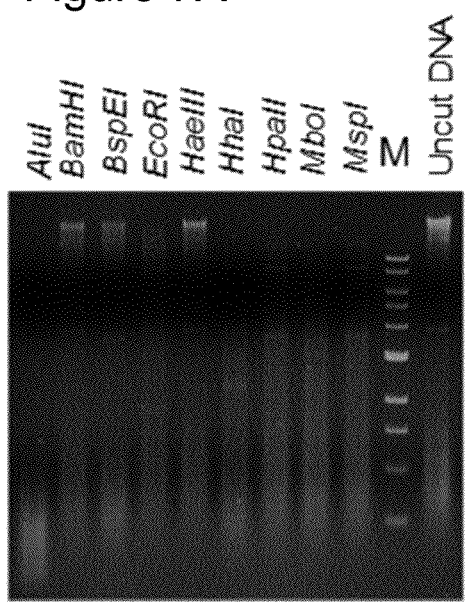
Figure 7B:
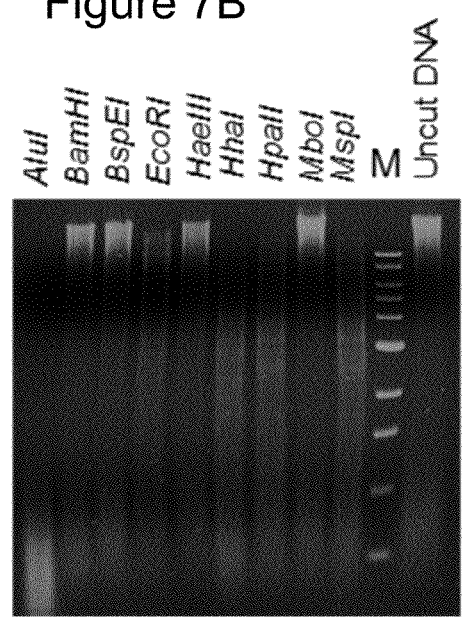

FIG. 7 shows restriction endonuclease digests of chromosomal DNA isolated from *Caldicellulosiruptor* species. The nine restriction enzymes employed in this analysis are indicated on the top of the gel. (A) *C. bescii* chromosomal DNA. (B) *C. saccharolyticus* chromosomal DNA. M: 1 kb DNA ladder (New England Biolabs; Ipswich, Mass.).

FIG. 8 shows a strategy for construction of a cbeI (Cbes2438) and PCR analysis of the cbeI deletion in JWCB005. (A) A diagram of the cbeI genome region is shown with the cbeI knock-out plasmid having ~0.5 kb regions from each up- and downstream of cbeI for homologous recombination and also containing the pyrF cassette (Chung et al., PLoS one, 2013, 8:e62881 (Example 3)) for selection of transformants. Homologous recombination can occur at the upstream or downstream cbeI flanking regions, integrating the plasmid into the genome and generating a strain that is uracil prototroph. Counter-selection with 5-fluoroorotic acid (5-FOA) selects for loss of the plasmid and deletion of the cbeI coding region. Bent arrows depict primers used for verification of the cbeI deletion. (B) Gel depicting PCR products amplified from the cbeI genome region in JWCB018 (ΔpyrFA/ΔcbeI) compared to the parental strain JWCB005 (ΔpyrFA), amplified by primers (DC277 and DC239). Lane 1: JWCB005; lane 2: JWCB018; M: 1 kb DNA ladder (New England Biolabs; Ipswich, Mass.).

Figure 9:
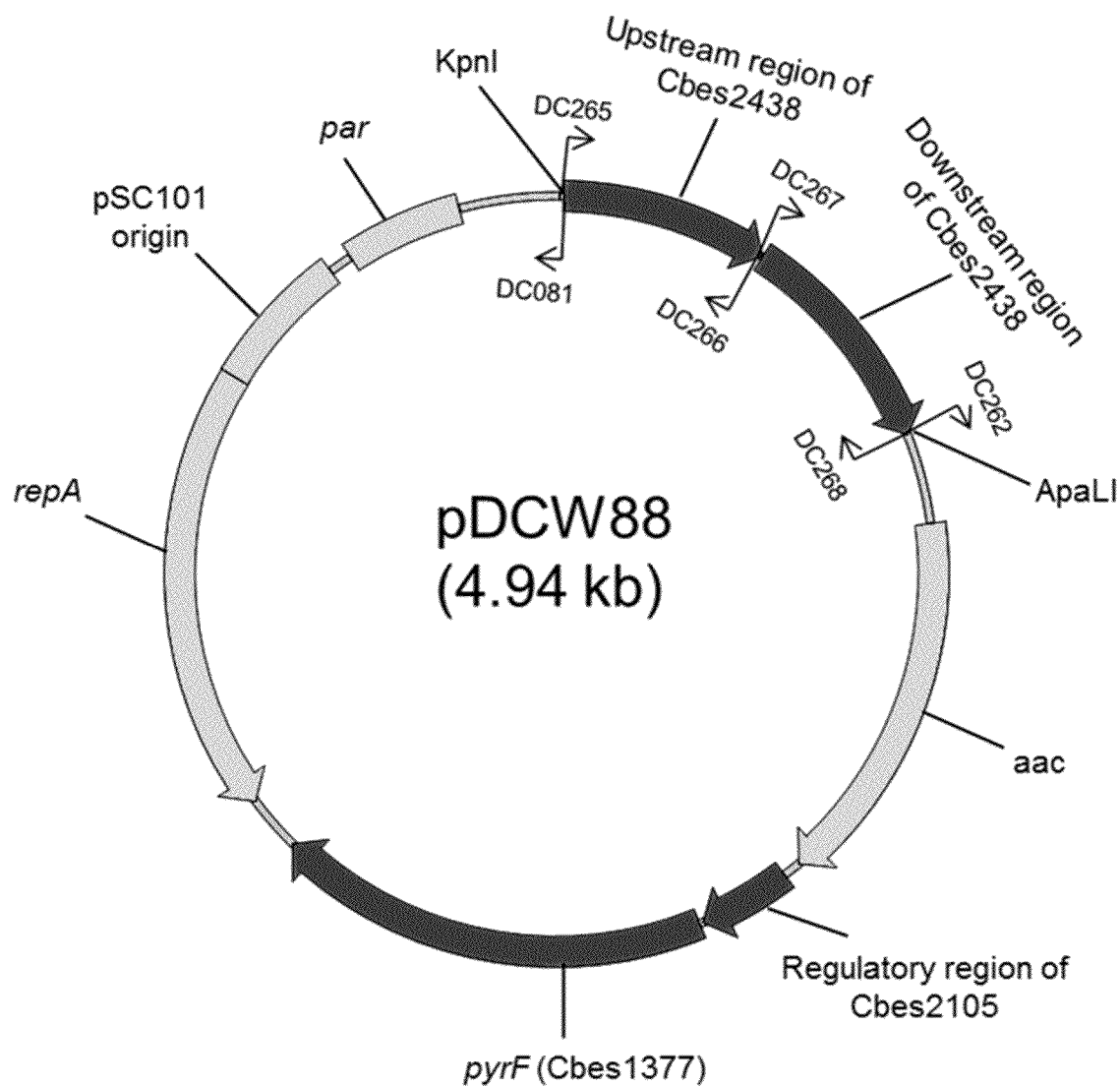

FIG. 9 shows a diagram of the cbeI (Cbes2438) knock-out vector. The gray colored boxes indicate sequences originating from *C. bescii*. Restriction sites and primers are indicated. aac, apramycin resistant cassette; pSC 101, low copy replication origin in *E. coli*; repA and par, plasmid-encoded coding regions required for pSC101 replication and partition.

FIG. 10 shows electrotransformation of unmethylated pDCW89 into JWCB018. (A) JWCB005 (ΔpyrFA) and JWCB018 (ΔpyrFAΔcbeI) were transformed with un-methylated pDCW89 DNA and plated onto defined medium either with or without uracil. Controls with no DNA transformation are also presented. (B) Restriction analysis of pDCW89 plasmid DNA before and after transformation of *C. bescii* and back-transformation to *E. coli*. Lane 1, pDCW89 plasmid DNA isolated from *E. coli* DH5α, digested with either EcoRI (5.8 kb and 1.9 kb cleavage products), or with HindIII (4.4 kb and 3.3 kb cleavage products). Lanes 2, 3 and 4 plasmid DNA isolated from three biologically independent *E. coli* DH5α back-transformants using total DNA isolated from *C. bescii* transformants, digested with either EcoRI or HindIII. M: 1 KB DNA ladder (New England Biolabs; Ipswich, Mass.).

Figures 11A, 11B, 11C:
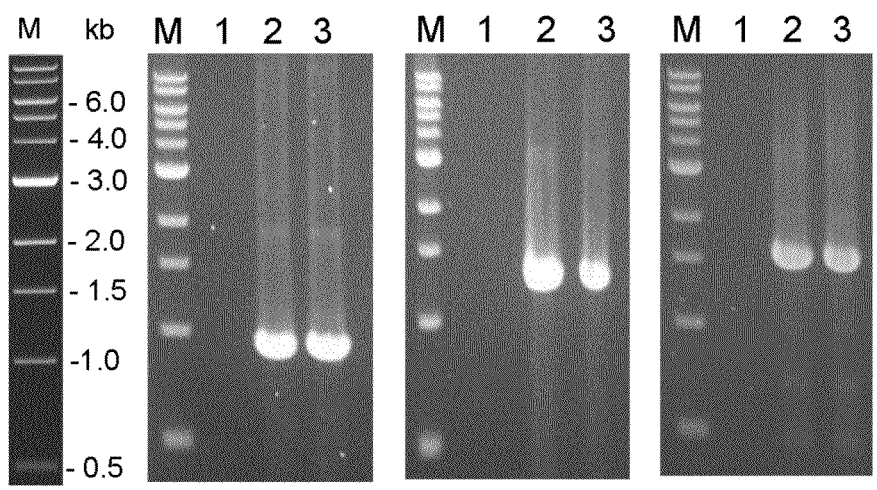

FIG. 11 shows PCR analysis for the presence of pDCW89 after transformation into JWCB005. pDCW89 DNA isolated from *C. hydrothermalis* transformants was used to transform *C. bescii* (ΔpyrFA) and the presence of the plasmid was confirmed by PCR amplification of sequences contained only on the plasmid (A) the 0.9 kb PCR product of aac (Apramycin Resistance cassette), (B) the 1.3 kb PCR product of pyrF cassette and (C) the 1.6 kb PCR product of pSCJ101 ori region. Lane 1: total DNA isolated from JWCB005; lane 2: total DNA isolated from *C. bescii* transformant; lane 3: pDCW 89 isolated from *E. coli*. M: 1 kb DNA ladder (New England Biolabs; Ipswich, Mass.).

FIG. 12 shows a chromosomal map and PCR analysis of the Uridine Monophosphate (UMP) biosynthetic coding region cluster in *C. bescii* DSM 6725 and the spontaneous deletion in pyrFA (JWCB005) locus. (A) A diagram of the pyr operon region with the 878 bp deletion in the pyrFA ORFs. The line below the diagram indicates the length of the deletion. Bent arrows depict primers used for verification of the structure of the chromosome in the JWCB005 (ΔpyrFA) strain. pyrF and pyrE loci indicated as black color filled arrow and black dashed filled arrow, respectively. (B) Gel depicting PCR products of the pyrFA region in wild type (3.44 kb) compared to the ΔpyrFA (2.52 kb) strain amplified by primers (JH020 and FJ298). (C) Gel depicting the 2.66 kb PCR products of pyrE region in wild type and the ΔpyrFA strain by primers (DC326 and DC331). M: 1 KB DNA ladder (New England Biolabs; Ipswich, Mass.).

FIG. 13 shows a plasmid map of shuttle vector (pDCW89) and verification of its presence in *C. bescii* transformants. (A) A linear DNA fragment containing the pyrF expression cassette as well as the entire sequence of pBAS2, generated by PCR amplification using primers DC283 and DC284, was ligated to a DNA fragment containing *E. coli* replication and selection functions to generate the final shuttle vector. The cross-hatched box corresponds to the pBAS2 plasmid sequences. ORFs from *C. bescii* are indicated as empty arrows and those from *E. coli* as black arrows. The apramycin resistant cassette (Apr$^R$); PSC101 low copy replication origin in *E. coli*; repA, a plasmid-encoded required for PSC101 replication; par, partition locus are indicated. The proposed replication origin (115 bp) of pBAS2 is indicated. The primers and restriction sites (AatII and EcoRI) used for the verification are indicated. A detailed description of the construction of pDCW89 is described in FIG. 14 and in Example 3. (B) Gel showing the 1.6 kb PCR products containing the pSC101 ori sequences only presence in pDCW89 using primers DC230 and JF199, total DNA from JWCB005 (Lane 1), a *C. bescii* transformant with pDCW89 (Lane 2), and pDCW89 isolated from *E. coli* (Lane 3) as template. (C) Restriction analysis of plasmid DNA before and after transformation of *C. bescii* and back-transformation to *E. coli*. Lanes 1 and 4, pDCW89 plasmid DNA isolated from *E. coli* DH5α, and digested with AatII (Lane 1, 4.4 kb and 3.3 kb cleavage products), and EcoRI (Lane 4, 1.9 kb and 5.8 kb cleavage products); lane 2, 3, 5, 6, plasmid DNA isolated from two biologically independent *E. coli* DH5α back-transformed from *C. bescii* transformants, and digested with AatII (Lane 2 & 3), and EcoRI (Lane 5 & 6). M: 1 KB DNA ladder (New England Biolabs; Ipswich, Mass.).

Figure 14:
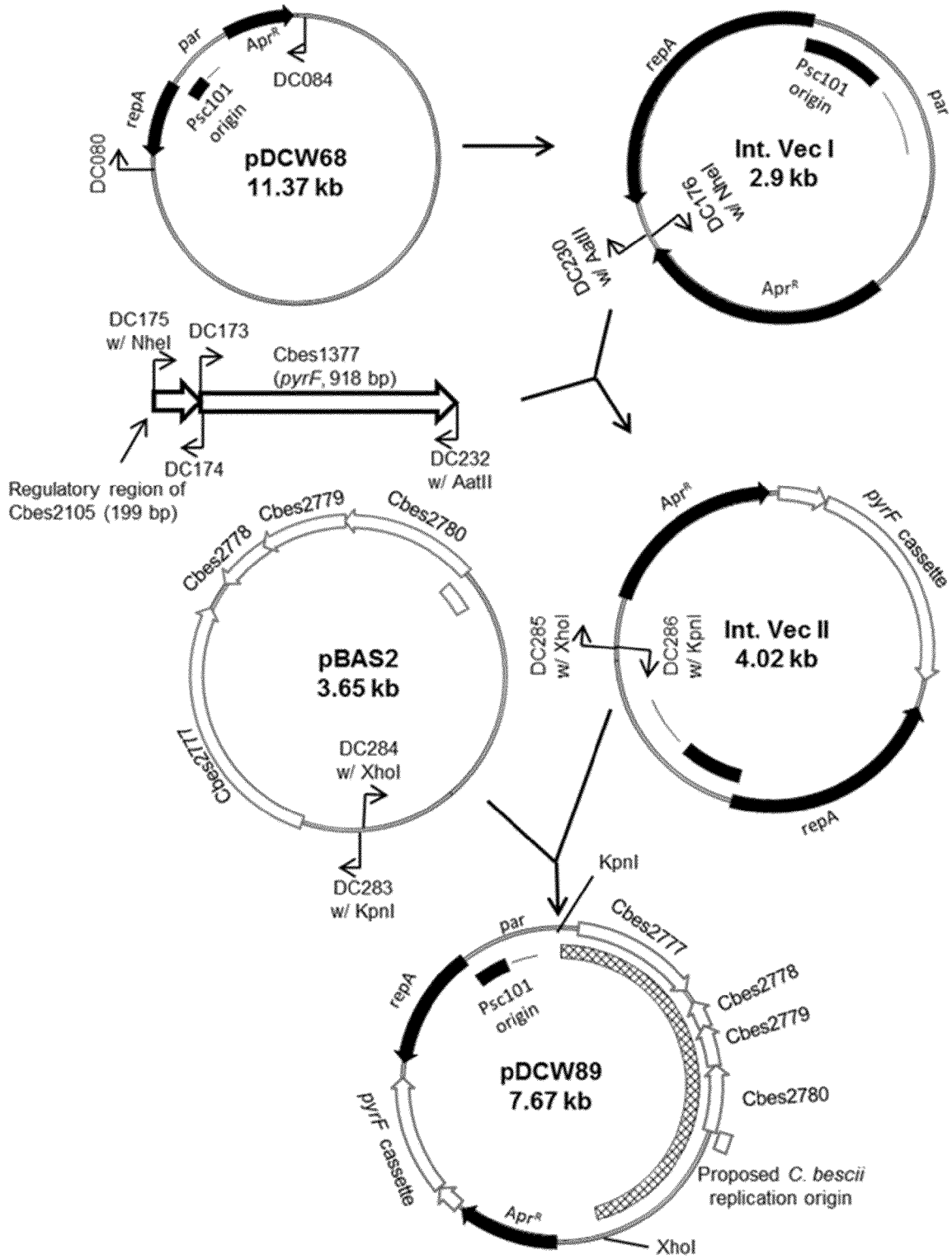

FIG. 14 shows construction of shuttle vector pDCW89. The cross-hatched box corresponds to pBAS2 plasmid sequences. ORFs from *C. bescii* are indicated as empty arrows and those from *E. coli* as black arrows. The apramycin resistant cassette (Apr$^R$); PSC101 low copy replication origin in *E. coli*; repA, a plasmid-encoded coding region required for PSC101 replication; par, partition locus; pyrF cassette are indicated. The proposed replication origin (115 bp) of pBAS2 is indicated. All primers and two restriction sites (KpnI and XhoI) used in this construction are also indicated.

FIG. 15 shows plasmid constructions to determine the minimal sequence requirement for replication in *C. bescii*. DNA sequences derived from *C. bescii* are indicated as empty arrows and boxes. All features in these plasmid DNAs are described in the brief description of FIG. 14. The proposed replication origin (115 bp) of pBAS2 is indicated. All primers and two restriction sites (KpnI and PvuII) used in this construction are also indicated. (A) Diagram of pDCW154. (B) Diagram of pDCW155.

Figure 16A:
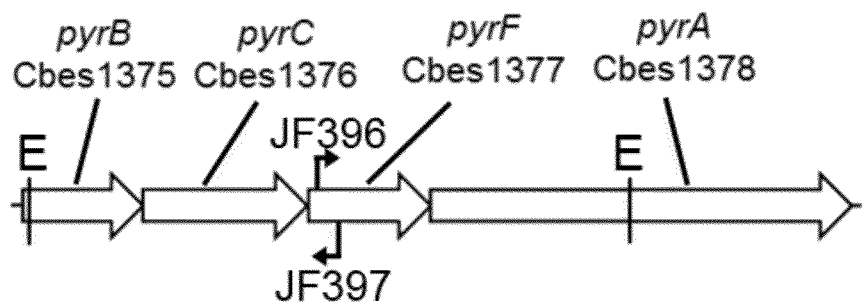
Figure 16B:
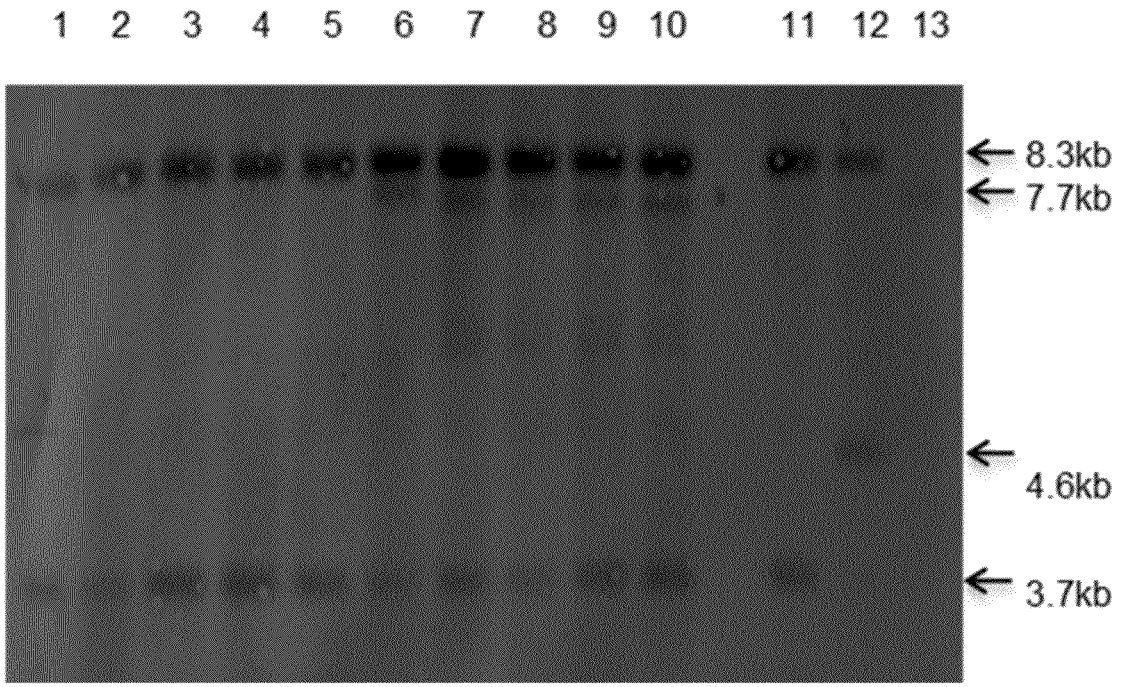

FIG. 16 shows determination of copy number and maintenance of pDCW89 in *C. bescii*. (A) Diagram of the pyrF chromosomal region. EcoRV sites ("E") are indicated, as are the locations of primers used to generate the pyrF hybridization probe. (B) Southern blot of the pDCW89 transformant (JWCB011). Lanes 1 to 5, DNA isolated from 5 successive passages in non-selective medium; lanes 6 to 10, 5 successive passages in selective medium; lane 11, JWCB005; lane 12, *C. bescii* wild type; Lane 13, pDCW89 isolated from *E. coli*.

FIG. 17 shows a comparison of DNA modification status between shuttle vector DNA isolated from *E. coli* (Lane 1) and *C. hydrothermalis* transformants (Lane 2) by Restriction analysis. (A) Undigested, (B) Digested with HindIII (4.3 and 3.4 kb cleavage products); (C) Digested with EcoRI (4.6 and 1.9 kb cleavage products); (D) Digested with CbeI (11 cleavage products are expected). M: 1 KB DNA ladder (New England Biolabs; Ipswich, Mass.).

Figure 18A:
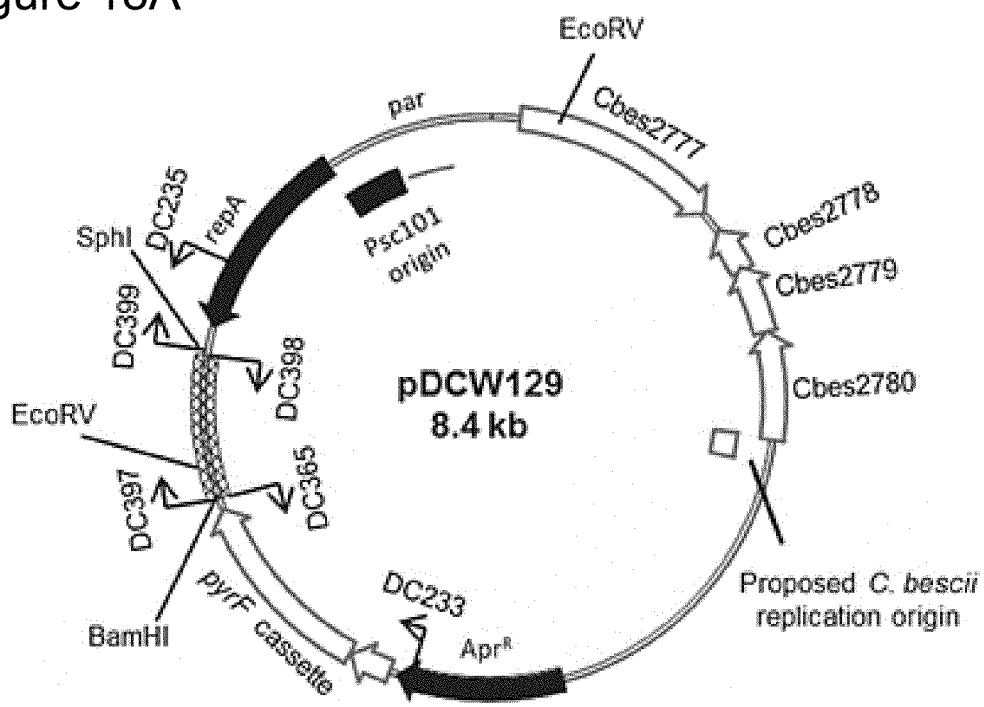

FIG. 18 shows a plasmid map of pDCW129 and verification of its ability to structurally stable maintenance of inserted DNA fragment through transformation and replication in *C. bescii*. (A) Diagram of pDCW129. A linear DNA fragment containing the CBM3 and linker region derived from celA (Cbes1867) was inserted into pDCW89 shuttle vector. The cross-hatched box corresponds to a 0.68 kb of inserted DNA fragment. All features in pDCW129 are indicated in the legend for FIG. 13A. The primers and restriction site (EcoRV) used for the construction and verification are indicated. (B) Gel showing the 2.2 kb DNA fragment containing the pyrF cassette and inserted DNA fragment, amplified by using primers DC233 and DC235. Lane 1, total DNA isolated from JWCB005; lane 2, total DNA isolated from *C. bescii* transformant with pDCW129; lane 3, pCW129 isolated from *E. coli*. (C) EcoRV restriction digestion analysis of plasmid DNA before and after transformation of *C. bescii* and back-transformation to *E. coli*. Lane 1, pDCW129 plasmid DNA isolated from *E. coli* DH5α; lane 2, 3 and 4, plasmid DNA isolated from three biologically independent *E. coli* DH5α back-transformed from *C. bescii* transformants. M: 1 KB DNA ladder (New England Biolabs; Ipswich, Mass.).

Figure 19:
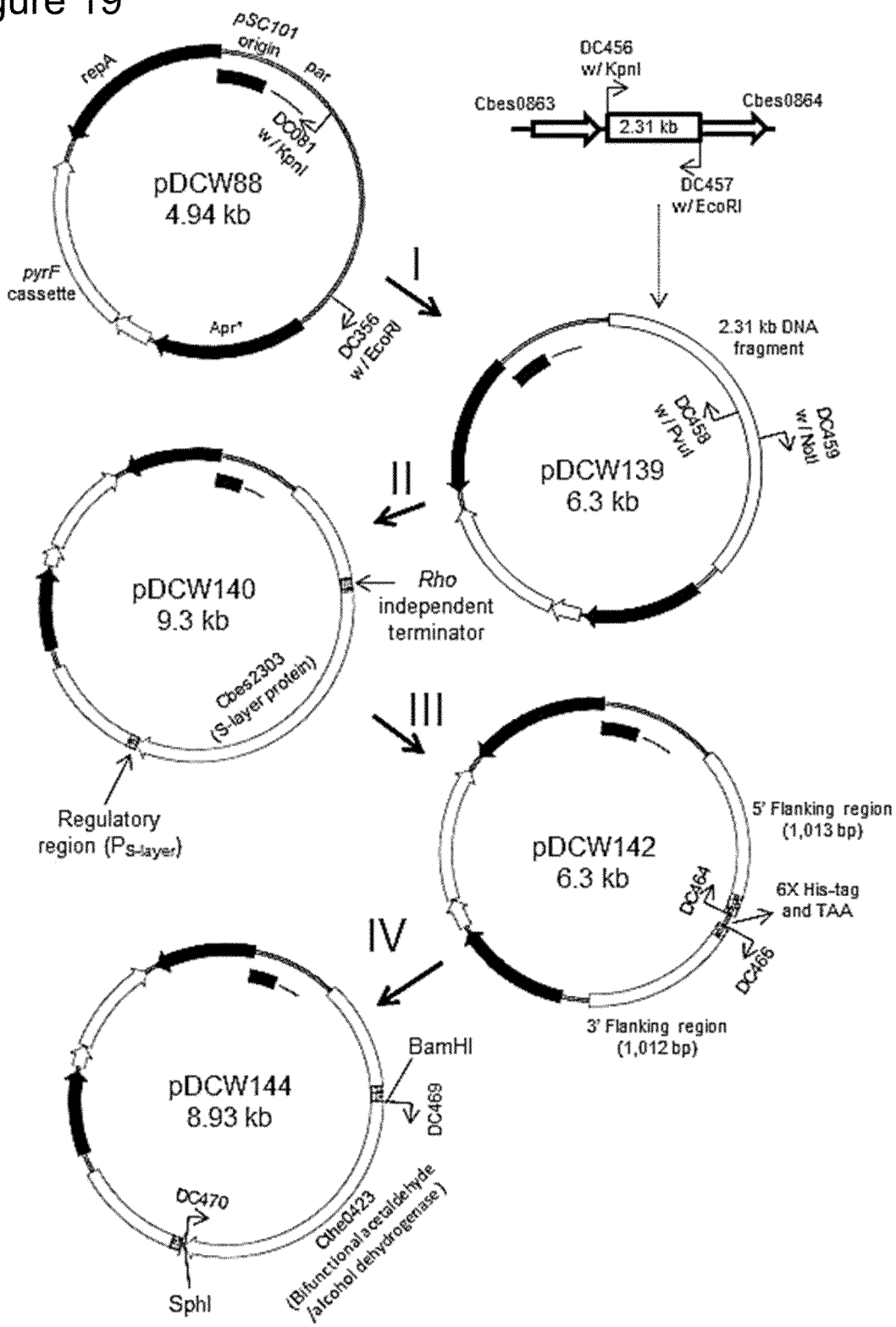

FIG. 19 shows the construction of knock-in vector pDCW144. Plasmid pDCW144 was constructed in four cloning steps. ORFs from *C. bescii* and *Clostridium thermocellum* are indicated as empty arrows. ORFs from *E. coli* indicated as black arrows. The apramycin resistant cassette (Apr$^R$); pSC101, low copy replication origin in *E. coli*; repA, a plasmid-encoded coding region required for pSCJ101 replication; par, partition locus; pyrF cassette; 5' and 3' franking sequences of the targeted insertion site in *C. bescii* chromosome; regulatory and rho independent terminator sequences of Cbes2303 (marked as a cross-hatched box); C-terminal 6× Histidine-tag in front of stop codon are indicated. All primers and two restriction sites (BamHI and SphI) used in this construction are also indicated.

Figure 20A:
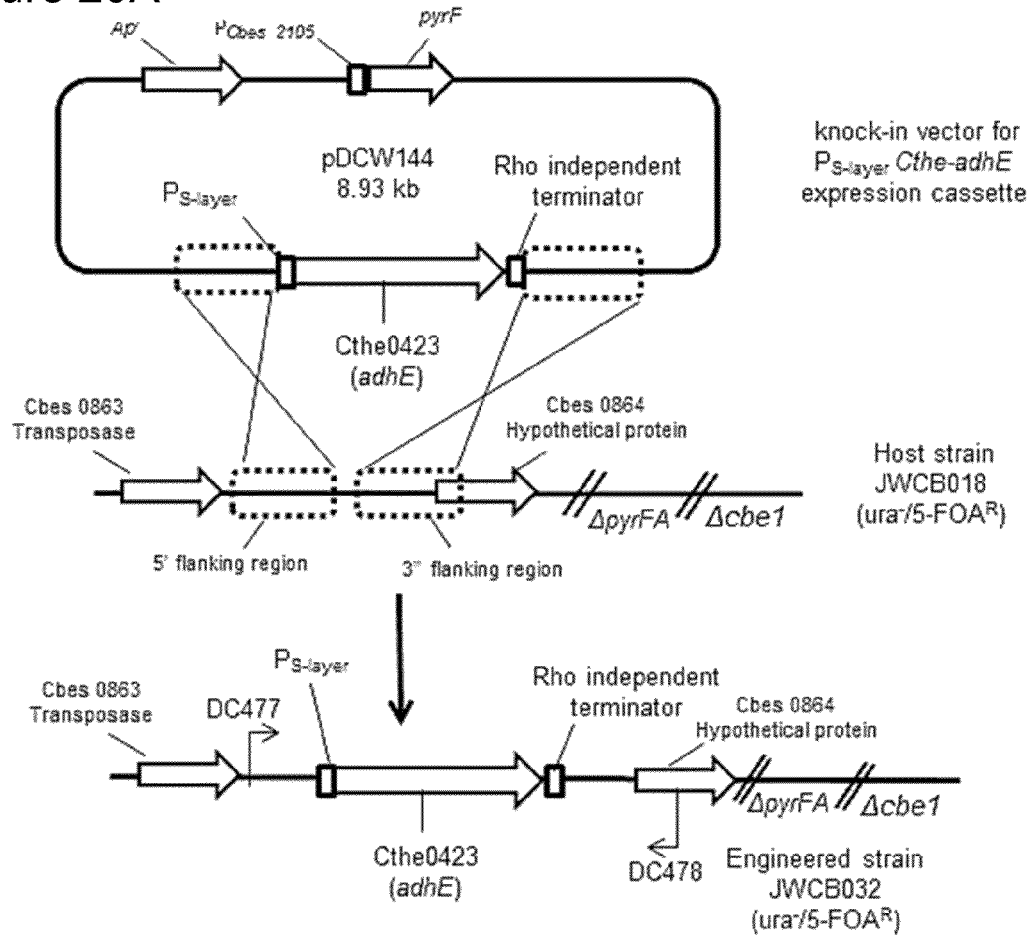

FIG. 20 shows targeted insertion and expression of the *Clostridium thermocellum* ATCC27405 adhE coding region (Cthe0423) in *C. bescii*. (A) A diagram of the targeted knock-in chromosome region is shown with the knock-in plasmid (pDCW144, Fig. S1 for detail description), which contains $P_{S\text{-}layer}$ Cthe-adhE expression cassette and pyrF cassette (Chung et al. (2013) PLoS ONE 8: e62881 (Example 3)) for selection of transformants. pDCW144 is also containing ~1.0 kb regions from each up- and downstream of targeted region for homologous recombination. Homologous recombination can occur at the upstream or downstream targeted chromosome regions, integrating the plasmid into the genome and generating a strain that is a uracil prototroph. Counter-selection with 5-fluoroorotic acid (5-FOA) selects for loss of the plasmid sequences but not the adhE expression cassette. Bent arrows depict primers used for verification of the knock-in of expression cassette (2.6 kb). Ap$^r$ is the apramycin resistance cassette. (B) Gel depicting PCR products amplified from the targeted chromosome region in JWCB032 and JWCB033 compared to the parental strain JWCB018, amplified by primers (DC477 and DC478). Lane 1: JWCB018; lane 2: JWCB032; lane 3: JWCB033; M: 1 kb DNA ladder (New England Biolabs; Ipswich, Mass.). (C) Western blot analysis of *C. bescii* strains used in this study. The 77 μg of total cell protein lysate isolated from the mid-log phase cultures grown at various temperatures either 60° C., 65° C., and 70° C. were electrophoresed and probed with His-tag antibody as described in Material and Methods Lane 1: JWCB018; lane 2: JWCB032; lane 3: JWCB033; M: MagicMark™ XP Western Protein Standard (Invitrogen; Grand Island, N.Y.; Grand Island, N.Y.).

FIG. 21 shows analysis of fermentation products on cellobiose (1%, wt/v) at 65° C. Ethanol (A), acetate (B), and lactate (C). Closed circle, wild type; open square, JWCB018; closed diamond, JWCB032; open triangle, JWCB033. Error bars represent the standard deviation and each point is the average of two biological independent samples.

Figure 22A:
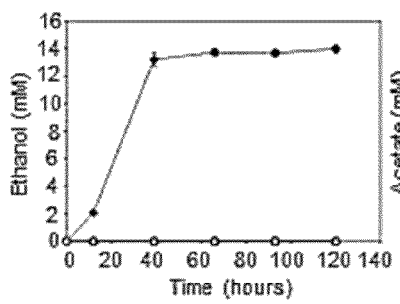
Figure 22B:
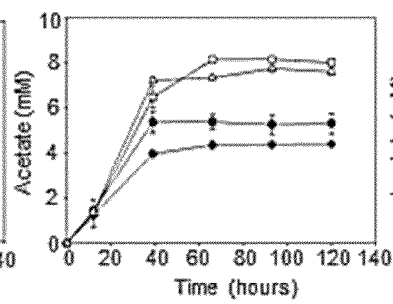
Figure 22C:
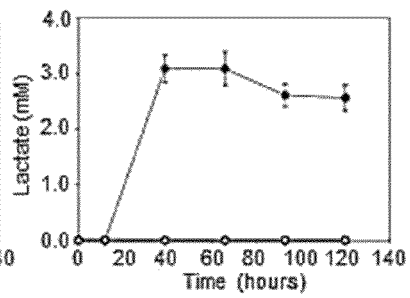

FIG. 22 shows analysis of fermentation products on AVICEL (2%, wt/v) at 65° C. Ethanol (A), acetate (B), and lactate (C). Closed circle, wild type; open square, JWCB018; closed diamond, JWCB032; open triangle, JWCB033. Error bars represent the standard deviation and each point is the average of two biological independent samples.

Figure 23A:
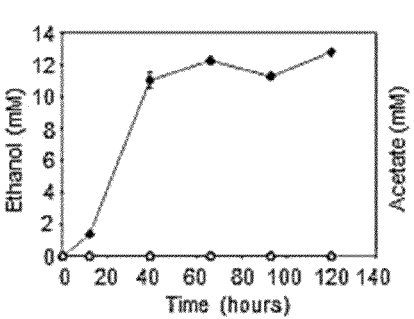
Figure 23B:
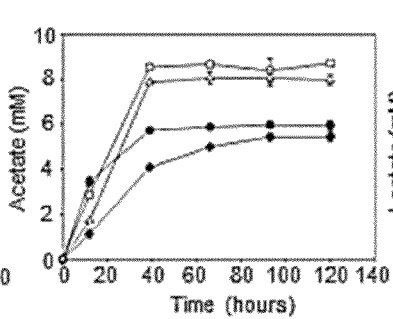
Figure 23C:
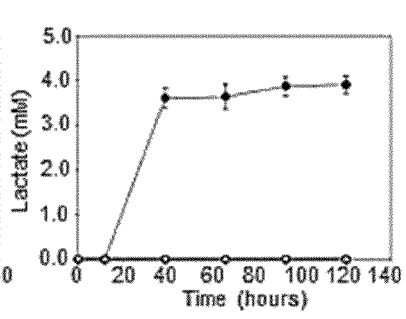

FIG. 23 shows analysis of fermentation products on unpretreated switchgrass (2%, wt/v) at 65° C. Ethanol (A), acetate (B), and lactate (C). Closed circle, wild type; open square, JWCB018; closed diamond, JWCB032; open triangle, JWCB033. Error bars represent the standard deviation and each point is the average of two biological independent samples.

FIG. 24 shows a growth property analysis of wild type and mutant strains. Growth of various *C. bescii* strains on 1.0% of cellobiose as the carbon source at 65° C. (A) and 75° C. (B) was monitored by measuring culture turbidity ($\log_{10}OD_{680nm}$). Error bars represent the standard deviation and each point is the average of two biological independent samples. Closed circles, JWCB001; open triangle JWCB018; open square, JWCB032; closed diamond, JWCB033.

Figure 25A:
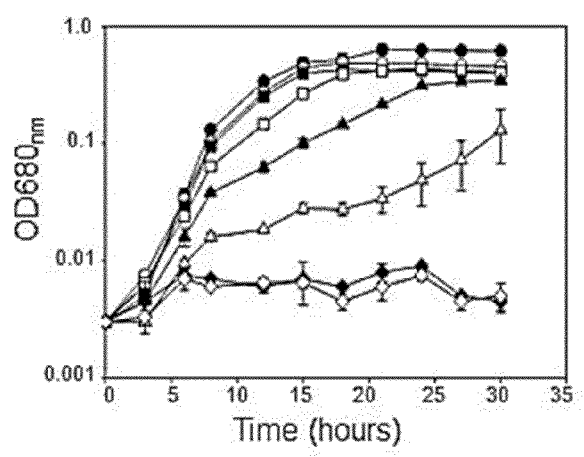
Figure 25B:
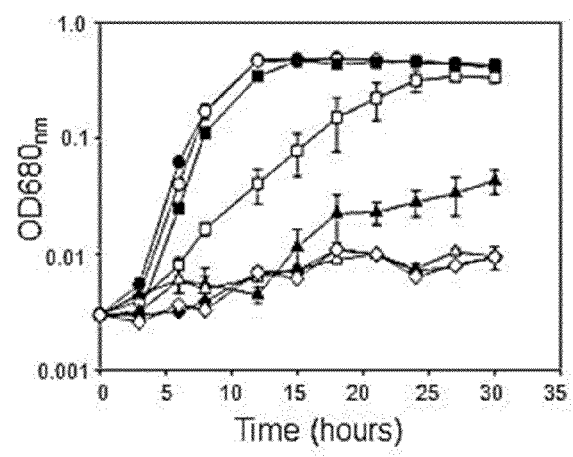

FIG. 25 shows analysis of ethanol tolerance of the *C. bescii* wild-type DSM 6725. Growth of *C. bescii* ori 1.0% of cellobiose as the carbon source supplemented with different amounts of ethanol at 65° C. (A) and 75° C. (B) was monitored by measuring culture turbidity ($\log_{10}OD_{680nm}$). Error bars represent the standard deviation and each point is the average of two biological independent samples. Closed circles, no ethanol; open circle, 200 mM; closed square, 300 mM; open square, 400 mM; closed triangle, 450 mM; open triangle, 500 mM; closed diamond, 600 mM; open diamond, 700 mM. Error bars based on two biologically independent experiments.

DETAILED DESCRIPTION OF ILLUSTRATIVE EMBODIMENTS

*Caldicellulosiruptor* spp. are the most thermophilic and cellulolytic bacteria known and have the ability to degrade unpretreated biomass (4). We recently developed methods for genetic manipulation of members of this genus (U.S. patent application Ser. No. 13/439,069, filed Apr. 4, 2012) and the ability to metabolically engineer these microbes offers the possibility of direct conversion of biomass to biofuels and bioproducts.

Current methods for the use of lignocellulosic biomass as a substrate for microbial conversion to products of interest rely on pretreatment of the biomass with an acids, a base, and/or an organic solvent, often at high temperature and accompanied by treatment with one or more hydrolytic enzymes that partially digest the plant cell walls. Enzymatic pretreatment is particularly expensive and often prohibitive for the production of low value commodity products from biomass.

Thermophilic microorganisms offer special advantages for biomass conversion, in part, because they offer the potential to decrease hydrolysis times by several-fold with the same cellulase loading or to decrease cellulase loading by several-fold at constant hydrolysis times. Organisms that can use complex biomass as substrate reduce the need for pretreatment and enzymatic hydrolysis and, therefore, the cost of the process. *Caldicellulosiruptor* species have the ability to use unpretreated biomass including both low-lignin napier and Bermuda grasses as well as high-lignin switchgrass and a hardwood, popular, for growth. Members of this genus are among the most thermophilic of all known organisms capable of using unpretreated cellulosic biomass.

The sequences of eight *Caldicellulosiruptor* genomes have been published and reveal enzymes likely to be important in lignocellulose utilization. In addition, microarray analysis of cells grown on various substrates implicates specific coding regions and coding region clusters in biomass degradation.
Strategies for Engineering Pyruvate Metabolism in *C. bescii* for Biofuel Production.

FIG. 1 shows a simplified version of native pyruvate metabolic pathways in *C. bescii* based on predictions from genomic analysis of genome sequence. *C. bescii* has been shown to produce lactate, acetate and hydrogen as metabolic products from pyruvate. None of the members of this genus (*Caldicellulosiruptor*) contains a coding region that encodes an acetaldehyde dehydrogenase, an enzyme that can convert acetyl CoA to acetaldehyde, which can subsequently be converted to ethanol by an alcohol dehydrogenase. While there are reports in the literature of some species making trace amounts of ethanol under some conditons, it may be that under special conditions the alcohol dehydrogenase becomes bifunctional allowing trace amounts of ethanol to be produced in the absence of an acetaldehyde dehydrogenase.

We used two strategies for engineering *C. bescii* to produce ethanol and hydrogen. Both strategies use coding regions from *C. thermocellum* because this organism is the best known thermophilic ethanol producer. Coding regions from other bacterial thermophilic strains, like *Thermoanaerobacter* spp., *Geobacillus* spp., etc. also can be cloned and introduced into *C. becii* based on the same strategies.

Figure 2A:
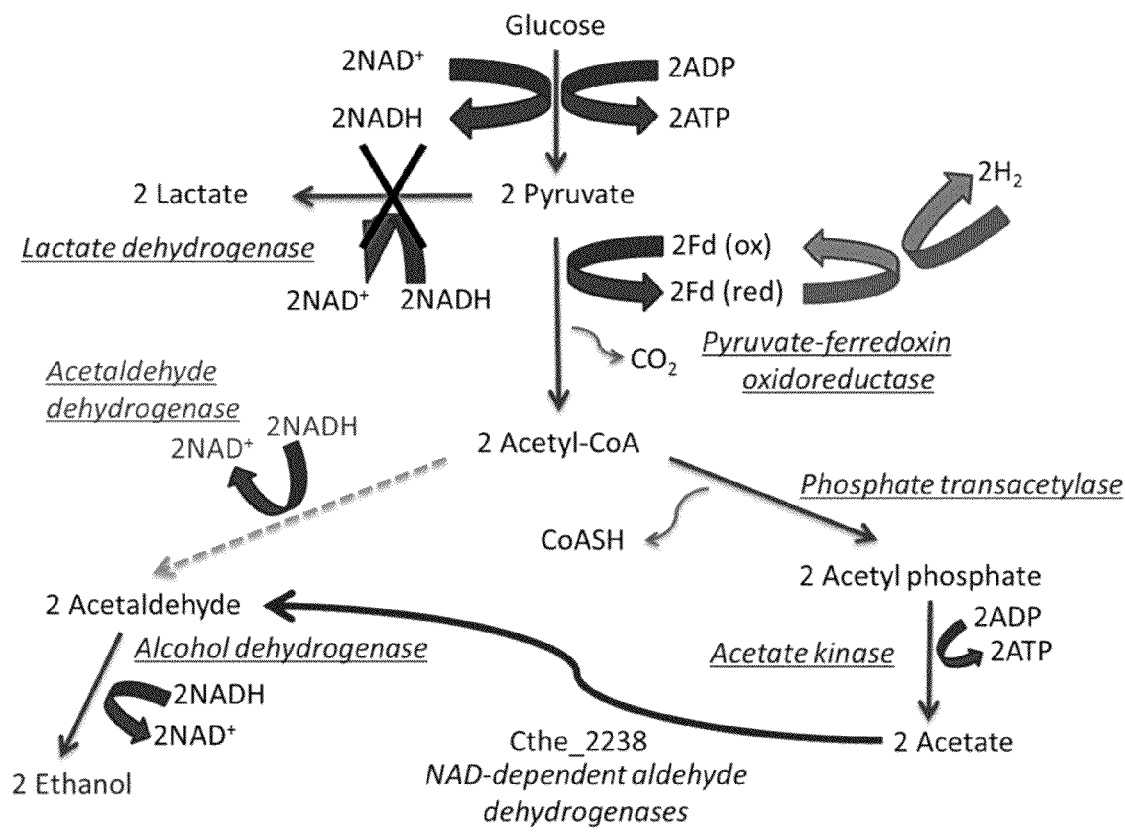
FIG. 2. (A) A modified metabolic pathway for pyruvate metabolism in *Caldicellulosiruptor bescii*. This strategy includes knocking-out the coding region encoding lactate dehydrogenase to produce more acetate and providing a coding region encoding an aldehyde dehydrogenase to convert acetate to acetaldehyde to produce ethanol. (B) An alternative modified metabolic pathway for pyruvate metabolism in *C. bescii*. This strategy includes double knock-out of the coding region encoding lactate dehydrogenase and the coding region encoding acetate kinase, and expressing a coding region encoding acetaldehyde dehydrogenase to covert acetyl-coA to acetaldehyde which is then converted to ethanol by native alcohol dehydrogenase.

Our first strategy involves deleting the coding region that encodes lactate dehydrogenase (FIG. 2A). Based on genomic analysis, there is only one coding region predicted to provide this function in *C. bescii*, Cbes_1918. Thus, in such a mutant, pyruvate should be directed away from the production of lactate and toward the production of Acetyl-CoA and/or hydrogen ($H_2$).

To construct the deletions, we have developed a genetic system that relies on nutritional selection and electrocompetent cells for transformation by electroporation. Nutritional selection is used because antibiotics and drug resistance markers from mesophiles often do not work at the high temperatures used for the growth of these organisms (optimal growth temperature: 75° C.). A random mutation of the pyrF locus was selected on 5-FOA (pyrF converts 5-FOA to a toxic product that kills the cells). Deleting pyrF results in a strain that is a uracil auxotroph resistant to 5-FOA, allowing prototrophic selection and counter selection of the wild type pyrF. Restriction is apparently an absolute barrier to transformation with DNA from *E. coli*, but it can be overcome by methylation with a cognate methylase. The method is efficient enough to allow marker replacement of chromosomal coding regions using non-replicating plasmids.

Figure 3:
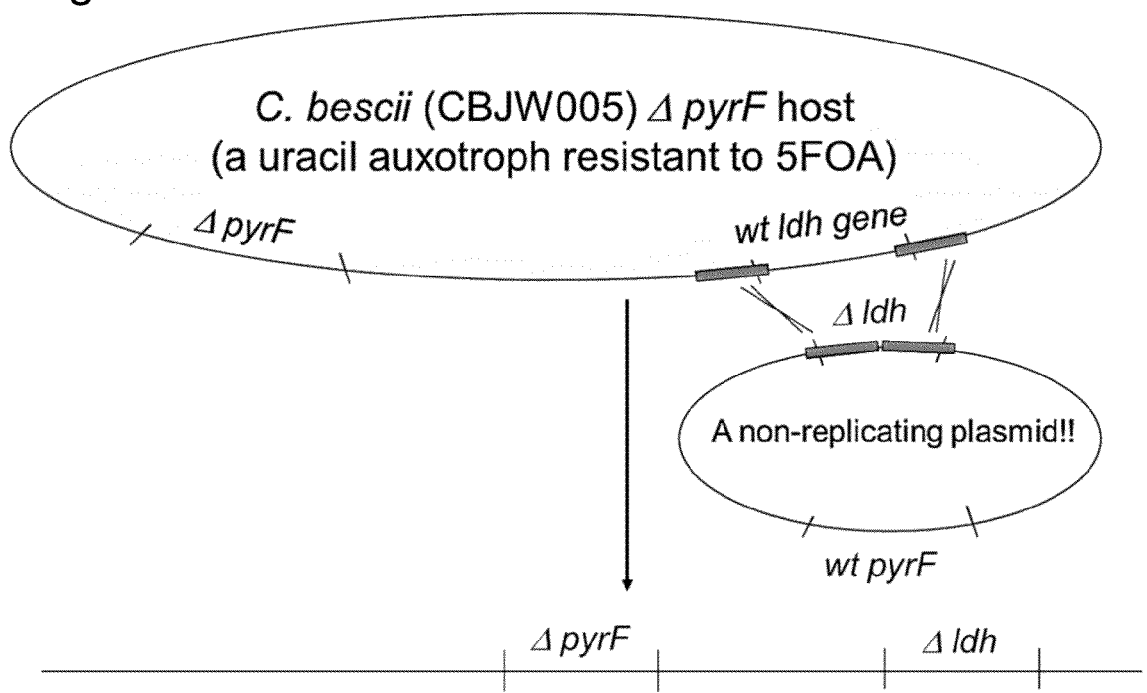
FIG. 3 shows a strategy for the deletion of the ldh coding region in *Caldicellulosiruptor bescii*. Chromosomal DNA of a ΔpyrF *C. bescii*, which is a uracil auxotroph and resistant to 5-FOA, is transformed with methylated plasmid DNA. A knock-out vector was constructed with a WT pyrF coding region and a deletion cassette including the 5' and 3' flanking regions of the ldh coding region. Transformants were first selected for uracil prototrophy and then selected for 5-FOA resistance.

The *C. bescii* host containing a pyrF deletion was used for deletion of the ldh coding region by doing the 5' and 3' flaking regions of ldh and joining them together (FIG. 3). Since the plasmid is non-replicating, prototropy requires integration of plasmid into *C. bescii* chromosome at the ldh locus. Subsequent plating of transformant on 5-FOA selects a second crossover event that eliminates the wild type pyrF allele and plasmid resulting in a deletion of the ldh coding region.

The ΔpyrF Δldh double mutant produces lactate in amounts much less that the wild type control, and makes more actate and hydrogen than the wild type control, in a 2:1 ratio (FIG. 5).

At least a portion of the acetate and/or $H_2$ may be collected using routine, well-known techniques.

The ΔpyrF Δldh double mutant may be further modified by introducing an aldehyde dehydrogenase—e.g., Cthe_2238 from *Clostridium thermocellum*—that converts acetate to acetaldehyde, as shown in FIG. 2A. The acetaldehyde may be subsequently converted to ethanol. Ethanol so produced may be collected using routine, well-known techniques.

Figure 2B:
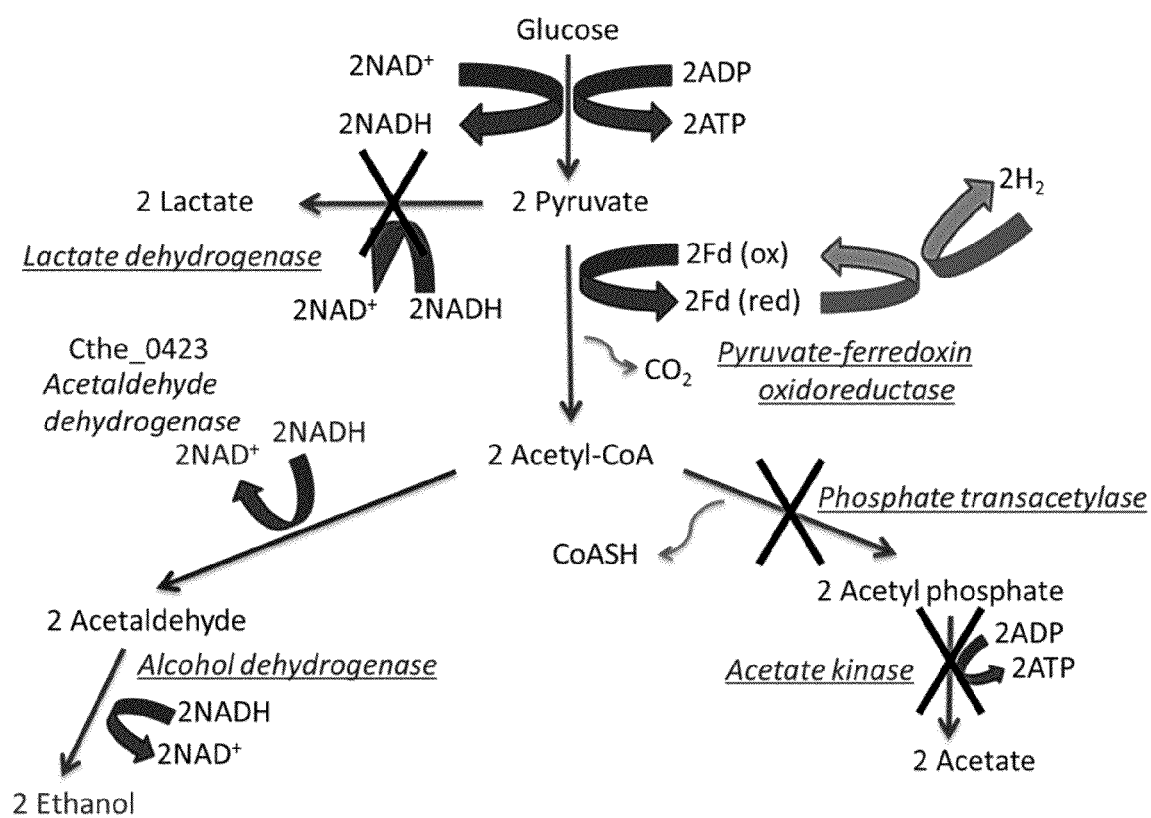

The second strategy involves further modifying the ΔpyrF Δldh double mutant by deleting the coding regions for lactate dehydrogenase phosphate transacetylase (pta) and acetate kinase (ak), respectively (FIG. 2B). The pta and ak coding regions are contiguous on the *C. bescii* chromosome, so this further modification may be accomplished using a single marker replacement to delete both coding regions. In some embodiments, the ΔpyrF Δldh Apta Aak may be further modified by introducing a coding region that encodes an enzyme that converts acetyl-CoA to ethanol such as, for example, Cthe_0423. Ethanol so produced may be collected using routine, well-known techniques.
Deletion of Lactate Dehydrogenase (ldh) from the *C. bescii* Chromosome.

Figure 4B:
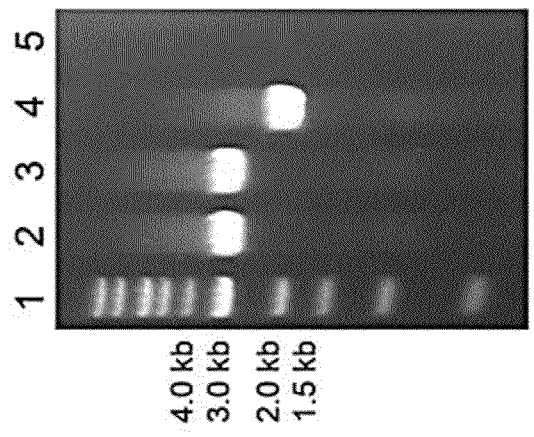
Figure 4A:
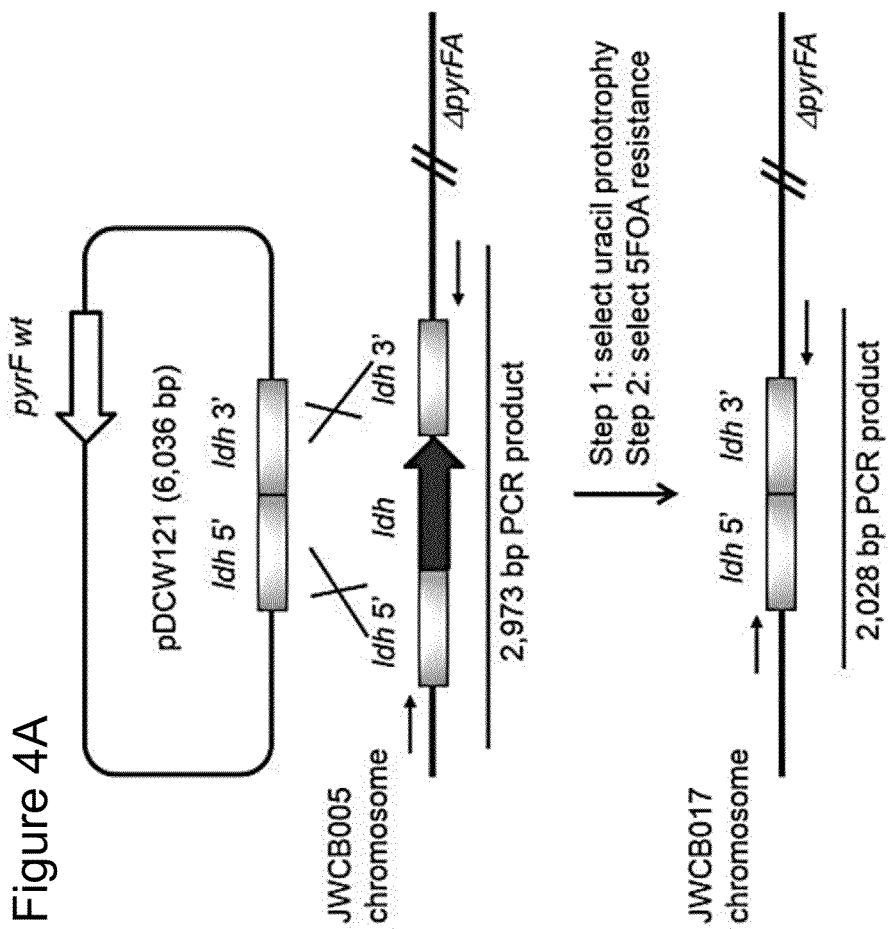

We describe herein a method for DNA transformation and marker replacement in *Caldicellulosiruptor bescii* based on uracil prototrophic selection (Example 2 and Example 3). *C. bescii* strain JWCB005 (ΔpyrFA, ura⁻/5-FGA$^R$, described in more detail below) contains a deletion of the pyrFA locus making the strain a uracil auxotroph resistant to 5-fluoro-orotic acid (5-FOA), allowing the use of pyrF as both a selectable and counter-selectable marker (FIG. 4A). A deletion of the L-lactate dehydrogenase coding region (Cbes1918) was constructed by fusing the 5' and 3' flanking regions of the ldh coding region and cloning the fused product into a non-replicating plasmid vector, resulting in plasmid pDCW121. This vector also contains the wild type pyrF allele under the transcriptional control of a ribosomal protein promoter (Cbes2105, 30S ribosomal protein S30EA), allowing both positive (uracil prototrophy) and negative (5-FOA sensitivity) selection. Plasmid pDCW121 was transformed into *C. bescii* JWCB005 selecting uracil prototrophy resulting from plasmid recombination into the targeted region, followed by counter-selecting 5-FOA resistance (resulting from plasmid excision). The resulting strain, JWCB017, contained a deletion of the ldh wild type coding region in the chromosome. To confirm the ldh deletion in JWCB017, the region of the ldh locus was amplified by PCR using primers outside of the plasmid regions of homology used to construct the deletion (FIG. 4B). The wild type and the ΔpyrFA strain (JWCB005) gave the same 3.0 kb bands, while PCR from JWCB017 resulted in the smaller 2.0 kb band. The PCR product was also sequenced to verify that the deletion in the chromosome was the same as that constructed on the plasmid.

Deletion of ldh Eliminates Lactate Production and Increases Acetate and $H_2$ Production.

Figure 5A:
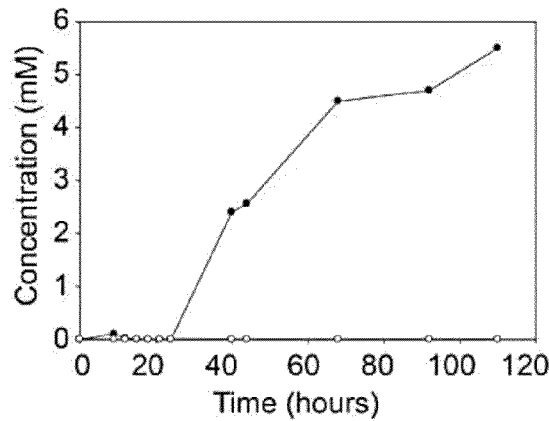
Figure 5B:
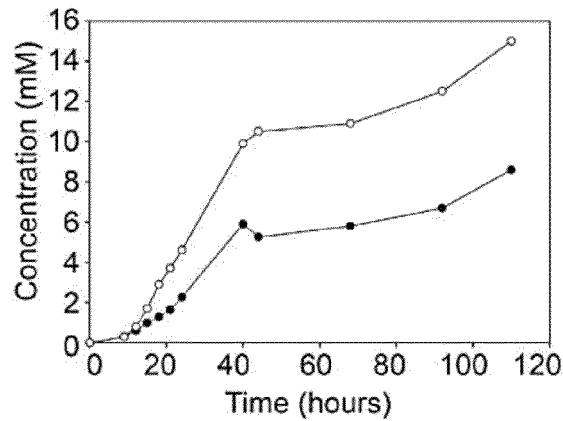
Figure 5C:
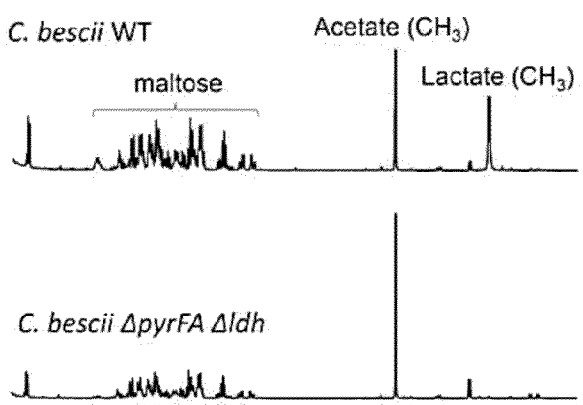

Cbes1918 is the only predicted lactate dehydrogenase coding region encoded in the *C. bescii* genome. To confirm that this coding region is solely responsible for the production of lactate in *C. bescii*, wild type, JWCB005 and JWCB017 were grown on 0.5% maltose, and fermentation products were analyzed by high-performance liquid chromatography (HPLC) (FIG. 5A and FIG. 5B) and nuclear magnetic resonance (NMR) analysis (FIG. 5C). No lactate was detected in the mutant by either method, as compared to approximately 5.0 mM lactate from the wild-type and parental strains.

Figure 5D:
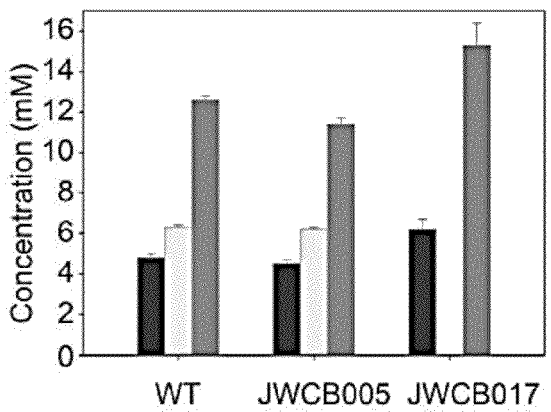
Figure 5E:
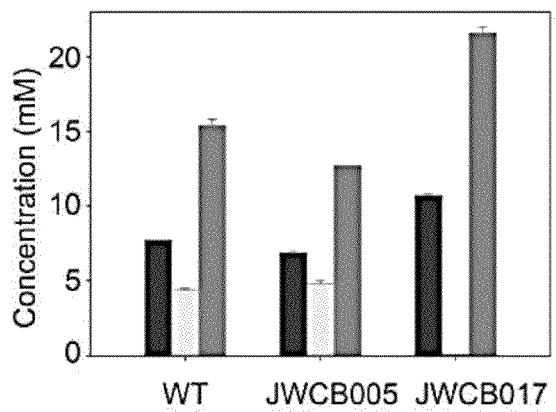

To compare the production of lactate, acetate and hydrogen, *C. bescii* wild-type and mutant strains were grown in LOD medium with soluble cellodextrans (cellobiose) or plant biomass (switchgrass) as carbon source. When grown on 0.5% cellobiose for 30 hours, JWCB017 showed 29% and 21% more acetate production and 37% and 34% more hydrogen production than wild type and parent strains, respectively (FIG. 5D). Cells grown for 120 hours on LOD medium supplemented with 0.5% switchgrass as the sole carbon source showed a similar profile to that on cellobiose, with the Δldh strain producing 38% and 40% more acetate and 55% and 70% more hydrogen than wild-type and parent strains (FIG. 5E).

Growth Yield Increases Upon Deletion of ldh.

Growth of JWCB017 was compared to the wild type and parental strains in defined media supplemented with either 0.5% maltose or 0.5% cellobiose. While growth of the ΔpyrFA parent strain on both maltose (FIG. 6A) and cellobiose (FIG. 6B) was indistinguishable from the wild type, the JWCB017 mutant strain reached a 34-53% higher final optical density than the wild type and parent. Interestingly, while the growth rate was comparable, the exponential growth phase of JWCB017 was extended resulting in higher cell densities.

These results demonstrate the genetic manipulation of *Caldicellulosiruptor* to delete the coding region encoding lactate dehydrogenase. While the wild type strain produced roughly equimolar amounts of acetate and lactate, the JWCB017 mutant strain no longer produced lactate, instead rerouting carbon and electron flux to acetate and $H_2$, respectively. The hydrogen yield observed for JWCB001 (~1.8 mol/mol of glucose) and JWCB005 (~1.7 mol/mol of glucose) was somewhat lower than the hydrogen yield reported values for *C. saccharolyticus* grown in culture media with added yeast extract, which improves yields (~2.5 mol/mol of glucose; Kadar et al., Appl Microbiol Biotechnol 2007, 74:1358-1367). JWCB017 (~3.4 mol/mol of glucose), however, provided a higher hydrogen yield than that reported for *C. saccharolyticus*. Yield and titer of acetate and $H_2$ were increased in the *C. bescii* ldh deletion strain using either model soluble substrates or real-world plant biomass.

Members of the genus *Caldicellulosiuptor* offer special advantages for biomass conversion to products of interest in that they are hyperthermophiles with optimal growth temperatures between 78° C.-80° C. and they are capable of using biomass without conventional pretreatment.

Interestingly, deletion of ldh resulted in a higher cell yield and longer exponential growth phase relative to the wild type. The increase in cell density may involve an increase in acetate production, which may increase ATP production per glucose via acetate kinase providing more energy for biosynthesis and growth. The fact that *C. bescii* JWCB017 grows to a higher density without an obvious effect on growth rate suggests that engineered strains may be able to compete well with the wild type strain and thrive in an industrial setting.

More advanced metabolic engineering strategies allowing genetic manipulation of *C. bescii* may increase the utility of *C. bescii* for industrial applications. In addition to the construction of deletions, this can enable insereting one or more heterologous coding regions into the *C. bescii* chromosome (so called genetic knock-ins), simplifying the process of heterologous coding region expression by eliminating the need for plasmid maintenance and increasing the number of coding regions that can be stably expressed. Thus, we have created a new platform for rational strain design in *C. bescii*. Genetic design of *C. bescii* may be exploited for applications such as, for example, lignocellulosic bioconversion involving, for example, increasing the titer of $H_2$, expressing heterologous pathways for production of, for example, liquid fuels and/or other chemicals, increasing robustness, and/or improving upon the native ability of *Caldicellulosiruptor* species to deconstruct and convert biomass without conventional pretreatment.

As used herein, the term "heterologous" refers to a biomolecule or bioprocess that is not natively present in a host cell. Thus, for example, a "heterologous polynucleotide" refers to a polynucleotide that does not native exist in a host cell, a "heterologous coding region" refers to a polynucleotide that encodes a polypeptide that is not natively produced by a host cell, and a "heterologous pathway" refers to a biosynthetic pathway that includes at least one biosynthetic step that is not natively performed by the host cell.

One obstacle to genetic manipulation of *C. bescii* involves restriction by CbeI endonuclease. Restriction by CbeI was shown to be an absolute barrier to DNA transformation (Chung et al., Journal of industrial microbiology & biotechnology 2011, 38:1867-1877), but could be overcome by in vitro methylation of DNA by a cognate methyltransferase, M.CbeI (Chung et al., PloS one 2012, 7:e43844).

In another aspect, this disclosure describes a genetically-modified *C. bescii* in which CbeI activity is reduced, resulting in a strain that is easily transformable with unmethylated heterologous DNA (e.g., from *E. coli*), eliminating the need for in vitro methylation by M.CbeI (Cbes2437).

Restriction Digestion Analysis of Chromosomal DNA from *Caldicellulosiruptor* Species.

The observation that restriction was an absolute barrier to DNA transformation of *C. bescii* prompted us to investigate the prevalence of functional restriction-modification (R-M) systems in other *Caldicellulosiruptor* species. M.CbeI-methylated DNA successfully transforms *C. hydrothermalis* (Example 3) suggesting that *C. hydrothermalis* and *C. bescii* might share similar R-M activities. Putative R-M systems with significant variation were detected in *Caldicellulosiruptor* species based on REBASE (Roberts et al., Nucleic acids research 2010, 38:D234-236) and GenBank (Benson et al., Nucleic acids research 2010, 38:D46-51) analysis. To investigate which, if any, of these R-M systems are functional, chromosomal DNA was isolated from seven *Caldicellulosiruptor* species and digested with each of nine different restriction endonucleases, all of which have commercially available cognate methyltransferases (Table 3 and FIG. 7). We found that all species tested contain at least three types of functional R-M systems (Table 3). DNA isolated from each of the seven species was resistant to digestion by BamHI and BspEI, indicating the presence of a cognate methyltransferase for these restriction endonucleases is common in this genus. Resistance to digestion by HaeIII was observed for *C. bescii, C. hydrothermalis, C. kristjansonii,* and *C. saccharolyticus.* Resistance to digestion by MboI was observed for *C. kristjansonii, C. saccharolyticus, C. obsidiansis, C. lactoaceticus,* and *C. kronotskyensis.* HaeIII (5'-GGCC-3') and MboI (5'-GATC-3') would be expected to act as a formidable barrier for DNA transformation from *E. coli* for these species, since both enzymes are four base cutters and are known to be absolute barrier to DNA transformation in other microorganisms (Chung et al., Journal of industrial microbiology & biotechnology 2011, 38:1867-1877; Grogan, Journal of bacteriology 2003, 185:4657-4661; Donahue et al., Molecular microbiology 2000, 37:1066-1074). *C. kronotskyensis* appears to be the most different from the other species in terms of R-M systems, as it has apparent methyltransferase activity specific to HpaII and MspI recognition sites. All seven tested species were sensitive to digestion by AluI, EcoRI, and HhaI (Table 3).

Construction of a cbeI Deletion in *C. bescii.*

Figure 8A:
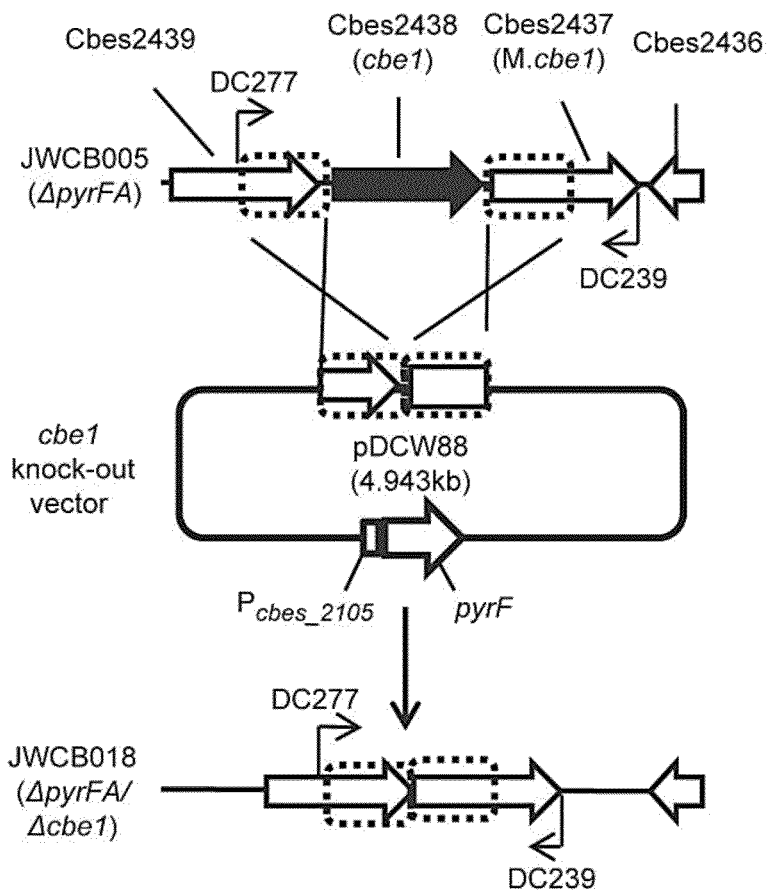

Transformation of *C. bescii* with heterologous DNA from *E. coli* involves in vitro methylation of the *E. coli* DNA with M.CbeI. (Chung et al., PloS one 2012, 7:e43844). More importantly, the degree of methylation in vitro affected transformation efficiency. To test whether a deletion of cbeI would alleviate restriction of DNA from *E. coli* in *C. bescii* and allow transformation of unmethylated DNA, we constructed a chromosomal deletion of cbeI (Cbes2438) in JWCB005 (FIG. 8A, Table 4, Example 3), using a targeted marker replacement strategy previously described (Chung et al., PloS one 2012, 7:e43844). The cbeI knock-out vector, pDCW88, contains a 927 bp DNA fragment that includes both the 5' (440 bp) and 3' (487 bp) flanking regions of cbeI, and the wild type pyrF cassette (Example 3) for uracil prototrophic selection of transformants (FIG. 8A, FIG. 9). This non-replicating vector in *C. bescii* was transformed into JWCB005 (ΔpyrFA) with selection for uracil prototrophy followed by counter-selection for 5-fluoroorotic acid (5-FOA) resistance.

Figure 8B:
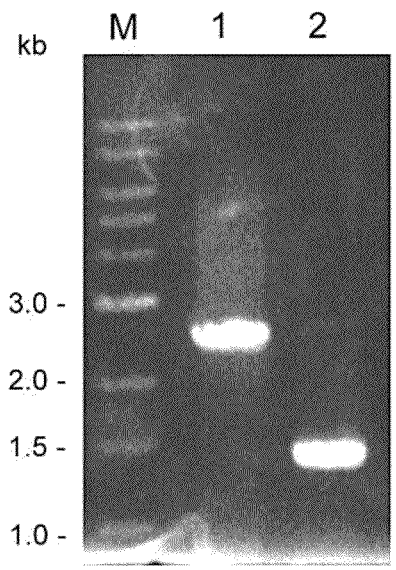

Initial screening of 18 isolates by PCR revealed merodiploids with a mixture of wild type and cbeI deletion genomes. Three of these were further purified on solid medium without 5-FOA and analyzed by PCR amplification of the cbeI locus in the chromosome with primers DC277 and DC239 (FIG. 8). PCR amplification of this locus from the parent strain JWCB005 (dpyrFA) produced the expected wild type ~2.4 kb band, while amplification from JWCB018 produced a ~1.4 kb band indicating a deletion within this region (FIG. 8B). The site of the deletion was confirmed by DNA sequence analysis of the PCR product. The resulting strain, JWCB018 (ΔpyrF ΔcbeI) (Table 4) was used for further analysis.

The cbeI coding region is located in the chromosome adjacent to the coding region encoding M.CbeI, its cognate methyltransferase (Chung et al., PloS one 2012, 7:e43844; Chung et al., Journal of industrial microbiology & biotechnology 2011, 38:1867-1877). The two coding regions are separated by only 45 bases, and are likely to be transcriptionally coupled. The deletion of cbeI spanned the entire cbeI coding region, but left the potential regulatory region upstream intact, and deleted only 23 bases of the downstream flanking region leaving the entire M.CbeI coding region intact. Chromosomal DNA isolated from JWCB018 was completely protected from cleavage by HaeIII and CbeI in vitro, suggesting that M.CbeI is still functional in JWCB018. Growth of this cbeI deletion mutant was comparable to growth of the parent JWCB005 and the wild type strain.

the JWCB018 is Efficiently Transformed with Unmethylated DNA.

Figure 10A:
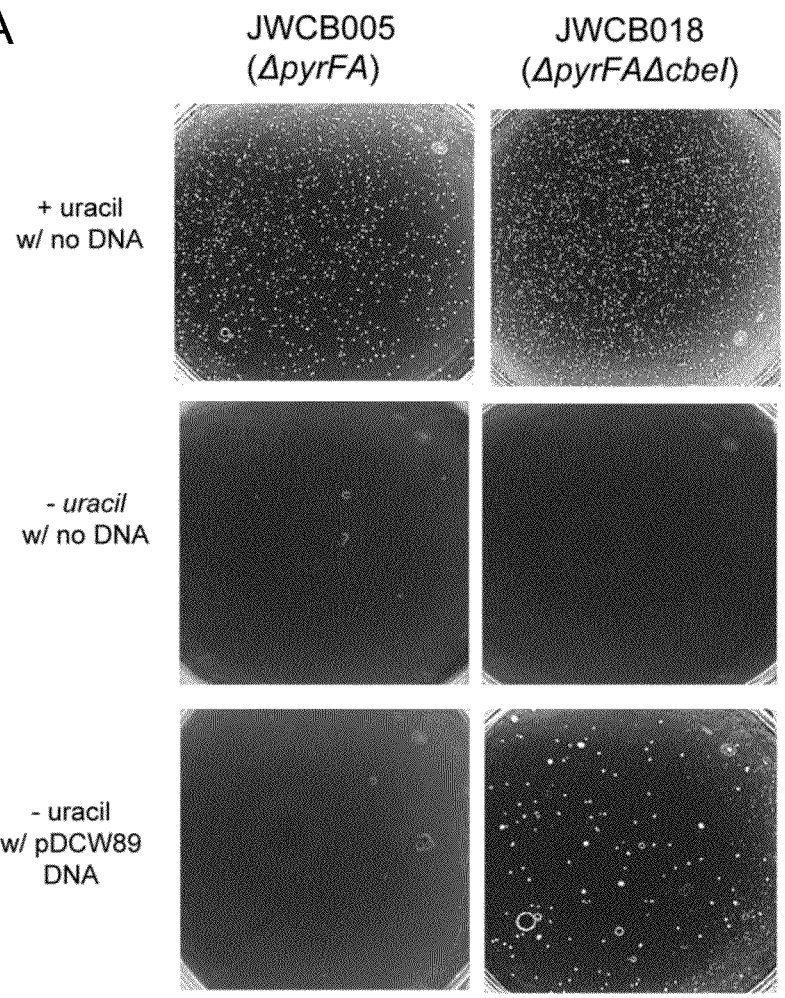
Figure 10B:
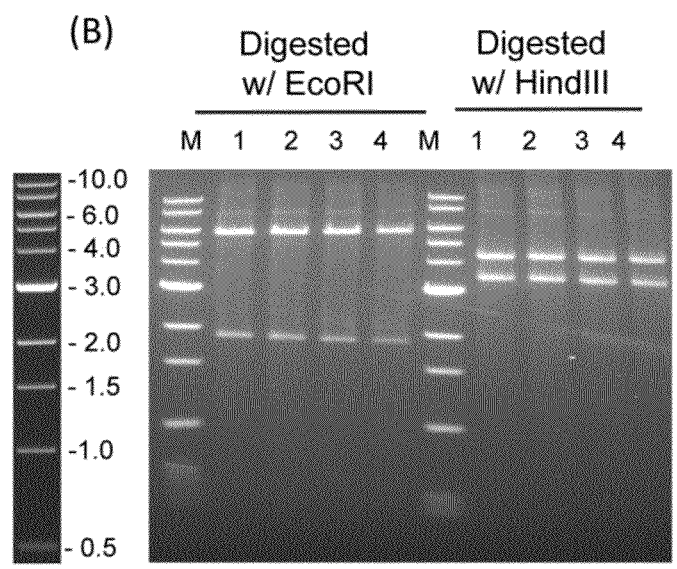

To assess the effect of the cbeI deletion on transformation of *C. bescii* with unmethylated DNA from *E. coli,* JWCB005 (ΔpyrFA) and JWCB018 (ΔpyrFA ΔcbeI) were transformed with unmethylated pDCW89 DNA, using a replicating shuttle vector (Example 1) containing a wild type copy of the pyrF allele for uracil prototrophic selection (FIG. 10). No transformants of the parent strain, JWCB005, were detected using unmethylated plasmid DNA isolated from *E. coli* ($<10^{-8}$ transformants per µg plasmid DNA). The ΔcbeI strain, however, was readily transformed with unmethylated pDCW89 DNA isolated from *E. coli* (~$1.0 \times 10^3$ transformants per µg of plasmid DNA, FIG. 10A). Methylated plasmid DNA transformed into the parent strain (JWCB005) at a frequency (~$0.5 \times 10^3$ transformants per mg plasmid DNA) and the difference may reflect incomplete methylation of the plasmid DNA in vitro. Transformation of *C. bescii* was initially confirmed by PCR amplification of the pSC101 *E. coli* replication origin fragment present only in the plasmid. Total DNA isolated from JWCB018 transformants was used to "back-transform" *E. coli* and plasmid DNA isolated from these back-transformants was analyzed by restriction digestion (FIG. 10B). pDCW89 DNA isolated from the "back transformants" was indistinguishable from the pDCW89 used to transform *C. bescii* and showed no obvious signs of rearrangement or deletion through transformation into JWCH018, replication in *C. bescii*, or back-transformation to *E. coli* (FIG. 10B).

Plasmid DNA Isolated from *C. hydrothermalis* Readily Transforms Strain JWCB005 (ΔpyrFA) without In Vitro Methylation.

Plasmid DNA was isolated from *C. hydrothermalis* transformants and used to transform *C. bescii*. Transformants were obtained at frequencies comparable to M.CbeI-methylated plasmid (~$0.5 \times 10^3$ per mg of plasmid DNA). The presence of pDCW89 in transformants was confirmed using PCR amplification of the aac (apramycin resistance gene), pSC101 ori region, and pyrF cassette, contained only on the plasmid. The size of the PCR products obtained in this analysis were as expected and were generated from total DNA isolated from the JWCB005 transformants and plasmid DNA isolated from *E. coli*, but not from JWCB005 (FIG. 11). Total DNA, isolated from JWCB005 transformants, was back-transformed to *E. coli* for further analysis. Restriction analysis of plasmid DNA isolated from back-transformants showed that pDCW89 was structurally stable through transformation and replication in *C. bescii*. Thus, we have constructed a variant of *C. bescii* that possesses a deletion of cbeI (Cbes2438) sufficient to disrupt cbeI activity that is otherwise an absolute barrier to transformation of *C. bescii* with heterologous DNA. Disruption of cbeI activity is the first targeted genetic deletion demonstrated in a *Caldicellulosiruptor* spp. and the resulting variant, JWCB018 (ΔpyrFA ΔcbeI), is readily transformed by heterologous DNA without in vitro methylation. PCR amplification and sequencing suggested that this deletion left the adjacent methyltransferase (M.CbeI) intact and its function was confirmed by the fact that chromosomal DNA isolated from JWCB018 was protected from digestion by CbeI and HaeIII in vitro.

While exemplified in the context of a deletion of the entire cbeI coding region, the genetic manipulation that allows for transformation of *C. bescii* with heterologous DNA can include any modification that interferes with CbeI restriction activity. such modifications can include, for example, a partial deletion of the cbeI coding region sufficient to disrupt expression of the remaining cbeI coding region and/or disrupt CbeI restriction activity of any CbeI fragment polypeptide that may be expressed.

Also, while exemplified in the context of permitting transformation of *C. bescii* with heterologous DNA isolated from *E. coli*, the heterologous DNA used to transform the *C. bescii* variant can be isolated from any appropriate source or prepared synthetically.

The construction of this variant *C. bescii* strain removes a substantial barrier to transformation and chromosomal modification. Moreover, the variant *C. bescii* strain permits genetic manipulation without labor intensive such as, for example, modifying the vector prior to transformation, using engineered vectors containing no or fewer restriction sites recognized by restriction endonuclease in host, conditionally inactivating the R-M systems, and/or using group II intron insertion technology.

The ability to make targeted genetic deletions is itself a powerful and direct tool for the investigation of in vivo genetic function and the deletion of this endonuclease resulted in a strain that can provide the basis for further genetic manipulation. The combined efficiencies of transformation and homologous recombination (with as few as 450 bp of homology) in *C. bescii* allows one to use non-replicating plasmids for genetic manipulation. This is fortuitous and a significant benefit for the development of *Caldicellulosiruptor* species as consolidated bioprocessing (CBP) organisms. The proven CBP microbe, *Clostridium thermocellum*, for example, is genetically tractable but the efficiency of transformation and/or recombination does not permit the use of non-replicating plasmids for marker replacement, significantly extending the time required for mutant construction.

Thus, in one aspect, this disclosure describes a method for improving transformation efficiency of a microbe in which restriction is a barrier to transformation. Generally, the method includes genetically modifying the microbe to decrease restriction activity and introducing a heterologous polynucleotide into the genetically modified microbe. In some embodiments, the microbe may be a microbe in which restriction is an absolute barrier to transformation with a heterologous polynucleotide.

In some embodiments, the genetic modification can include a deletion of at least a portion of a coding region that encodes a restriction endonuclease sufficient to reduce—in some cases even eliminate—restriction activity of the endonuclease and, therefore, allow maintenance of the heterologous polynucleotide in the genetically modified and transformed host cell.

Isolation of JWCB005, a *C. bescii* Variant for Nutritional Selection of Transformants.

Attempts to use drug resistance markers for selection of transformants in *C. bescii* are often unsuccessful either because the genetic products are unstable at 75° C. and/or because of high levels of natural resistance in *C. bescii*. Orotidine monophosphate (OMP) decarboxylase, encoded by the pyrF coding region in bacteria (ura3 in yeast), converts the pyrimidine analog 5-fluoroorotic acid (5-FOA) to 5-fluorouridine monophosphate, which is ultimately converted to fluorodeoxyuridine by the uracil biosynthetic pathway, a toxic product that kills growing cells that are synthesizing uracil. Mutants of pyrF are, therefore, uracil auxotrophs and resistant to 5-FOA, providing uracil prototrophy as a selection for the wild type allele and 5-FOA resistance as a counter selection for the mutant allele.

Certain pyrF mutants can be constructed by deleting most of the pyrBCF region. Such mutants thus require complementation of all three coding regions for successful transformation. Transformation efficiency generally decreases as plasmid size increases, so it can be difficult to efficiently transform such a mutant.

Figure 12A:
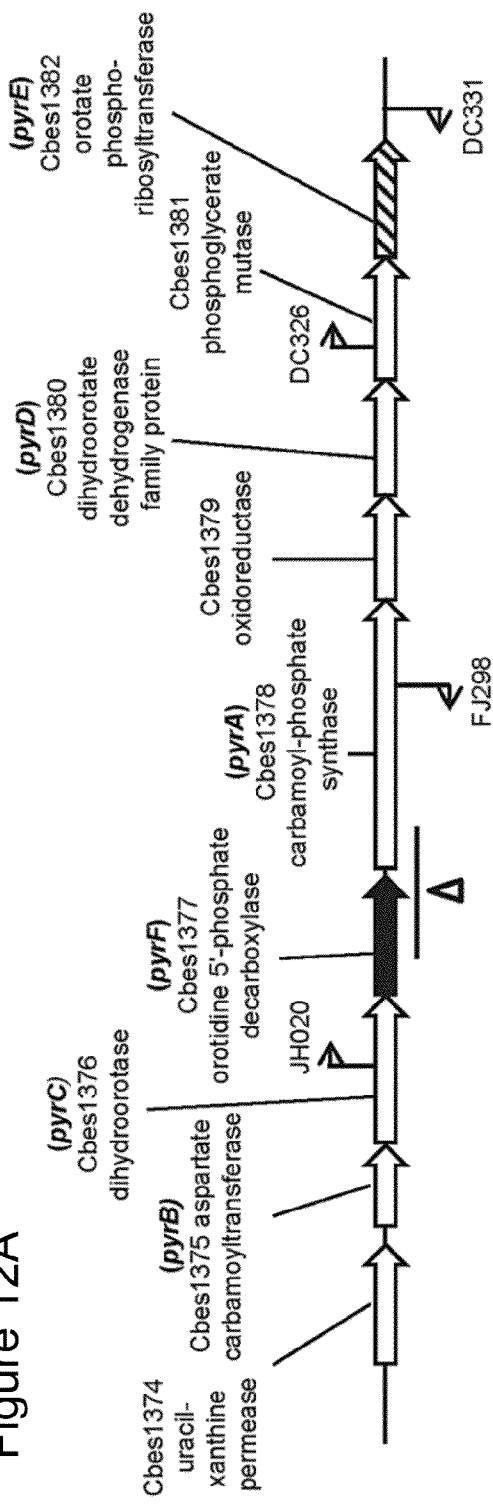
Figure 12B:
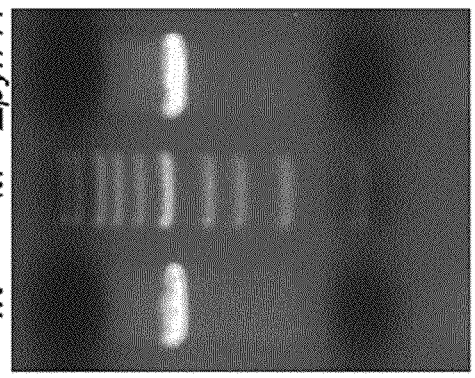
Figure 12C:
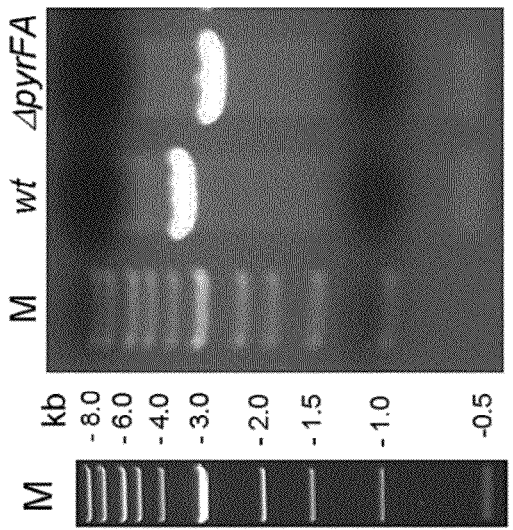

We isolated a different mutant that was complemented by the pyrF coding region alone. To obtain this new deletion strain, *C. bescii* cells were plated on modified DSMZ 640 media (Chung et al. (2012) PLoS One 7: e43844) containing 8 mM 5-FOA. Spontaneous resistance to 5-FOA was observed at a frequency of approximately $10^{-5}$ at 65° C. Among 30 mutants isolated, one, designated JWCB005 (Table 6), had an 878 bp deletion that spans most of the pyrF open reading frame (Cbes1377), and part of the adjacent gene, pyrA (Cbes1378) (FIG. 12A). The extent of the deletion was defined by PCR amplification of the pyrFA region in the mutant and subsequent sequencing of the PCR product (FIG. 12B). We also PCR amplified and sequenced the pyrE region, also required for uracil biosynthesis, and found it to be wild type (FIG. 12C).

JWCB005 is a tight uracil auxotroph capable of growth in media supplemented with uracil, but not orotate, confirming that pyrF function was absent in this deletion. The function of pyrA does not seem to be affected by the deletion, because transformation with pDCW89, containing only the wild type pyrF allele, was able to complement the uracil auxotrophy without added orotate, the product of pyrA in uracil biosynthetic pathway. As with all such deletions, reversion to uracil prototrophy was not a concern making prototrophic selection possible no matter how low the frequency of transformation. Growth of this mutant (JWCB005) supplemented with uracil (40 μM) was comparable to that of the wild type, reaching a cell density of ~$2\times10^8$ in 24 hours.

Construction of a Replicating Shuttle Vector Based on pBAS2.

*C. bescii* contains two native plasmids, pBAL and pBAS2, 8.3 kb and 3.7 kb, respectively (Dam et al. (2011) Nucleic Acids Res 39: 3240-3254; Clausen et al. (2004) Plasmid 52: 131-138). Because of its relatively small size, we chose to use pBAS2 to supply replication functions for *C. bescii* in the shuttle vector. To avoid disrupting the replication functions of the pBAS2 plasmid, we linearized the plasmid DNA just upstream of the Cbes2777 ORF and inserted the aac coding region for selection of apramycin resistance in *E. coli*. The *C. bescii* pyrF gene, under the transcriptional control of the promoter of the ribosomal protein Cbes2105 (30S ribosomal protein S30EA), was used for selection of uracil prototrophy in the *C. bescii* pyrFA deletion mutant (JWCB005), and the pSC101 replication origin for replication in *E. coli*.

Figure 13A:
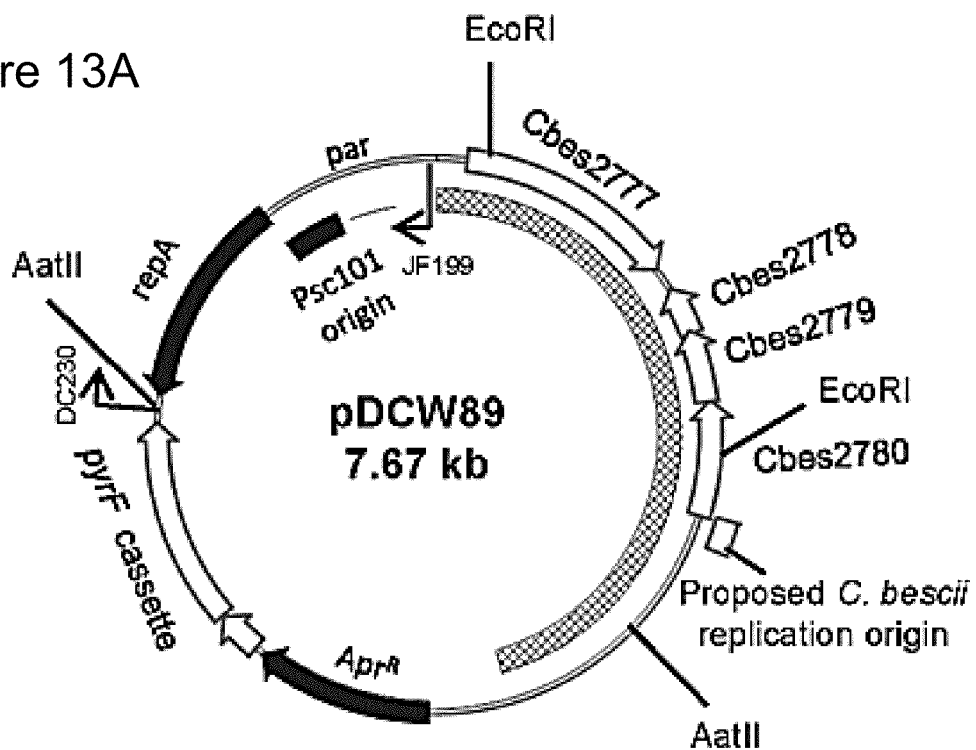
Figure 13B:
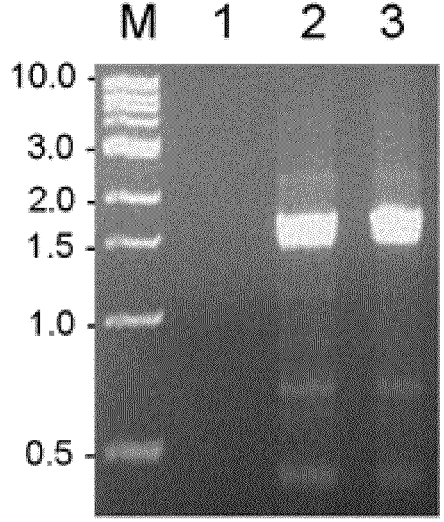
Figure 13C:
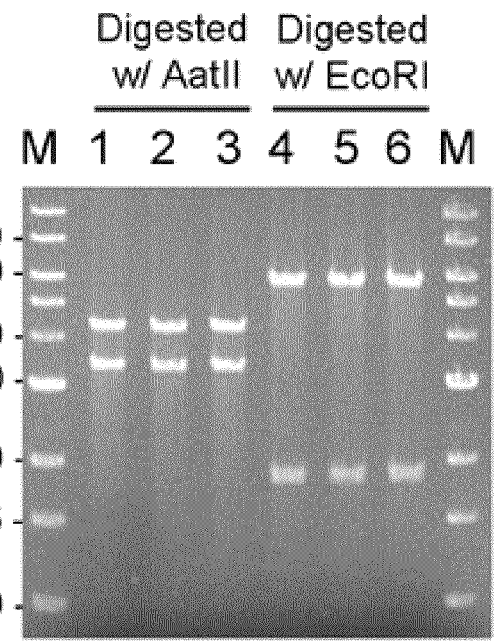

The resulting plasmid, pDCW89 (FIG. 13A), was transformed into *C. bescii* by electroporation, and cells were plated onto defined medium without uracil as described (Chung et al. (2012) PLoS One 7: e43844). Uracil prototrophic colonies were selected and transformation was confirmed by PCR amplification of a portion of the pSC101 replication origin present only in pDCW89 (FIG. 13B). Total DNA isolated from two biologically independent transformants was used to back-transform *E. coli*. Restriction digestion analysis showed that the plasmid was unchanged during transformation and replication in *C. bescii* and/or subsequent back transformation to *E. coli* (FIG. 13C). This result suggests that it was replicating autonomously in both organisms. The resulting strain was designated JWCB011 (Table 6). The transformation frequency varied between experiments, but was typically about 500 transformants per μg of plasmid DNA. This efficiency was 10 times higher than the transformation efficiency observed with non-replicating plasmids in *C. bescii* (Chung et al. (2012) PLoS One 7: e43844).

Assessment of Plasmid Maintenance, and Relative Copy Number in *C. bescii*.

To assess plasmid maintenance and relative copy number, *C. bescii* transformants were serially sub-cultured every 16 hours for five passages in selective and nonselective liquid LOD medium (Farkas et al. (2013) Journal of industrial Microbiology & Biotechnology 40:41-49). Total DNA isolated from cells after each passage was used for Southern hybridization analysis (FIG. 16). To generate a probe for the detection of a sequence contained once on both the plasmid and the chromosome, primers JF396 and JF397 were used to amplify a fragment of the pyrF coding region remaining in the genome of JWCB005, and also contained on the plasmid. Relative copy number was determined as the ratio of band intensity of the plasmid derived copy of the pyrF locus (7.7 kb) compared to the chromosomal derived copy of the pyrF locus (3.7 kb) in JWCB005 (FIG. 16). The relative intensity was 0.8 to 1.1 suggesting that the shuttle vector exists as a single copy per chromosome (FIG. 16). Most plasmids that replicate via a rolling circle mechanism exist in high copy per chromosome (Espinosa et al. (1995) FEMS Microbiol Lett 130: 111-120) and the native pBAS2 may exist in high copy as well. The relative copy-number of pBAS2 was determined by qPCR with primer pairs targeting specific regions of pBAS2 and/or the chromosome. The relative copy-number of pBAS2 was calculated to be seventy-five copies per chromosome based on two biologically independent analyses. The fact that the shuttle vector exists in a single copy per chromosome may reflect the fact that it competes with the endogenous replicon as they share replication and maintenance functions. The 4.3 kb band indicates the pyrF-containing fragment in wild type *C. bescii* (lane 12) and 8.3 kb band is non-specific hybridization with pBAL, the larger of two endogenous plasmids in *C. bescii* (FIG. 16).

Plasmid maintenance was determined by assessing the presence of the plasmid after passage with and without nutritional selection over the five successive transfers. Southern analysis showed that the plasmid relative copy number remains constant with selection, but that the plasmid is quickly lost without selection (FIG. 16). A single passage in nonselective media (with 40 µM uracil) is enough for the plasmid to be lost from the majority of cells (FIG. 16).

Transformation of *C. hydrothermalis* with Shuttle Vector DNA Methylated with M.CbeI.

Restriction of transforming DNA is a barrier to transformation with heterologous DNA (e.g., from *E. coli*). Transformation of plasmid DNA from *E. coli* into wild-type *C. bescii* can involve in vitro methylation with an endogenous α-class N4-Cytosine methyltransferase, M.CbeI (Chung et al. (2012) PLoS One 7: e43844). To test whether modification by M.CbeI also allowed transformation of other members of this genus, a spontaneous mutation resistant to 5-FOA was isolated in *C. hydrothermalis* (Chung et al. (2013) J Ind Microbiol Biotechnol: 10.1007/s10295-10013-11244-z), JWCH003 (Table 6). This mutant was a tight uracil auxotroph and was used as a host for plasmid transformation.

Unmethylated plasmid DNA isolated from various *E. coli* hosts failed to transform this mutant but DNA that has been methylated with M.CbeI transformed at a frequency similar to that for *C. bescii* (typically about 500 transformants per µg of plasmid DNA). Transformants were initially confirmed by PCR amplification of the aac coding region contained exclusively on the plasmid. As shown in FIG. 17, restriction digestion analysis using HindIII and EcoRI of shuttle vector plasmid DNA isolated from *C. hydrothermalis* transformants was indistinguishable from that isolated from *E. coli* (FIG. 17B and FIG. 17C) suggesting that it is structurally stable in *C. hydrothermalis*. Thus, modification with M.CbeI may have utility in DNA transformation of a variety of *Caldicellulosiruptor* species. These data also provide evidence that the use of the wild type *C. bescii* pyrF allele under the control of the ribosomal protein S30EA promoter functions in at least one other species and may be a useful selection marker for many species. This shuttle vector may, therefore, facilitate extension of genetic methods to a number of other *Caldicellulosiruptor* species.

Shuttle vector plasmid DNA was readily isolated from *C. hydrothermalis*, suggesting that the vector may exist in higher copy in *C. hydrothermalis* than in *C. bescii*. FIG. 17A shows that the uncut plasmid DNA isolated from *C. hydrothermalis* migrated slower than that isolated from *E. coli*. This may be due, at least in part, to differences in the degree of methylation of the DNA in these different hosts. These results suggest that *C. hydrothermalis*, like *C. bescii*, contains a functional CbeI/M.CbeI like restriction-modification system and is consistent with the observation that pDCW89 isolated from *C. hydrothermalis* was resistant to digestion by purified CbeI or HaeIII (NEB) endonucleases (FIG. 17D).

Cloning of a CBM and a Linker Region of the celA Coding Region into pDCW89.

Figure 18B:
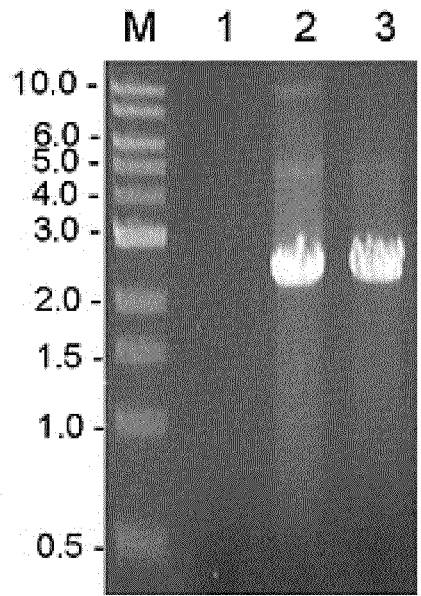
Figure 18C:
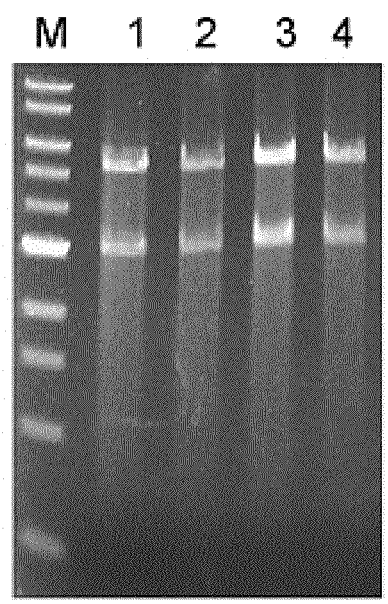

To test the use of pDCW89 as a cloning vector, a 0.68 kb DNA fragment containing a carbohydrate binding domain (CBM) and linker region derived from celA (Cbes1867) was cloned into pDCW89 (FIG. 18, pDCW129). Methylated pDCW129 was successfully transformed into JWCB005 at a comparable transformation efficiency to pDCW89. Transformation of *C. bescii* with pDCW129 was initially confirmed by PCR amplification of the region spanning the pyrF cassette and only in the plasmid (FIG. 18B). Total DNA isolated from JWCB018 transformants was used to "back-transform" into *E. coli* and plasmid DNA isolated from these back-transformants was analyzed by restriction digestion by EcoRV (FIG. 18C) and EcoRI and AatII. pDCW129 DNA isolated from the "back transformants" was indistinguishable from the pDCW129 used to transform *C. bescii* and showed no obvious signs of rearrangement or deletion through transformation and replication in JWCB005.

Thus, JWCB005, which contains a small deletion within the pyrFA locus, allows complementation of uracil auxotrophy with a single gene, pyrF. We constructed an *E. coli/C. bescii* shuttle vector by combining a native plasmid, pBAS2, with an *E. coli* vector and a pyrF cassette for nutritional selection of transformants (FIG. 13A). Methylation with M.CbeI methyltransferase was required for transformation of plasmid DNA isolated from *E. coli* into *C. bescii* (Chung et al. (2012) PLoS One 7: e43844). While it is possible that there is another endonucleases present in *C. bescii*, modification of heterologous DNA by M.CbeI was sufficient for successful transformation, and rescued plasmid did not show any signs of rearrangement during transformation and replication in *C. bescii* (FIG. 13C and FIG. 18C).

The shuttle vector replicates autonomously in *C. bescii* in single copy per chromosome and is stably maintained under selection, but quickly lost without selection (FIG. 16). This feature of the plasmid could be advantageous for future genetic applications that require plasmid curing, eliminating the need for counter-selection with 5-FOA or other antimetabolites that are potentially mutagenic. Single copy plasmids have many additional advantages over high copy plasmids providing expression of genes at physiologically relevant levels, and complementation analysis.

This shuttle is selectable in a uracil auxotrophic mutant of *C. hydrothermalis*. The development of genetic system in *C. hydrothermalis* is important for a number of reasons. *C.*

*hydrothermalis* contains fewer IS elements compared with other *Caldicellulosiruptor* species, and may exhibit fewer genome stability issues associated with stress conditions such as, for example, nutritional selections and counter-selections. *C. hydrothermalis* is one of the least cellulolytic species of the eight well-characterized *Caldicellulosiruptor* species (Blumer-Schuette et al. (2012) J Bacteriol 194: 4015-4028) and provides the opportunity to explore the mechanisms (or key enzymes) related to plant biomass degradation by heterologous expression of genes derived from the most cellulolytic *Caldicellulosiruptor* species, *C. bescii* and *C. saccharolyticus* (Blumer-Schuette et al. (2012) J Bacteriol 194: 4015-4028).

Moreover, the shuttle vector may be used to genetically modify pyrF mutant strains in other *Caldicellulosiruptor* species. For example, its use for cloning homologous proteins (e.g., Ce1A) will allow the study of enzymes predicted to be glycosylated in vivo making homologous expression essential.

In another aspect, this disclosure describes the direct conversion of plant biomass to ethanol by *C. bescii* that have been genetically modified using the molecular tools described above. While exemplified in the context of converting plant biomass to ethanol, the methods exemplified may be modified to genetically modify other *Caldicellulosiruptor* species and/or to modify the *Caldicellulosiruptor* microbes to produce other products such as, for example, any carbon-based product. Exemplary carbon-based products include, for example, carbon-based fuels (e.g., ethanol, jet fuel, etc.) and/or commodity chemicals.

Heterologous Expression of the *Clostridium thermocellum* adhE Gene in *C. bescii*.

The *C. thermocellum* adhE coding region (Cthe0423) is a bifunctional acetaldehyde-CoA/alcohol dehydrogenase. The coding region was amplified from *C. thermocellum* (ATCC 27405) chromosomal DNA and cloned into pDCW144 (FIG. 19 and FIG. 20) under the transcriptional control of the *C. bescii* S-layer protein (Cbes2303) promoter ($P_{S-layer}$). RNA profiling has shown that S-layer protein RNA is abundant and present throughout growth suggesting that the promoter may be strong and constitutive. A rho-independent transcription terminator derived from a region immediately downstream of Cbes2303 was fused to the end of adhE coding region (FIG. 20A and FIG. 19) and the vector adds a C-terminal His-tag to the AdhE protein. In addition, the final vector, pDCW144, contained a 2.025 kb DNA fragment from the intercistronic region between Cbes0863 and Cbes0864 (FIG. 20A and FIG. 19) to allow targeted integration into the *C. bescii* chromosome. The vector does not contain an origin of replication for *C. bescii* and cannot replicate autonomously. It also contained a wild type pyrF expression cassette (Example 3).

pDCW144 was transformed into JWCB018 (ΔpyrFA ldh::ISCbe4 Δcbe1), which contains a deletion of the CbeI restriction enzyme and an insertion into the ldh coding region. It also contains a deletion in the pyrF locus resulting in uracil auxotrophy and allowing for selection for uracil prototrophy followed by counter-selection for 5-fluoroorotic acid (5-FOA) resistance as described in Example 2 and depicted in FIG. 20A.

Figure 20B:
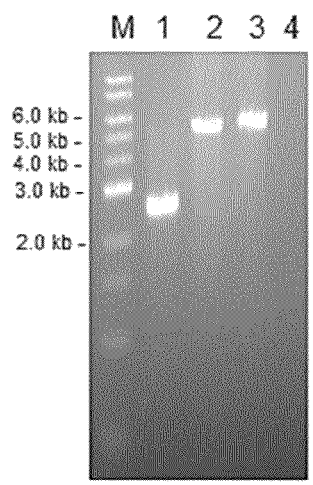

Two of the forty transformants analyzed by PCR amplification using primers DC477 and DC478 (FIG. 20B) contained segregated insertions of the $P_{S-layer}$-adhE cassette at the targeted chromosome site. As shown in FIG. 20, the parent strain, JWCB018, produced the expected wild type ~2.44 kb band, while amplification from JWCB032 produced a ~5.04 kb band indicating a knock-in of expression cassette within this region (FIG. 20B).

Figure 20C:
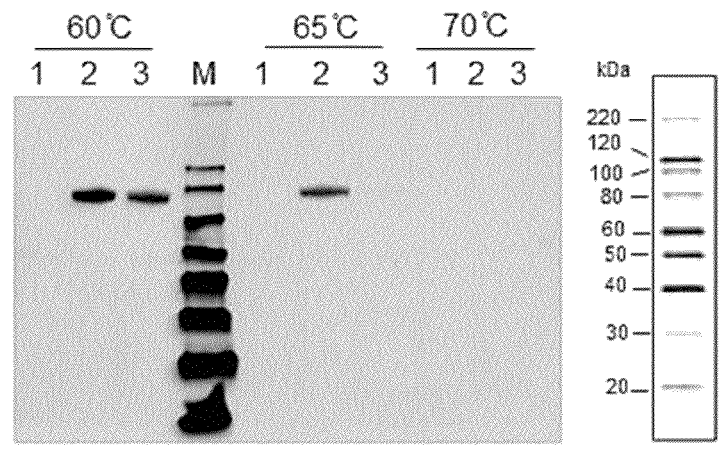

Expression of the AdhE protein was detected in transformants containing the expression cassette by Western hybridization using commercially available His-tag monoclonal antibody (FIG. 20C). Cells were grown in LOD medium with 10 g/l cellobiose and 100 μM uracil to mid-log phase at 60° C., 65° C., or 70° C. The wild type AdhE protein was expressed and readily detected in cells grown at 60° C. and 65° C., but not at 70° C. Since the optimal temperature for growth for *C. thermocellum* is 60° C. (Brown et al. (2011) Proc Natl Acad Sci USA 108: 13752-13757), the AdhE protein or adhE mRNA may not be stable at 70° C.

We also expressed a variant of the AdhE protein, AdhE*, from *C. thermocellum* that has been shown to increase ethanol tolerance without losing functional activity for ethanol production (Brown et al. (2011) Proc Natl Acad Sci USA 108: 13752-13757). The construction of JWCB033 (ΔpyrFA/Δcbe1::$P_{S-layer}$Cthe-adhE*) was the same as that for JWCB032. Interestingly, the AdhE* was detected at 60° C., but not 65° C. or 70° C. suggesting that either the protein or its mRNA it is less thermostable than the wild type.

Analysis of Metabolic Products from *C. bescii* Containing the *C. thermocellum* adhE Coding Region.

High performance liquid chromatography (HPLC) was performed to determine the fermentation products from *C. bescii* mutant strains. Strain JWCB018 (ΔpyrFA ldh::ISCbe4 Δcbe1) is the background genetic strain used in these studies. Strain JWCB032 (ΔpyrFA ldh::ISCbe4 Δcbe1::$P_{S-layer}$Cthe-adhE) contains the *C. thermocellum* adhE coding region described above. FIG. 21 shows fermentation product profiles from batch cultures grown at 65° C. with different substrates, 10 g/liter cellobiose, 20 g/liter AVICEL, or 20 g/liter unpretreated switchgrass.

Figure 21A:
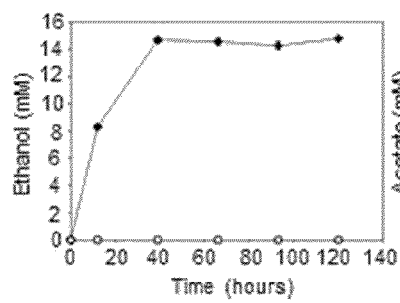
Figure 21B:
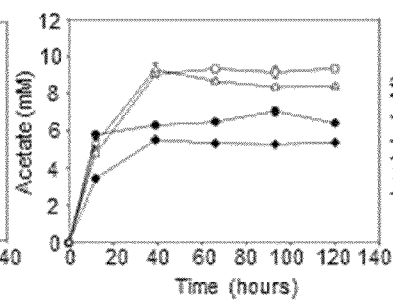
Figure 21C:
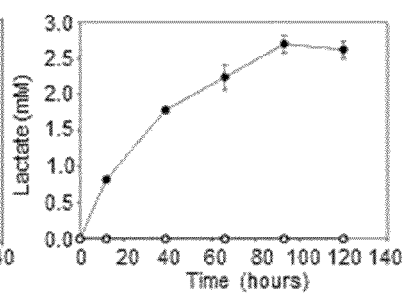

Wild type *C. bescii*, JWCB018, JWCB032 and JWCB033 were grown on 1% cellobiose, and fermentation products were analyzed by HPLC (FIG. 21). JWCB032 produced ethanol up to 14.8 mM (FIG. 21A). No lactate was detected in the mutants JWCB018, JWCB032, and JWCB033, compared to approximately 2.7 mM lactate from the wild-type (FIG. 21C). JWCB018 and JWCB033 show higher amounts of acetate produced compared other strains, wild-type and JWCB032 (FIG. 21B) because JWCB018 and JWCB033 produce only acetate and hydrogen as final products from pyruvate (FIG. 21). In contrast, wild-type *C. bescii* produces lactate, acetate, and hydrogen, while JWCB032 produces ethanol, acetate and hydrogen as final products.

To compare the final products of fermentations on different substrates, a model microcrystalline cellulosic substrate, AVICEL (2%, wt/vol), and a real world substrate, unpretreated switchgrass (2%, wt/vol), were used for batch fermentations by *C. bescii* strains. When grown on AVICEL, wild-type produced lactate (3.1 mM), acetate (5.4 mM) and no ethanol (FIG. 22). JWCB018 and JWCB033 show similar final product profiles: acetate (7.3~8.2 mM), no lactate, and no ethanol (FIG. 22). The engineered strain, JWCB032, however, shows the direct production of ethanol from 2% AVICEL up to approximately 14 mM (FIG. 22A) and lowest acetate production (4.3 mM) (FIG. 22B). The maximum ethanol produced on 2% AVICEL (14.0 mM) was similar to that on 1% cellobiose (14.6 mM).

The genetically engineered strain, JWCB032, is able to produce ethanol directly from unpretreated switchgrass. All four *C. bescii* strains in this study were grown on 2% switchgrass, and the end product analysis shows similar profiles for ethanol (FIG. 23A), acetate (FIG. 23B) and lactate (FIG. 23C) productions compared to those on cellobiose (FIG. 21) and AVICEL (FIG. 22). JWCB032 produce 11.0 mM of ethanol at 40 hours of incubation and reached 12.8 mM of ethanol accumulation at 120 hours of incubation.

Growth Properties of Ethanol-Producing *C. bescii* Strains and Ethanol Tolerance of *C. bescii*.

Figure 24A:
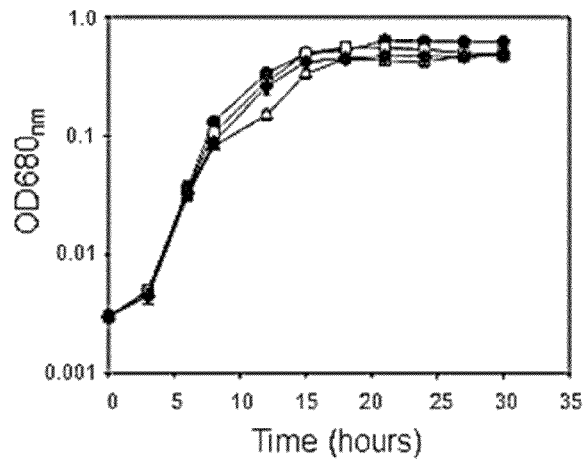
Figure 24B:
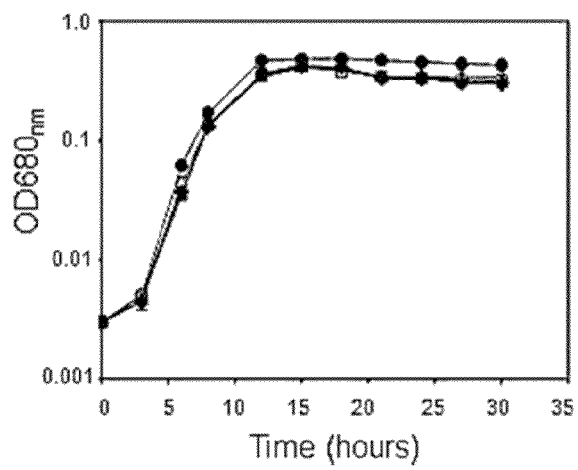

To determine the overall effect of heterologous expression of adhE and its derivative on *C. bescii* growth properties, growth of JWCB032 and JWCB033 were compared to the wild type and parental (JWCB018) strains in LOD medium supplemented with 1% cellobiose as carbon source and 1 mM uracil (FIG. 24). The expressed enzymes AdhE and AdhE* are only stable and active near or below 65° C. based on the Western-blot analysis shown in FIG. 20C and fermentation product analysis (FIGS. 22-24). Therefore, we performed analyses at both 65° C. (FIG. 24A) and 75° C. (FIG. 24B). Growth at 75° C. was faster than at 65° C. Based on growth curves shown in FIG. 24, *C. bescii* cells reached stationary phase after approximately 12 hours at 75° C., but it took approximately 20 hours at 65° C. *C. bescii* were growing up to an $OD_{680nm}$ of 0.5-0.6 with shaking at 150 rpm. These results indicate that the expression of AdhE and its derivative do not negatively affect growth compared to the parental strain (JWCB018) and wild type.

To determine the *C. bescii* ethanol tolerance, the wild-type strain was assayed for its ability to grow in LOD medium with 1% cellobiose as the sole carbon source and elevated levels of ethanol at both 65° C. and 75° C. with shaking (150 rpm) (FIG. 25). Growth of *C. bescii* in the presence of 200 mM ethanol concentration in LOD media was comparable with the no ethanol medium at both 65° C. and 75° C. However, *C. bescii* exhibits higher ethanol tolerance at 65° C. than at 75° C. The 450 mM ethanol concentration has a modest effect on growth at 65° C., but it significantly inhibits growth at 75° C. The growth of *C. bescii* was completely inhibited at 600 mM ethanol concentration. The ethanol tolerance of *C. bescii* is comparable to *Clostridium thermocellum* ATCC27405 (Brown et al. (2011) Proc Natl Acad Sci USA 108: 13752-13757).

EXEMPLARY EMBODIMENTS

Embodiment 1

A recombinant *Caldicellulosiruptor* microbe genetically modified to produce a greater amount of acetate than a comparable wild type control.

Embodiment 2

A recombinant *Caldicellulosiruptor* microbe genetically modified to produce a greater amount of $H_2$ than a comparable wild type control.

Embodiment 3

A recombinant *Caldicellulosiruptor* microbe genetically modified to produce that produces a greater amount of ethanol than a comparable wild type control.

Embodiment 4

The recombinant *Caldicellulosiruptor* microbe of any preceding exemplary Embodiment wherein the *Caldicellulosiruptor* microbe is *Caldicellulosiruptor bescii*.

Embodiment 5

The recombinant *Caldicellulosiruptor* microbe of any preceding exemplary Embodiment wherein the recombinant *Caldicellulosiruptor* microbe produces lactate in an amount less than a comparable wild type control.

Embodiment 6

The recombinant *Caldicellulosiruptor* microbe of any preceding exemplary Embodiment comprising a deletion of at least a portion of a lactate dehydrogenase coding region.

Embodiment 7

The recombinant *Caldicellulosiruptor* microbe of exemplary Embodiment 6 wherein the lactate dehydrogenase coding region is Cbes_1918.

Embodiment 8

The recombinant *Caldicellulosiruptor* microbe of any preceding exemplary Embodiment genetically modified to exhibit decreased CbeI endonuclease activity compared to a comparable wild-type control.

Embodiment 9

The recombinant *Caldicellulosiruptor* microbe of any preceding exemplary Embodiment genetically modified to exhibit increased efficiency of transformation with unmethylated heterologous DNA.

Embodiment 10

The recombinant *Caldicellulosiruptor* microbe of exemplary Embodiment 8 or exemplary Embodiment 9 comprising a deletion of at least a portion of a cbeI coding region.

Embodiment 11

A recombinant *Caldicellulosiruptor* microbe genetically modified to exhibit decreased restriction compared to a comparable wild-type control compared to a comparable wild-type control.

Embodiment 12

A recombinant *Caldicellulosiruptor* microbe genetically modified to exhibit increased efficiency of transformation with unmethylated heterologous DNA.

Embodiment 13

The recombinant *Caldicellulosiruptor* microbe of exemplary Embodiment 11 or exemplary Embodiment 12 comprising a deletion of at least a portion of a cbeI coding region.

Embodiment 14

The recombinant *Caldicellulosiruptor* microbe of any one of exemplary Embodiments 10-13 further comprising a heterologous DNA.

Embodiment 15

A method comprising:
growing the recombinant *Caldicellulosiruptor* microbe of any one of exemplary Embodiments 1 and 4-7 under conditions effective for the recombinant *Caldicellulosiruptor* microbe to produce acetate.

Embodiment 16

The method of exemplary Embodiment 15 further comprising collecting at least a portion of the acetate.

Embodiment 17

A method comprising:
growing the recombinant *Caldicellulosiruptor* microbe of any one of exemplary Embodiments 2 and 4-7 under conditions effective for the recombinant *Caldicellulosiruptor* microbe to produce $H_2$.

Embodiment 18

The method of exemplary Embodiment 17 further comprising collecting at least a portion of the $H_2$.

Embodiment 19

A method comprising:
growing the recombinant *Caldicellulosiruptor* microbe of any one of exemplary Embodiments 3-7 under conditions effective for the recombinant *Caldicellulosiruptor* microbe to produce ethanol.

Embodiment 20

The method of exemplary Embodiment 19 further comprising collecting at least a portion of the ethanol.

Embodiment 21 The method of any one of exemplary Embodiments 15-20 wherein the conditions comprise a carbon source that comprises napier grass, Bermuda grass, switchgrass, or a hardwood.

Embodiment 22

The method of exemplary Embodiment 20 wherein the carbon source comprises unpretreated switchgrass.

Embodiment 23

A method comprising:
introducing a heterologous polynucleotide into the *Caldicellulosiruptor* microbe of any one of exemplary Embodiments 11-14.

Embodiment 24

The method of exemplary Embodiment 23 wherein the heterologous polynucleotide is unmethylated.

Embodiment 25

A method for improving transformation efficiency of a microbe in which restriction is a barrier to transformation, the method comprising:
genetically modifying the microbe to decrease restriction activity; and
introducing a heterologous polynucleotide into the genetically modified microbe.

In the preceding description, particular embodiments may be described in isolation for clarity. Unless otherwise expressly specified that the features of a particular embodiment are incompatible with the features of another embodiment, certain embodiments can include a combination of compatible features described herein in connection with one or more embodiments.

For any method disclosed herein that includes discrete steps, the steps may be conducted in any feasible order. And, as appropriate, any combination of two or more steps may be conducted simultaneously.

The present invention is illustrated by the following examples. It is to be understood that the particular examples, materials, amounts, and procedures are to be interpreted broadly in accordance with the scope and spirit of the invention as set forth herein.

EXAMPLES

Example 1

Metabolic Engineering of *Caldicellulosiruptor bescii* Yields Increased Hydrogen Production from Lignocellulosic Biomass Strains, Growth Conditions and Molecular Techniques.

A spontaneous mutant containing a deletion within the pyrFA locus of *C. bescii*, JWCB005 (Chung et al., PLoS One 2013, 8:e62881 (Example 3); Chung et al., Biotech biofuels 2013, 6:82 (Example 2)), was used in this study to select transformants. *C. bescii* strains were grown in modified DSMZ516 medium or LOD (low osmolality defined growth medium) (Farkas et al., J Ind Microbiol Biotechnol 2013, 40:41-49) containing 0.5% maltose as carbon source, final pH 7.0. Liquid cultures were grown from a 0.5% inoculum or a single colony and incubated at 75° C. in anaerobic culture bottles degassed with five cycles of vacuum and argon. A solid medium was prepared by mixing an equal volume of liquid medium at a 2× concentration with the same volume of (wt/vol) agar, 3.6% (Difco, Sparks, Md.) that had been previously autoclaved. Both solutions were maintained at 70° C. and poured into petri dishes immediately after mixing. A series of dilutions of this culture were mixed with 4 ml of soft top agar (1.5% of agar) and poured across the top of the solid agar medium. The plates were degassed with five cycles of vacuum and argon and incubated at 75° C. for 4 days in anaerobic jars. *E. coli* DH5α was used to prepare plasmid DNA. Cells were grown in LB broth supplemented with apramycin (50 μg/ml). Plasmid DNA was isolated using a Qiagen Mini-prep Kit (Qiagen; Valencia, Calif.). A complete list of strains, plasmids, and primers used in this study is shown in Tables 1 and 2.

TABLE 1

Plasmids and *C. bescii* strains (JWCB) used in Example 1.

| Strains and Plasmids | Description and/or relevant characteristics | Source or reference |
|---|---|---|
| pDCW88 | Non-replicating plasmid in *C. bescii* | A (Example 2) |
| pDCW121 | ldh knock-out plasmid | This study |
| JWCB001 | *C. bescii* wild-type DSM 6725 | B |
| JWCB005 | DSM 6725 ΔpyrF4 | C (Example 3) |
| JWCB017 | DSM 6725 ΔpyrF4 Δldh | This study |

A: Chung et al., Biotech biofuels 2013, 6: 82
B: Svetlichnyi et al., Microbiol 1990, 59: 598-604
C: Chung et al., PLoS One 2013, 8: e62881

TABLE 2

Oligonucleotides used in Example 1.

| Primer | Sequence 5'-3' | SEQ ID No: |
|---|---|---|
| DC081 | TCCAATGATCGAAGTTAGGCTGGT | 1 |
| DC348 | GAATTCTCTGACGCTCAGTGGAACGAA | 2 |
| DC349 | GAAAACAAATGGGCTTGGGAGGATAGGAGGCTGT | 3 |
| DC350 | TGGGCTTGGGAGGATAGGAGGCTGTCTAAAAACAA | 4 |
| DC351 | TGCCAAGATATGAAATGAGAACT | 5 |
| DC356 | CGTCTCATCTGTGCATATGGACAGTTATAATCCCAAAAGGAGGATTGGATCC | 6 |

Construction of pDCW121.

To construct a plasmid for deletion of the ldh coding region (Cbes1918), three cloning steps including overlapping polymerase chain reactions were used. All PCR amplifications were performed using Pfu Turbo DNA polymerase (Agilent Technologies; Santa Clara, Calif.). A 1009 bp fragment containing a KpnI site upstream of the ldh coding region was amplified using primers DC348 and DC349. A 1,011 bp fragment containing an EcoRI site downstream of ldh, was amplified using primers DC350 and DC351. The two fragments were joined by overlapping PCR using primers DC348 and DC351 to generate a 2,020 bp product that was cloned into pDCW88 (Chung et al., Biotech biofuels 2013, 6:82 (Example 2)) using the KpnI and EcoRI sites. The resulting plasmid, pDCW121, was transformed into *E. coli* DH5α by an electrotransformation via a single electric pulse (1.8 kV, 25 μF and 200Ω) in a pre-chilled 1 mm cuvette using a Bio-Rad gene Pulser (Bio-Rad Laboratories; Hercules, Calif.). Transformants were selected on LB solid medium containing apramycin (50 μg/ml final).

Competent Cells, Transformation and Mutant Selection in *C. bescii*.

To prepare competent cells, a 50 ml culture of JWCB005 was grown in LOD minimal medium at 75° C. for 18 hours (to mid exponential phase) and 25 ml of the culture was used to inoculate a 500 ml culture of LOD (low osmolarity defined growth medium) supplemented with 40 μM uracil and a mixture of 19 amino acids (5% inoculum, v/v) (Farkas et al., J Ind Microbiol Biotechnol 2013, 40:41-49). The 500 ml culture was incubated at 75° C. for 5 hours and cooled to room temperature for 1 hr. Cells were harvested by centrifugation (6000×g, 20 min) at 25° C. and washed three times with 50 ml of pre-chilled 10% sucrose. After the third wash, the cell pellet was resuspended in 50 μl of pre-chilled 10% sucrose in a microcentrifuge tube and stored at −80° C. until needed. Before transformation, plasmids from *E. coli* cells were methylated in vitro with *C. bescii* methyltransferase (M.CbeI, Chung et al., PLoS One 2012, 7:e43844) and methylated plasmid DNAs (0.5-1.0 μg) were added to the competent cells, gently mixed and incubated for 10 minutes in ice. Electrotransformation of the cell/DNA mixture was performed via single electric pulse (1.8 kV, 25 μF and 350Ω) in a pre-chilled 1 mm cuvette using a Bio-Rad gene Pulser (Bio-Rad Laboratories; Hercules, Calif.). After pulsing, cells were inoculated into 10 ml of LOC medium (low osmolarity complex growth medium; Farkas et al., J Ind Microbiol Biotechnol 2013, 40:41-49) and incubated for 4 hours at 75° C. 100 μl of the culture was transferred into 20 ml of defined medium without uracil. After 18 hours incubation at 75° C., cells were harvested by centrifugation (at 6000×g for 20 min) and resuspended in 1 ml of 1× basal salts. 100 microliters of the cell suspension was plated onto solid defined media with 40 μM uracil and 8 mM 5-FOA (5-fluoroorotic acid monohydrate).

Analytical Techniques for Determining Fermentation End Products.

Batch fermentations were conducted in stoppered 125 ml serum bottles containing 50 ml LOD medium with 5 g/l maltose, cellobiose or switchgrass. Cultures of JWCB005 and JWCB017 were supplemented with 40 μM uracil. Triplicate bottles were inoculated with a fresh 2% (v/v) inoculum and incubated at 75° C. without shaking. Total cell dry weight (CDW) was determined by concentrating 25 ml of each culture on dried, preweighed 47 mm Supor membrane filters (0.45, Pall Corporation; Port Washington, N.Y.) and washed with 10 ml of $_{dd}H_2O$. Cell retentates were dried for 16 hours at 85° C. and weighed on an analytical balance. Culture supernatants were analyzed via HPLC using a Waters Breeze 2 system (Waters Chromatography; Milford, Mass.) operated under isocratic conditions at 0.6 ml/min with 5 mM $H_2SO_4$ as a mobile phase. Analytes were separated on an Aminex HPX-87H column (Bio-Rad Laboratories, Hercules, Calif.) at 60° C. and monitored via refractive index (RI) using a Waters 2414 RI detector. Total peak areas were integrated using Waters Breeze 2 software and compared against peak areas and retention times of known standards for each analyte of interest. $H_2$ was measured using an Agilent Technologies 6850 Series II Gas Chromatograph equipped with a thermal conductivity detector at 190° C. with a $N_2$ reference flow and a HP-PLOT U Column (30 m×0.32 mm). To measure organic acid production, Nuclear magnetic resonance (NMR) analysis was performed. One-dimensional 1H-NMR spectra were recorded at 298° K with a Varian Inova-NMR operating at 600 MHz for 1H and equipped with a 5-mm NMR cold probe. Samples (500 μL) of cell free culture media were mixed with 150 μL of $D_2O$ as internal lock and immediately analyzed. 128 scans were recorded for each sample using a pre-saturation method to suppress the water resonance. The amounts of the most abundant components in the samples were calculated by integration of the proton signals in the spectra. The data were normalized to the amount of acetic acid in each sample.

Biomass Preparation.

Air-dried switchgrass (*Panicum virgatum*, Alamo variety) was reduced to 60 mesh using a Wiley Mini-Mill (Thomas Scientific; Swedesboro, N.J.). The ground switchgrass was subjected to a hot water treatment similar to that described by Yang et al. (Appl Environ Microbiol 2009, 75:4762-2769) however the biomass was boiled in distilled $H_2O$ (2% w/v) for 1 hour rather than treating overnight at 75° C. The switchgrass was then washed and dried overnight at 50° C. before dispensing into serum bottles as previously described (Yang et al., Appl Environ Microbiol 2009, 75:4762-2769).

Example 2

Overcoming Restriction as a Barrier to DNA Transformation in *Caldicellulosiruptor* Species Results in Efficient Marker Replacement Strains, Media and Growth Conditions.

*Caldicellulosiruptor* and *E. coli* strains used in this study are listed in Table 4. All *Caldicellulosiruptor* species were grown anaerobically in liquid or on solid surface in either modified DSMZ 516 medium (Chung et al., PLoS one 2012, 7:e43844) or in low osmolarity defined (LOD) medium (Farkas et al., Journal of industrial microbiology & biotechnology 2013, 40:41-49) with maltose as the carbon source. *C. bescii*,

*C. kristjansonii*, and *C. obsidiansis* were incubated at 75° C. *C. hydrothermalis*, *C. kronotskyensis*, *C. lactoaceticus*, and *C. saccharolyticus* were incubated at 68° C. For growth of auxotrophic mutants, the defined medium contained 40 µM uracil. *E. coli* strain DH5α was used for plasmid DNA constructions and preparations. Standard techniques for *E. coli* were performed as described (Sambrook, *Molecular Cloning: A Laboratory Manual*. Cold Spring Harbor Laboratory Press; 2001). *E. coli* cells were grown in LB broth supplemented with apramycin (50 µg/mL) and plasmid DNA was isolated using a Qiagen Mini-prep Kit. Chromosomal DNA from *Caldicellulosiruptor* strains was extracted using the Quick-gDNA™ MiniPrep (Zymo Research; Irvine, Calif.) or using the DNeasy Blood & Tissue Kit (Qiagen; Valencia, Calif.) according to the manufacturer's instructions. Plasmid DNA isolation from *Caldicellulosiruptor* species was performed as described (Chung et al., Journal of industrial microbiology & biotechnology 2011, 38:1867-1877).

TABLE 4

Strains and plasmids used in Example 2.

| Strain or plasmid | Strain and genotype/phenotype | Source |
|---|---|---|
| *Caldicellulosiruptor* | | |
| *C. bescii* DSM6725 | wild type/(ura+/5-FOA$^S$) | DSMZ[1] |
| *C. hydrothermalis* DSM18901 | wild type/(ura+/5-FOA$^S$) | DSMZ[1] |
| *C. kristijansonii* DSM12137 | wild type/(ura+/5-FOA$^S$) | DSMZ[1] |
| *C. saccharolyticus* DSM8903 | wild type/(ura+/5-FOA$^S$) | DSMZ[1] |
| *C. obsidiansis* ATCC BAA-2073 | wild type/(ura+/5-FOA$^S$) | DSMZ[1] |
| *C. lactoaceticus* DSM9545 | wild type/(ura+/5-FOA$^S$) | DSMZ[1] |
| *C. kronotskyensis* DSM12137 | wild type/(ura+/5-FOA$^S$) | DSMZ[1] |
| JWCB005 | *C. bescii* ΔpyrF4/(ura−/5-FOA$^R$) | 2 |
| JWCB018 | *C. bescii* ΔpyrFAΔcbeI/(ura−/5-FOA$^R$) | This study |
| JWCH003 | *C. hydrothermalis* IScahyI insertion mutation in pryF coding region/ (ura−/5-FOA$^R$) | 2, 3 |
| JWCH005 | JWCH003 transformed with M. CbeI methylated pDCW89/(ura+/5-FOA$^S$) *Escherichia coli* | 2 |
| JW291 | DH5α containing pDCW88 (Apramycin$^R$) | This study |
| JW292 | DH5α containing pDCW89 (Apramycin$^R$) Plasmids | 2 |
| pDCW88 | cbeI knock-out vector (Apramycin$^R$) | This study |
| pDCW89 | *E. coli/Caldicellulosiruptor* species shuttle vector (Apramycin$^R$) | 2 |

[1] *German Collection of Microorganisms and Cell Cultures*
2 Chung D et al., PLoS one, 2013, 8: e62881 (Example 3)
3 Chung et al., Journal of industrial microbiology & biotechnology 2013. 10.1007/s10295-013-1244-z Construction of pDCW88.

A 927 bp DNA fragment containing the 5' flanking region (440 bp) and the 3' flanking region (487 bp) of cbeI (Cbes2438) was generated by overlap extension polymerase chain reaction (OE-PCR) using primers DC265 (with KpnI site), DC266, DC267, and DC268 (with ApaLI site). All PCR reactions were performed using pfu turbo (Agilent Technologies; Santa Clara, Calif.), and *C. bescii* genomic DNA as a template. The DNA fragments containing the apramycin resistance cassette, pyrF cassette, and the *E. coli* pSC101 replication origin, were amplified from pDCW 89 (Example 3) using primers DC081 (with KpnI site) and DC262 (with ApaLI site). These two linear DNA fragments were digested with KpnI and ApaLI, and ligated to generate pDCW88 using Fast-link DNA Ligase kit (Epicentre Biotechnologies; Madison, Wis.) according to the manufacturer's instructions. DNA sequences of the primers are shown in Table 5. A diagram of pDCW88 is shown in FIG. 9. *E. coli* strain DH5α cells were transformed by electroporation in a 2-mm-gap cuvette at 2.5 V and transformants were selected for apramycin resistance. The sequence of pDCW88 was confirmed by Automatic sequencing (Macrogen, Inc.; Rockville, Md.). All plasmids are available on request.

TABLE 5

Primers used in Example 2.

| Primers | Sequences (5' to 3') | SEQ ID No: | Description |
|---|---|---|---|
| DC277 F | TCTACACTCTTGCTTACACAGGT | 7 | amplify the cbeI (Cbes_2438) region |
| DC239 R | TCTCCTCGAGCAGACCAAGTGCGTATTTTTC | 8 | amplify the cbeI (Cbes_2438) region |
| DC265 F | AGAGAGGTACCTGCAACATCCGGCTTAATGAC | 9 | amplify 440 bp of 5' flanking region of (Cbes_2438) |
| DC266 R | TGTTAAAACCACCTACCTAATCTTATCATGTT GGAAGGCAAATTGA | 10 | amplify 440 bp of 5' flanking region (Cbes_2438) |
| DC267 F | AGATTAGGTAGGTGGTTTTAACA | 11 | amplify 487 bp of 3' flanking region (Cbes_2438) |
| DC268 R | TGTGTGGTGCACTCCTTGATAATTTCAGCTGCCT | 12 | amplify 487 bp of 3 'flanking (Cbes_2438) |
| DC262 F | TGTGTGGTGCACTCTGACGCTCAGTGGAACGAA | 13 | amplify the *E. coli* features from pDCW 89 |

TABLE 5-continued

Primers used in Example 2.

| Primers | Sequences (5' to 3') | SEQ ID No | Description |
|---|---|---|---|
| DC081 R | AGAGAGGTACCACCAGCCTAACTTCGATCATTGGA | 14 | amplify the *E. coli* features from pDCW 89 |
| JF263 F | AGGTACCGGTTCATGTGCAGCTCCATC | 15 | amplify the aac coding region cassette |
| JF264 R | CTCCAACGTCATCTCGTTCTC | 16 | amplify the aac coding region cassette |
| DC100 F | TAGTCTTGATGCTTCACTGATAG | 17 | amplify the pSC101 *E. coli* replication origin |
| JF199 R | CGCTAACGGATTCACCACT | 18 | amplify the pSC101 *E. coli* replication origin |
| DC233 F | ATCCGTTGATCTTCCTGCAT | 19 | amplify the pyrF cassette |
| DC235 R | AGGATCTGAGGTTCTTATGGCTC | 20 | amplify the pyrF cassette |

Screening, Purification, and Sequence Verification of Deletion Mutants.

To construct strain JWCB018, one microgram of M.CbeI methylated pDCW88 DNA was used to electrotransform JWCB005 (ΔpyrFA) as described (Chung et al., PloS one 2012, 7:e43844). Cells were then plated onto solid defined medium (without uracil or casein) and uracil prototrophic transformant colonies were inoculated into liquid medium for genomic DNA extraction and subsequent PCR screening of the targeted region. Confirmed transformants were inoculated into nonselective liquid defined medium, with 40 µM uracil, and incubated overnight at 75° C. to allow loop-out of the plasmid DNA. The cultures were plated onto 5-FOA (8 mM) containing solid medium. After initial screening, transformants containing the expected deletion were further purified by three additional passages under selection on solid medium and screened a second time by PCR to check for segregation of the deleted allele. The deletions were then verified by PCR amplification and sequence analysis. A PCR product was generated from genomic DNA by using primers (DC277 and DC239) outside the homologous regions used to construct the deletion, and internal primers were used to sequence the PCR product. For PCR, the extension time was sufficient to allow amplification of the wild-type allele, if it were still present. Another set of primers, one located inside of the Cbes2438 open reading frame, and the other located outside of the flanking region were used for further verification. Growth of this strain, JWCB018, supplemented with uracil (40 µM) was comparable to wild type reaching a cell density of ~2×10$^8$ in 20 hours. Cells were counted in a Petroff Hausser counting chamber using a phase-contrast microscope with 40× magnification.

Transformation of *C. bescii* and Selection of Transformants.

Electrotransformations of JWCB005 and JWCB018 with unmethylated pDCW89 from *E. coli* or isolated plasmid DNA from *C. hydrothermalis* transformants were performed as described (Chung et al., PloS one 2012, 7:e43844). For selection of transformants, after electro-pulse the recovery cultures with pDCW89 DNA (0.5-1.0 µg) were plated onto the defined medium without casein or uracil. Uracil prototrophic transformants were inoculated into liquid medium for DNA isolation. The presence of plasmid sequences in *C. bescii* transformants was confirmed by PCR amplification of the aac (apramycin resistance cassette) coding region, the pSC101 ori region, and the pyrF cassette, present only on pDCW89. The transformation frequencies reported herein take into account the number of cells plated as determined by culture cell counts (this does not take into account the plating efficiency), and, where indicated, the total amount of DNA added (i.e., the number of transformants per microgram of DNA). *E. coli* strain DH5α cells were used for back-transformation.

Restriction Endonuclease Digestion of *Caldicellulosiruptor* Species Chromosomal DNA.

Chromosomal DNA isolated from seven *Caldicellulosiruptor* species was subjected to digestion with the REs AluI, BamHI, BspEI, EcoRI, HaeIII, HhaI, HpaII, MboI, and MspI. All enzymes were from New England Biolabs. For each reaction, 1 microgram of DNA was incubated with the enzyme and appropriate buffer for 1 hour according to the manufacturer's instructions. After incubation, digestion patterns were compared by electrophoresis on a 1.0% agarose gel.

Example 3

Construction of a Stable Replicating Shuttle Vector for *Caldicellulosiruptor* Species: Use for Extending Genetic Methodologies to Other Members of this Genus Strains, Media and Growth Conditions.

*C. bescii*, *C. hydrothermalis*, and *E. coli* strains used in this study are listed in Table 6. *Caldicellulosiruptor* species were grown anaerobically in liquid or solid modified DSMZ516 medium (Chung et al. (2012) PLoS One 7: e43844) or in low osmolarity defined (LOD) growth medium (Farkas et al. (2013) Journal of industrial Microbiology & Biotechnology 40:41-49) with maltose as the sole carbon source as described at 75° C. for *C. bescii* or at 68° C. for *C. hydrothermalis*. For growth of auxotrophic mutants JWCB005 and JWCH003, the defined medium containing 40 µM uracil was used. *E. coli* strains DH5α (dam$^+$dcm$^+$), BL21 (dam$^+$dcm$^-$), and ET12567 (dam$^-$dcm$^-$) were used for plasmid DNA constructions and preparations. Standard techniques for *E. coli* were performed as described (Sambrook et al. (2001) *Molecular Cloning: A Laboratory Manual*: Cold Spring Harbor Laboratory Press). *E. coli* cells were grown in L broth supplemented with apramycin (50 µg/ml), kanamycin (25 µg/ml), or spectinomycin (20 µg/mL), where appropriate. *E. coli* plasmid DNA was isolated using a Qiagen Mini-prep Kit. Chromosomal DNA from *Caldicellulosiruptor* species was extracted using the Quick-gDNA™ MiniPrep (Zymo Research; Irvine, Calif.)

according to the manufacturer's instructions. Total DNA was isolated from *Caldicellulosiruptor* species as described (Lipscomb et al. (2011) Appl Environ Microbiol 77: 2232-2238), except that adding additional lysozyme (30 μg/ml) for 1 hour at room temperature in lysis buffer (Chung et al. (2011) J Ind Microbiol Biotechnol 38: 1867-1877) and sonication were employed to enhance the cell lysis. Plasmid DNA isolation from *Caldicellulosiruptor* species was performed as described (Chung et al. (2011) J Ind Microbiol Biotechnol 38: 1867-1877).

Isolation of 5-FOA Resistant/Uracil Auxotrophic Mutants.

A spontaneous deletion within the *C. bescii* DSM6725 pyrFA locus (FIG. 12A, Table 6) was isolated using the same approaches as previously described (Chung et al. (2012) PLoS One 7: e43844). Growth of this strain, JWCB005, supplemented with uracil (40 μM) was comparable to wild type reaching a cell density of ~2×10$^8$ in 24 hours. Cells were counted in a Petroff-Housser counting chamber using a phase-contrast microscope with 40× magnification.

Construction of Plasmids.

Figure 15A:
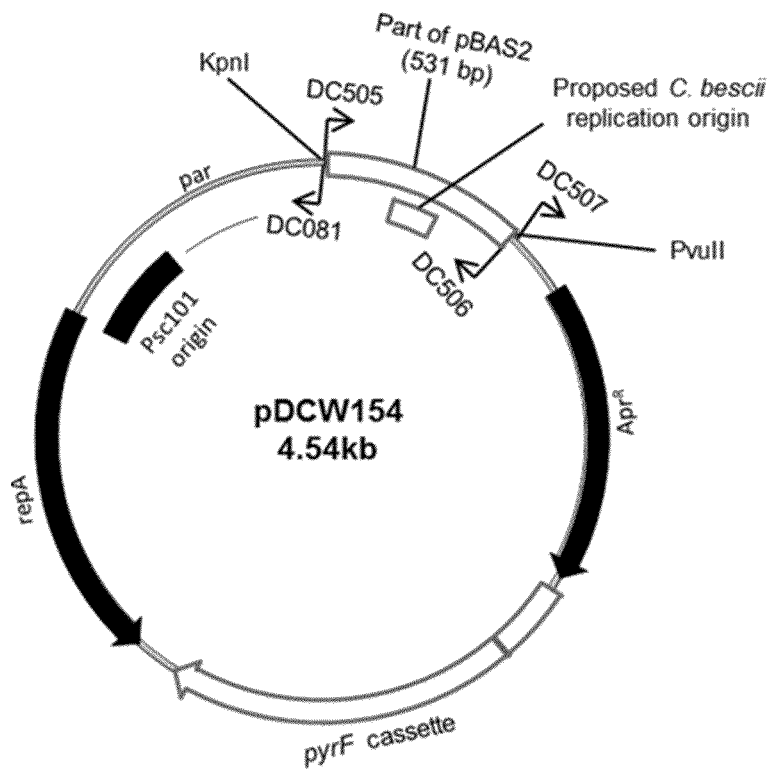
Figure 15B:
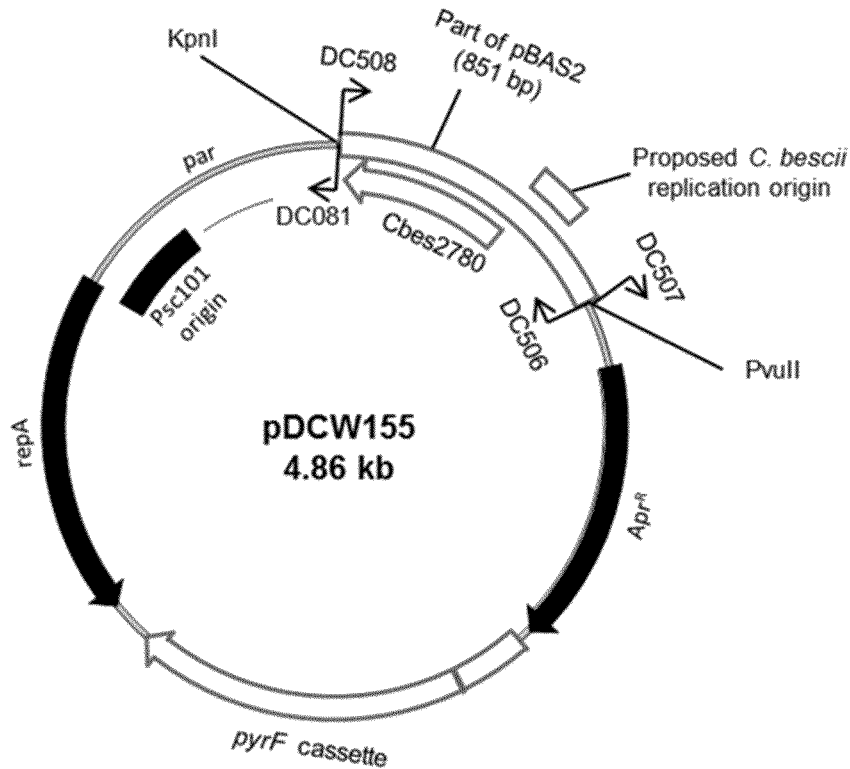

Plasmids were generated using high fidelity pfu AD DNA polymerase (Agilent Technologies; Santa Clara, Calif.), restriction enzymes (New England Biolabs; Ipswich, Mass.), and Fast-Link™ DNA Ligase (Epicentre Biotechnologies; Madison, Wis.) according to the manufacturer's instructions. Plasmid pDCW89 (FIG. 13A, FIG. 14) was constructed in three cloning steps. First, a 2.9 kb of DNA fragment, containing the PSC101 replication origin and an apramycin resistance cassette (Apr$^R$), was amplified by PCR using the primers DC080 and DC084 and pDCW68 (Chung et al. (2011) J Ind Microbiol Biotechnol 38: 1867-1877) as template. The 2.9 kb DNA fragment was then blunt-end ligated after treatment with T4 PNK (New England Biolabs; Ipswich, Mass.) to construct Intermediate vector I (FIG. 14). A cassette containing the wild-type pyrF coding region was constructed by overlap extension polymerase chain reaction (OE-PCR) placing the pyrF coding region under the transcriptional control of the Cbes2105 (30S ribosomal protein S30EA) promoter. A 199 bp portion of the regulatory region of Cbes2105 was amplified from wild-type genomic DNA using primers DC175 and DC174. The pyrF (Cbes1377, 918 bp) coding region was amplified using primers DC173 and DC232, and joined to the fragment containing the regulatory region by OE-PCR. The DC175 and DC232 primers were engineered to contain NheI and AatII sites, respectively. The 2.9 kb DNA fragment were amplified by PCR from intermediate vector 1 using primers DC176 and DC230 to add restriction sites. The DC176 and DC230 primers were also engineered to contain NheI and AatII sites, respectively. The two linear DNA fragments were digested with NheI and AatII, and ligated to generate 4.02 kb size of intermediate vector II (FIG. 14). In the last step, a 3.65 kb DNA fragment containing the entire sequence of pBAS2 (Dam et al. (2011) Nucleic Acids Res 39: 3240-3254; Clausen et al. (2004) Plasmid 52: 131-138) were amplified by PCR using DC283 and DC284, that contained restriction sites added a KpnI site at 5' end and a XhoI site at 3' end. A 4.02 kb linear fragment was amplified from intermediate vector II using DC285 and DC286, which contain engineered restriction sites, KpnI and XhoI, respectively. The two linear DNA fragments were digested with KpnI and XhoI, and ligated to generate pDCW 89. Further details of this construction are described in FIG. 14. Plasmid pDCW129 (FIG. 18A) was generated inserting a 0.68 kb DNA fragment containing the carbohydrate binding domain (CBM) and linker region derived from celA (Cbes1867) into pDCW89. A 0.68 kb DNA fragment was amplified by PCR using the DC397 and DC398 primers and total DNA isolated from *C. bescii* as template. The 7.75 kb of backbone DNA fragment was amplified by PCR using the DC365 and DC399 and pDCW89 as template. DC397 and DC365 primers were engineered to contain a BamHI site at the end. DC398 and DC399 primers were engineered to contain an SphI site at the end. The two linear DNA fragments were digested with BamHI and SphI and ligated to generate pDCW129. Plasmid pDCW154 and pDCW155 were generated to reduce the size of pDCW89 (FIG. 15). The 4.02 kb backbone DNA fragment was amplified by PCR using primers DC081 and DC507 and pDCW89 as template. The DC081 and DC507 primers were engineered to contain KpnI and PvuII sites, respectively. To generate pDCW154, a 531 bp DNA fragment derived from pBAS2 (Dam et al. (2011) Nucleic Acids Res 39: 3240-3254; Clausen et al. (2004) Plasmid 52: 131-138) was amplified by PCR using DC505 and DC506, primers with engineered restriction sites, KpnI and PvuII, respectively. Two linear DNA fragments were digested with KpnI and PvuII, and ligated to generate pDCW154 (FIG. 15A). Plasmid pDCW155 (FIG. 15B) is identical to pDCW154 except that the 851 bp DNA fragment was replaced with the 531 bp of fragment. The 851 bp DNA fragment derived from pBAS2 (Dam et al. (2011) Nucleic Acids Res 39: 3240-3254; Clausen et al. (2004) Plasmid 52: 131-138) was amplified by PCR using DC508 and DC 506, primers with engineered restriction sites, KpnI and PvuII, respectively. This 851 bp DNA fragment was subsequently ligated into a 4.02 kb backbone DNA fragment as described for pDCW154. DNA sequences of the primers are shown in Table 7. *E. coli* strain DH5α cells were transformed by electroporation in a 2-mm-gap cuvette at 2.5 V and transformants were selected for apramycin resistance. The sequences of all plasmids were confirmed by Automatic sequencing (Macrogen, Inc.; Rockville, Md.).

Transformation of *Caldicellulosiruptor* Species.

Electrotransformation of JWCB005 and JWCH003 was performed as described (Chung et al. (2012) PLoS One 7: e43844). JWCB011 and JWCB014 were generated by transforming JWCB005 with M.CbeI methylated pDCW89 and/or pDCW129 as described and selecting for uracil prototrophy at 75° C. DNA transformation of *C. bescii* was confirmed by PCR analysis using primers DC230 and JF199 or primers DC233 and DC235, and also by back-transformation to *E. coli*. Transformation of the JWCH003 strain was performed similarly, but at 68° C. Transformation of pDCW89 into *C. hydrothermalis* was confirmed by direct plasmid DNA isolation from transformant, JWCH005. The transformation efficiencies were calculated as the number of transformant colonies per μg of DNA added and do not take into account plating efficiencies. *E. coli* strain DH5α cells were transformed by electroporation in a 2 mm gap cuvette at 2.5 V, and transformants were selected for apramycin resistance.

Assessment of Relative Copy Number, Maintenance and Stability.

*C. bescii* transformants (JWCB011) were serially subcultured every 16 hours for 5 passages in selective (without Uracil) and non-selective (supplemented with 40 μM uracil) liquid media. After each passage, cells were harvested and used to isolate total DNA. For each sample, 3 μg of total DNA was digested with 10 U of EcoRV for 6 hours at 37° C. The restriction fragments were separated by electrophoresis in a 1.0% (wt/vol) agarose gel and transferred onto nylon membranes (Roche; Madison, Wis.). Primers JF396 and JF397 were used to amplify a fragment of the pyrF coding region using JWCB005 genomic DNA as template to generate a digoxigenin (DIG)-labeled probe by random priming with DIG High Prime DNA Labeling and Detection Starter Kit I (Roche; Madison, Wis.). The membrane was incubated with probe at 42° C. and washed at 65° C. Band intensities were determined by using a Storm 840 Phospolmager (GE Healthcare; Niskayuna, N.Y.) equipped with ImageQuant v.5.4 software (Molecular Dynamics). Relative copy number was determined as the ratio of band intensity of the plasmid derived band to the chromosomal pyrF fragment. Plasmid maintenance with and without selection was inferred from the change in relative copy number over the 5 successive cultures. To assess the structural stability of the plasmid, total DNA isolated from five independent *C. bescii* transformants containing pDCW89 was used to back-transform *E. coli* for plasmid isolation and restriction digestion analysis.

Determine the Relative Copy-Number of pBAS2.

Total DNA was isolated from JWCB001 (Table 6) and treated with RNase A (Qiagen; Valencia, Calif.). qPCR experiments were carried out with an LightCycler 480 Real-Time PCR instrument (Roche; Madison, Wis.) with the LightCycler 480 SYBR Green I master mix (Roche; Madison, Wis.). The relative copy-number of pBAS 2 (Dam et al. (2011) Nucleic Acids Res 39: 3240-3254; Clausen et al. (2004) Plasmid 52: 131-138) was determined as the average of two biologically independent samples. Table 7 lists the primers used in the qPCR experiment.

TABLE 6

Strains and plasmids used in Example 3.

| Strain or plasmid | Strain and genotype/phenotype | Source |
|---|---|---|
| *Caldicellulosiruptor* | | |
| JWCB001 | *C. bescii* DSM6725 wild type (ura+/5-FOA$^S$) | DSMZ[1] |
| JWCB005 | *C. bescii* ΔpyrFA (ura−/5-FOA$^R$) | This study |
| JWCB011 | *C. bescii* JWCB005 transformed with pDCW89 (ura+/5-FOA$^S$) | This study |
| JWCB014 | *C. bescii* JWCB005 transformed with pDCW129 (ura+/5-FOA$^S$) | This study |
| JWCH003 | *C. hydrothermalis* ISCahyI insertion mutation in pyrF (ura−/5-FOA$^R$) | 2 |
| JWCH005 | JWCH003 transformed with pDCW89 (ura+/5-FOA$^S$) | This study |
| *Escherichia coli* | | |
| JW261 | DH5α containing pDCW68 (Apramycin$^R$) | 3 |
| JW292 | DH5α containing pDCW89 (Apramycin$^R$) | This study |
| JW301 | DH5α containing pDCW129 (Apramycin$^R$) | This study |
| JW319 | DH5α containing pDCW154 (Apramycin$^R$) | This study |
| JW320 | DH5α containing pDCW155 (Apramycin$^R$) | This study |
| Plasmids | | |
| pDCW68 | 6-8 copy plasmid DNA (Apramycin$^R$) | 3 |
| pDCW89 | *E. coli/Caldicellulosiruptor* species shuttle vector (Apramycin$^R$) | This study |
| pDCW129 | *E. coli/Caldicellulosiruptor* species shuttle vector (Apramycin$^R$) | This study |
| pDCW154 | 6-8 copy plasmid DNA (Apramycin$^R$) | This study |
| pDCW155 | 6-8 copy plasmid DNA (Apramycin$^R$) | This study |

[1]*German Collection of Microorganisms and Cell Cultures*
2 Chung et al. (2013) J Ind Microbiol Biotechnol: 10.1007/s10295-10013-11244-z
3 Chung et al. (2011) J Ind Microbiol Biotechnol 38: 1867-1877

TABLE 7

Primers used in Example 3.

| Primers | Sequences (5' to 3') | SEQ ID No: | Description |
|---|---|---|---|
| FJ298 F | ACCAGCCTAACTTCGATCATTGGA | 21 | amplify pyrF (Cbes1377) region |
| JH020 R | TCTGACGCTCAGTGGAACGAA | 22 | amplify pyrF (Cbes1377) region |
| DC326 F | TCTGCTAGCTCAGGTCCTGCTATAAAGCCAA | 23 | amplify pyrE (Cbes1382) region |
| DC331 R | TCACACGTACCAGAAGGCAGAC | 24 | amplify pyrE (Cbes1382) region |
| JF199 R | CGCTAACGGATTCACCACT | 25 | amplify pSC101 *E. coli* replication origin |
| DC080 F | TCATCTGTGCATATGGACAG | 26 | amplify *E. coli* features in pDCW68 |
| DC084 R | TCCAACGTCATCTCGTTCTC | 27 | amplify *E. coli* features in pDCW68 |
| DC230 F | AAGAGACGTCTCATCTGTGCATATGGACAG | 28 | construct intermediate vector II |
| DC176 R | TCTGCTAGCTCCAACGTCATCTCGTTCTC | 29 | construct intermediate vector II |
| DC175 F | AGAGCTAGCTTCAACAACCAGAGACACTTGGGA | 30 | amplify pyrF cassette |
| DC174 R | AGCCTATCAGAGAAGTTCAACAATCTAGAGACCATCCTTTCTATGTAGAAA | 31 | amplify the pyrF cassette |
| DC173 F | TTTCTACATAGAAAGGATGGTCTCTAGATTGTTGAACTTCTCTGATAGGCT | 32 | amplify the pyrF cassette |
| DC232 R | AGAGACGTCTTAAGAGATTGCTGCGTTGATA | 33 | amplify pyrF cassette |

TABLE 7-continued

Primers used in Example 3.

| Primers | Sequences (5' to 3') | SEQ ID No: | Description |
|---|---|---|---|
| DC283 F | TCTGGTACCACCGTGAGCATTCTGGACAGGT | 34 | amplify entire pBAS2 |
| DC284 R | AGACTCGAGATTCCCATGAGCCCACGAACAGT | 35 | amplify entire pBAS2 |
| DC285 F | AGACTCGAGTCTTCTGACGCTCAGTGGAACGAA | 36 | construct pDCW89 |
| DC286 R | TCTGGTACCACCAGCCTAACTTCGATCATTGGAC | 37 | construct pDCW89 |
| DC399 F | AGAGCATGCGAAAACTTGTATTTCCAGGGCCATCAC C CATCACCATCACTAATTTC | 38 | construct pDCW129 |
| DC365 R | TCTGGATCCAATCCTCCTTTTGGGATTATAACTGTC CATATGCACAGATGAGACG | 39 | construct pDCW129 |
| DC397 F | AGAGGATCCATGCAGATAAAGGTATTGTATGCTAAC AAG | 40 | construct pDCW129 |
| DC398 R | AGACAGAGGTTTATGTGGTTATGGGCATGC | 41 | construct pDCW129 |
| DC505 F | TCTGGTACCTCTTTATCTTCCATTATGAGTTTGATAG | 42 | construct pDCW154 |
| DC506 R | ACGTTAGTCAGCTGTTGTTAGTTC | 43 | construct pDCW154 and 155 |
| DC507 F | AGAAGAACAGCTGTCTGACGCTCAGTGGAACGAA | 44 | construct pDCW154 and 155 |
| DC081 R | AGAGGTACCACCAGCCTAACTTCGATCATTGGA | 45 | construct pDCW154 and 155 |
| DC508 F | TCTGGTACCAGTTCCTGCTTTGTTAACATTCCTTG | 46 | construct pDCW155 |
| JF396 F | AGTGTTCTTATAGCTGGAATTGATACGAG | 47 | produce probe within pyrF for southern analysis |
| JF397 R | AGCGTTTGAGTATCCTTTTGCAG | 48 | produce the probe within pyrF region for southern analysis |
| DC233 F | ATCCGTTGATCTTCCTGCAT | 49 | confirm the transformation of pDCW129 |
| DC255 R | AGGATCTGAGGTTCTTATGGCTC | 50 | confirm the transformation of pDCW129 |
| Q1 F | TGGGAAAGCCGTCCATAATC | 51 | qPCR primer for pBAS2 |
| Q2 R | TCTCCCGCTCTTCTCTCTTT | 52 | qPCR primer for pBAS2 |
| Q3 F | GTGCGTCTACAGGACCTTATTT | 53 | qPCR primer for pBAS2 |
| Q4 R | GGCAAGATTCTACAGGCAAGA | 54 | qPCR primer for pBAS2 |
| Q5 F | TGAGCGCCAATCAGGTATAAG | 55 | qPCR primer for chromosome (2249000-2249090) |
| Q6 R | GGAAGGGAGATAGCGGATAGA | 56 | qPCR primer for chromosome (2249000-2249090) |
| Q7 F | GCATCTGGTGGCTATGGATATT | 57 | qPCR primer for chromosome (1303164-1303201) |
| Q8 R | ACCTTTGCTCCACACCTTAC | 58 | qPCR primer for chromosome (1303164-1303201) |

Example 4

Direct Conversion of Plant Biomass to Ethanol by *Caldicellulosiruptor*

Strains, Media and Culture Conditions.

*C. bescii* strains and plasmids used in this study are listed in Table 8. All *C. bescii* strains were grown anaerobically in liquid or on solid surface in low osmolarity defined (LOD) medium (Farkas et al. (2013) J Ind Microbiol Biotechnol 40: 41-49) with maltose (0.5% wt/v; catalog no. M5895, Sigma-Aldrich; St. Louis, Mo.) as the carbon source, final pH 7.0. Liquid cultures were grown from a 0.5% inoculum or a single colony and incubated at 75° C. in anaerobic culture bottles degassed with five cycles of vacuum and argon. For growth of uracil auxotrophic mutants, the LOD medium was supplemented with 40 μM uracil. *E. coli* strain DH5α was used for plasmid DNA constructions and preparations. Standard techniques for *E. coli* were performed as described (Sambrook et al. (2001) Molecular Cloning: A Laboratory Manual: Cold Spring Harbor Laboratory Press). *E. coli* cells were grown in LB broth supplemented with apramycin (50 μg/mL) and plasmid DNA was isolated using a Qiagen Mini-prep Kit. Chromosomal DNA from *C. bescii* strains was extracted using the Quick-gDNA™ MiniPrep (Zymo Research; Irvine, Calif.) or using the DNeasy Blood & Tissue Kit (Qiagen; Valencia, Calif.) according to the manufacturer's instructions.

TABLE 8

Strains and plasmids used in Example 4.

| Strains/Plasmids | Strain and genotype/phenotype | Source |
|---|---|---|
| | *Caldicellulosiruptor bescii* | |
| JWCB001 | *C. bescii* DSMZ6725 wild type/(ura$^+$/5-FOA$^S$) | DSMZ[1] |
| JWCB018 | ΔpyrFA ldh::ISCbe4 Δcbe1/(ura$^-$/5-FOA$^R$) | 4, 5 |
| JWCB032 | ΔpyrFA ldh::ISCbe4 Δcbe1::P$_{S-layer}$ Cthe-adhE[2]/ (ura$^-$/5-FOA$^R$) | This study |
| JWCB033 | ΔpyrFA ldh::ISCbe4 Δcbe1::P$_{S-layer}$ Cthe-adhE* [3]/ (ura$^-$/5-FOA$^R$) | This study |
| | Plasmids | |
| pDCW88 | cbeI knock-out vector (Apramycin$^R$) | 4 |
| pDCW139 | 6-8 copy plasmid DNA (Apramycin$^R$) | This study |
| pDCW140 | 6-8 copy plasmid DNA (Apramycin$^R$) | This study |
| pDCW142 | 6-8 copy plasmid DNA/Back-bone plasmid for knock-in vector (Apramycin$^R$) | This study |
| pDCW144 | Knock-in plasmid containing P$_{S-layer}$ Cthe-adhE[2] expression cassette | This study |
| pDCW145 | Knock-in plasmid containing P$_{S-layer}$ Cthe-adhE*[3] expression cassette | This study |

[1] German Collection of Microorganisms and Cell Cultures
[2] Cthe-athE (Cthe0423; Bifunctional acetaldehyde-CoA/alcohol dehydrogenase derived from *Clostridium thermocellum* ATCC27405)
[3] Cthe-athE (EA: Bifunctional acetaldehyde-CoA/alcohol dehydrogenase derived from *Clostridium thermocellum* EtOH)(Brown et al. (2011) Proc Natl Acad Sci USA 108: 13752-13757)
4 Chung et al. (2013) Biotechnol Biofuels 6: 82 (Example 2)
5 Cha et al. (2013) "Isolation and Bioinformatic Analysis of a Novel Transposable Element, ISCbe4, from a Hyperthermophilic Bacterium, *Caldicellulosiruptor bescii*" JIMB submitted Constructions of Vectors for Knock-in of the Cthe0423 and its Derivative into *C. bescii*.

The plasmids described below were generated using high fidelity pfu AD DNA polymerase (Agilent Technologies; Santa Clara, Calif.) for PCR reactions, restriction enzymes (New England Biolabs; Ipswich, Mass.), and Fast-link DNA Ligase kit (Epicentre Biotechnologies; Madison, Wis.) according to the manufacturer's instructions. Plasmid pDCW144 (FIG. 20A, FIG. 19) was constructed in four cloning steps. First, a 2.31 kb DNA fragment containing the targeted insertion region sequences (intergenic space between convergent coding regions Cbes0863-Cbes0864) in *C. bescii* chromosome was amplified using primers DC456 (with KpnI site) and DC457 (with EcoRI site) using *C. bescii* genomic DNA as a template. The 4.0 kb DNA fragments containing a apramycin resistance cassette, pyrF cassette (Example 3), and the pSC101 replication origin, were amplified from pDCW88 (Example 2) using primers DC081 and DC356. The DC081 and DC356 primers were engineered to contain KpnI and EcoRI sites, respectively. These two linear DNA fragments were digested with KpnI and EcoRI, and ligated to construct 6.33 kb size of pDCW139 (FIG. 19). Plasmid pDCW140 (FIG. 19) was constructed by inserting the 3.28 kb of DNA fragment, which contains the 134 bp of upstream sequences of Cbes2303 (S-layer protein), 3,507 bp of Cbes2303 coding sequences, and 86 bp of its downstream sequences, into the pDCW139. This DNA fragment was amplified using primers DC460 (with PvuI site) and DC461 (with NotI site) using *C. bescii* genomic DNA as a template. The 6.1 kb DNA fragment was amplified from pDCW139 using primers DC458 (with PvuI site) and DC459 (with NotI site) to be used as a back-bone fragment. These two linear DNA fragments were digested with PvuI and NotI, and ligated to construct 9.3 kb size of pDCW140. Resulting plasmid is containing the 5' flanking region (1,013 bp) and the 3' flanking region (1,012 bp) of targeted insertion site in *C. bescii* genome in addition to S-layer protein expression cassette (FIG. 19). Plasmid pDCW142, back-bone vector for knock-in plasmid, was constructed by adding restriction sites for cloning and C-terminal 6× Histidine-tag in front of stop codon, in addition to removing the Cbes2303 coding sequences in pDCW140. The 6.3 kb DNA fragment was amplified from pDCW139 using primers DC464 (with BamHI site) and DC466 (with SphI site, 6× Histidine-tag, and stop codon) using pDCW140 as a template. This DNA fragment was blunt-end ligated after treatment with T4 PNK (New England Biolabs; Ipswich, Mass.) to construct pDCW142 (FIG. 19). In the last step, a 2.62 kb DNA fragment containing the coding sequence of Cthe0423 were amplified by PCR using DC469 (with BamHI site) and DC470 (with SphI site) using *Clostridium thermocellum* ATCC 27405 genomic DNA as a template. This DNA fragment was digested with BamHI and SphI, and then cloned into pDCW142 that had been digested with BamHI and SphI (FIG. 19). Plasmid pDCW145 is identical to pDCW144 except for the cloning of Cthe0423* (Brown et al. (2011) Proc Natl Acad Sci USA 108: 13752-13757), which containing two point mutations in coding sequences, into pDCW142. To make this change, a 2.62 kb DNA fragment containing the coding sequence of Cthe0423* were amplified by PCR using DC469 (with BamHI site) and DC470 (with SphI site) using *Clostridium thermocellum* EtOH (Brown et al. (2011) Proc Natl Acad Sci USA 108: 13752-13757) genomic DNA as a template. DNA sequences of the primers are shown in Table 9. *E. coli* strain DH5α cells were transformed by electroporation in a 2-mm-gap cuvette at 2.5 V and transfonnants were selected for apramycin resistance. The sequences of all plasmids were verified by Automatic sequencing (Macrogen, Inc.; Rockville, Md.).

Transformation, Screening, Purification, and Sequence Verification of Engineered *C. bescii* mutants.

To construct strain JWCB032, one microgram of pDCW144 DNA was used to electrotransform JWCB018 (ΔpyrFA ΔcbeI) as described (Example 2). Cells were then plated onto solid LOD medium and uracil prototrophic transformant colonies were inoculated into liquid medium for genomic DNA extraction and subsequent PCR screening of the targeted region to confirm the knock-in event of pDCW144 into the chromosome. Confirmed transformants were inoculated into nonselective liquid defined medium, with 40 µM uracil, and incubated overnight at 75° C. to allow loop-out of the plasmid. The cultures were then plated onto 5-FOA (8 mM) containing solid medium. After initial screening, transformants containing the expected knock-in were further purified by one additional passage under selection on solid medium and screened a second time by PCR to check for segregation of the P$_{S-layer}$-adhE insertion. The location of the insertion was verified by PCR amplification and sequence analysis. A PCR product was generated from genomic DNA using primers (DC477 and DC478) outside the homologous regions used to construct the knock-in, and internal primers (DC456, DC457, DC462 and DC463). PCR products were sequenced to confirm Construction of JWCB033 was the same as JWCB032 except that pDCW145 was used to electrotransform JWCB018. All primers used are listed in Table 9.

TABLE 9

Primers used in Example 4.

| Primer | Sequences (5' to 3') | SEQ ID No | Description |
|---|---|---|---|
| DC081 | TCCAATGATCGAAGTTAGGCTGGT | 59 | construct pDCW139 |
| DC356 | TCTGAATTCTCTGACGCTCAGTGGAACGAA | 60 | construct pDCW139 |
| DC456 | AGAGGTACCTGTGAGGGCATGTCAATTTACGA | 61 | construct pDCW139 |
| DC457 | AGAGAATTCTCTTTTCGATGGAATCTTCTTCGGA | 62 | construct pDCW139 |
| DC458 | AGAGAGCGATCGTCTATTGTAACTTTCACTTCAGTGCA | 63 | construct pDCW140 |
| DC459 | AGAAGAAGGCGGCCGCTGGAAGAACTTGAAAGCAGGCT | 64 | construct pDCW140 |
| DC460 | AGAGAGCGATCGACAGTTTGATTACAGTTTAGTCAGAGCT | 65 | construct pDCW140 |
| DC461 | AGAAGAAGGCGGCCGCTTGGTTCCTTAAATCTAAGAGGTATGA | 66 | construct pDCW140 |
| DC462 | TGCTGGCAGAGAAGAGCGAAA | 67 | Sequencing pDCW140 |
| DC463 | TCTTCATCCCAATCTTCAACTTC | 68 | Sequencing pDCW140 |
| DC464 | ACTGGATCCCTCACCAAACCTCCTTGTATGAT | 69 | construct pDCW142 |
| DC466 | AGAGCATGCCATCACCATCACCATCACTAATAATAAAGCTGAAATAAAAGAGGGTGAGA | 70 | construct pDCW142 |
| DC469 | ACTGGATCCATGACGAAAATAGCGAATAAATACGAAGT | 71 | construct pDCW144 and 145 |
| DC470 | AGAGCATGCTTTCTTCGCACCTCCGTAATAAGCGTTCAGA | 72 | construct pDCW144 and 145 |
| DC471 | TGGTAATGAGAGAAGCAGATG | 73 | Sequencing pDCW144 and 145 |
| DC472 | TGATAAAAGCACCCAGTTTGT | 74 | Sequencing pDCW144 and 145 |
| DC477 | TGGTTGACCAGGAGAATTTTACACA | 75 | verify insertion |
| DC478 | AGCAACAATCCTGCATTTGTAAG | 76 | verify insertion |

Preparation of Cell Lysates and Western Blotting.

A cell-free extracts of *C. bescii* were prepared from 500 ml cultures grown to mid-log phase at various temperatures (60° C., 65° C., 70° C., and 75° C.), harvested by centrifugation at 6,000×g at 4° C. for 15 min and resuspended in Cel-Lytic B cell lysis reagent (Sigma-Aldrich; St. Louis, Mo.). Cells were lysed by a combination of 4× freeze-thawing and sonication on ice. Protein concentrations were determined using the Bio-Rad protein assay kit with bovine serum albumin (BSA) as the standard. 77 microgram protein samples were electrophoresed in a 4-15% gradient Mini-Protean TGX gels (Bio-Rad Laboratories; Hercules, Calif.) and electrotransferred to PVDF membranes (Immobilon™-P; Millipore; Billerica, Mass.) using a Bio-Rad Mini-Protean 3 electrophoretic apparatus. The membranes were then probed with His-tag (6×His) monoclonal antibody (1:5000 dilution; Invitrogen; Grand Island, N.Y.) using the ECL Western Blotting substrate Kit (Thermo Scientific; Waltham, Mass.) as specified by the manufacturer.

Growth Curve Analysis, Measurement of Ethanol Tolerance, and Fermentation Conditions.

Analysis of growth and ethanol tolerance was conducted in stoppered 125 ml serum bottles containing 50 ml LOD medium supplemented with 10 g/l cellobiose (catalog no.M5895, Sigma-Aldrich; St. Louis, Mo.) and 1 mM uracil. Duplicate bottles were inoculated with a fresh 2% (v/v) inoculum and incubated at both 65° C. and 75° C. with shaking at 150 rpm. Optical cell density was monitored using a Jenway Genova spectrophotometer, measuring absorbance at 680 nm. Batch fermentations were performed for 5 days in the same culture conditions except using 10 g/l cellobiose, 20 g/l AVICEL (catalog no. 11365, Fluka), or 10 g/l unpretreated switchgrass (sieved −20/+80-mesh fraction; Brian Davison, Oak Ridge National Laboratory, Oak Ridge, Tenn.) as carbon sources.

Analytical Techniques for Determining Fermentation End Products.

Fermentation products, acetate, lactate and ethanol, were analyzed on an Agilent 1200 infinity high-performance liquid chromatography (HPLC) system (Agilent Technologies; Santa Clara, Calif.). Metabolites were separated on an Aminex HPX-87H column (Bio-Rad Laboratories; Hercules, Calif.) under isocratic temperature (50° C.) and a flow (0.6 ml/min) condition in 5.0 mM $H_2SO_4$ and then passed through a refractive index (RI) detector (Agilent 1200 Infinity Refractive Index Detector). Identification was performed by comparison of retention times with standards, and total peak areas were integrated and compared against peak areas and retention times of known standards for each interest.

The complete disclosure of all patents, patent applications, and publications, and electronically available material (including, for instance, nucleotide sequence submissions in, e.g., GenBank and RefSeq, and amino acid sequence submissions in, e.g., SwissProt, PIR, PRF, PDB, and translations from annotated coding regions in GenBank and RefSeq) cited herein are incorporated by reference in their entirety. In the event that any inconsistency exists between the disclosure of the present application and the disclosure(s) of any document incorporated herein by reference, the disclosure of the present application shall govern. The foregoing detailed description is provided for clarity of understanding only. No unnecessary limitations are to be understood therefrom. The invention is not limited to the exact details shown and described, for variations obvious to one skilled in the art will be included within the invention defined by the claims.

The term "and/or" means one or all of the listed elements or a combination of any two or more of the listed elements; the terms "comprises" and variations thereof do not have a limiting meaning where these terms appear in the description and claims; unless otherwise specified, "a," "an," "the," and "at least one" are used interchangeably and mean one or more than one; and the recitations of numerical ranges by endpoints include all numbers subsumed within that range (e.g., 1 to 5 includes 1, 1.5, 2, 2.75, 3, 3.80, 4, 5, etc.).

Unless otherwise indicated, all numbers expressing quantities of components, molecular weights, and so forth used in the specification and claims are to be understood as being modified in all instances by the term "about." Accordingly, unless otherwise indicated to the contrary, the numerical parameters set forth in the specification and claims are approximations that may vary depending upon the desired properties sought to be obtained by the present invention. At the very least, and not as an attempt to limit the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. All numerical values, however, inherently contain a range necessarily resulting from the standard deviation found in their respective testing measurements.

All headings are for the convenience of the reader and should not be used to limit the meaning of the text that follows the heading, unless so specified.

What is claimed is:

1. A recombinant *Caldicellulosiruptor* microbe genetically modified to produce a greater amount of ethanol than a comparable wild type control, wherein the *Caldicellulosiruptor* microbe:

comprises a knock-out of the coding region of a lactate dehydrogenase and produces lactate in an amount less than a comparable wild type control;

comprises at least one heterologous polynucleotide that encodes an enzyme in a metabolic pathway that converts acetyl-CoA to ethanol, wherein the enzyme is an acetaldehyde dehydrogenase that can convert acetyl-CoA to acetaldehyde, an aldehyde dehydrogenase that can convert acetyl-CoA to acetaldehyde, or a combination thereof; and wherein the *Caldicellulosiruptor* microbe is *C. bescii, C. kristjansonii, C. obsidiansis, C. hydro-*

*thermalis, C. kronotskvensis, C. lactoaceticus,* or *C. saccharolvticus.*

2. The recombinant *Caldicellulosiruptor* microbe of claim 1 wherein the *Caldicellulosiruptor* microbe is *Caldicellulosiruptor bescii.*

3. The recombinant *Caldicellulosiruptor* microbe of claim 1 comprising a deletion of at least a portion of a lactate dehydrogenase coding region.

4. The recombinant *Caldicellulosiruptor* microbe of claim 3 wherein the lactate dehydrogenase coding region encodes an NADH-dependent lactate dehydrogenase (Cbes 1918).

5. The recombinant *Caldicellulosiruptor* microbe of claim 1 further genetically modified to exhibit decreased activity of an endonuclease that digests unmethylated DNA in a *Caldicellulosiruptor* spp. (CbeI) compared to a comparable wild-type control.

6. The recombinant *Caldicellulosiruptor* microbe of claim 1 further genetically modified to exhibit increased efficiency of transformation with unmethylated heterologous DNA.

7. A method comprising:
    growing the recombinant *Caldicellulosiruptor* microbe of claim 1, wherein the *Caldicellulosiruptor* microbe is genetically modified to produce a greater amount of ethanol than a comparable wild type control under conditions effective for the recombinant *Caldicellulosiruptor* microbe to produce ethanol, wherein the *Caldicellulosiruptor* microbe:
    comprises a knock-out of the coding region of a lactate dehydrogenase and produces lactate in an amount less than a comparable wild type control;
    comprises at least one heterologous polynucleotide that encodes an enzyme in a metabolic pathway that converts acetyl-CoA to ethanol, wherein the enzyme is an acetaldehyde dehydrogenase that can convert acetate to acetaldehyde, an aldehyde dehydrogenase that can convert acetyl-CoA to acetaldehyde, or a combination thereof;
    and wherein the
*Caldicellulosiruptor* microbe is *C. bescii, C. kristjansonii, C. obsidiansis, C. hydrothermalis, C. kronotskvensis, C. lactoaceticus,* or *C. saccharolvticus.*

8. The method of claim 7 further comprising collecting at least a portion of the ethanol.

9. The method of claim 7 wherein the conditions comprise a carbon source that comprises napier grass, Bermuda grass, switchgrass, or a hardwood.

10. The method of claim 9 wherein the carbon source comprises unpretreated switchgrass.

11. The recombinant *Caldicellulosiruptor* microbe of claim 1 further comprising a knock-out of the coding region of an acetate kinase where the microbe further comprises an alcohol dehydrogenase that converts acetaldehyde to ethanol.

* * * * *

SEQUENCE LISTING

<160> NUMBER OF SEQ ID NOS: 76

<210> SEQ ID NO 1
<211> LENGTH: 24
<212> TYPE: DNA
<213> ORGANISM: artificial
<220> FEATURE:
<223> OTHER INFORMATION: synthetic oligonucleotide primer

<400> SEQUENCE: 1
tccaatgatc gaagttaggc tggt                                        24

<210> SEQ ID NO 2
<211> LENGTH: 27
<212> TYPE: DNA
<213> ORGANISM: artificial
<220> FEATURE:
<223> OTHER INFORMATION: synthetic oligonucleotide primer

<400> SEQUENCE: 2
gaattctctg acgctcagtg gaacgaa                                     27

<210> SEQ ID NO 3
<211> LENGTH: 34
<212> TYPE: DNA
<213> ORGANISM: artificial
<220> FEATURE:
<223> OTHER INFORMATION: synthetic oligonucleotide primer

<400> SEQUENCE: 3
gaaaacaaat gggcttggga ggataggagg ctgt                             34

<210> SEQ ID NO 4
<211> LENGTH: 35
<212> TYPE: DNA
<213> ORGANISM: artificial
<220> FEATURE:
<223> OTHER INFORMATION: synthetic oligonucleotide primer

<400> SEQUENCE: 4
tgggcttggg aggataggag gctgtctaaa aacaa                            35

<210> SEQ ID NO 5
<211> LENGTH: 23
<212> TYPE: DNA
<213> ORGANISM: artificial

<220> FEATURE:
<223> OTHER INFORMATION: synthetic oligonucleotide primer

<400> SEQUENCE: 5
tgccaagata tgaaatgaga act                                           23

<210> SEQ ID NO 6
<211> LENGTH: 52
<212> TYPE: DNA
<213> ORGANISM: artificial
<220> FEATURE:
<223> OTHER INFORMATION: synthetic oligonucleotide primer

<400> SEQUENCE: 6
cgtctcatct gtgcatatgg acagttataa tcccaaaagg aggattggat cc           52

<210> SEQ ID NO 7
<211> LENGTH: 23
<212> TYPE: DNA
<213> ORGANISM: artificial
<220> FEATURE:
<223> OTHER INFORMATION: synthetic oligonucleotide primer

<400> SEQUENCE: 7
tctacactct tgcttacaca ggt                                           23

<210> SEQ ID NO 8
<211> LENGTH: 31
<212> TYPE: DNA
<213> ORGANISM: artificial
<220> FEATURE:
<223> OTHER INFORMATION: synthetic oligonucleotide primer

<400> SEQUENCE: 8
tctcctcgag cagaccaagt gcgtattttt c                                  31

<210> SEQ ID NO 9
<211> LENGTH: 32
<212> TYPE: DNA
<213> ORGANISM: artificial
<220> FEATURE:
<223> OTHER INFORMATION: synthetic oligonucleotide primer

<400> SEQUENCE: 9
agagaggtac ctgcaacatc cggcttaatg ac                                 32

<210> SEQ ID NO 10
<211> LENGTH: 46
<212> TYPE: DNA
<213> ORGANISM: artificial
<220> FEATURE:
<223> OTHER INFORMATION: synthetic oligonucleotide primer

<400> SEQUENCE: 10
tgttaaaacc acctacctaa tcttatcatg ttggaaggca aattga                  46

<210> SEQ ID NO 11
<211> LENGTH: 23
<212> TYPE: DNA
<213> ORGANISM: artificial
<220> FEATURE:
<223> OTHER INFORMATION: synthetic oligonucleotide primer

<400> SEQUENCE: 11
agattaggta ggtggtttta aca                                           23

<210> SEQ ID NO 12
<211> LENGTH: 34
<212> TYPE: DNA
<213> ORGANISM: artificial
<220> FEATURE:
<223> OTHER INFORMATION: synthetic oligonucleotide primer

<400> SEQUENCE: 12
tgtgtggtgc actccttgat aatttcagct gcct                                34

<210> SEQ ID NO 13
<211> LENGTH: 33
<212> TYPE: DNA
<213> ORGANISM: artificial
<220> FEATURE:
<223> OTHER INFORMATION: synthetic oligonucleotide primer

<400> SEQUENCE: 13
tgtgtggtgc actctgacgc tcagtggaac gaa                                 33

<210> SEQ ID NO 14
<211> LENGTH: 35
<212> TYPE: DNA
<213> ORGANISM: artificial
<220> FEATURE:
<223> OTHER INFORMATION: synthetic oligonucleotide primer

<400> SEQUENCE: 14
agagaggtac caccagccta acttcgatca ttgga                               35

<210> SEQ ID NO 15
<211> LENGTH: 27
<212> TYPE: DNA
<213> ORGANISM: artificial
<220> FEATURE:
<223> OTHER INFORMATION: synthetic oligonucleotide primer

<400> SEQUENCE: 15
aggtaccggt tcatgtgcag ctccatc                                        27

<210> SEQ ID NO 16
<211> LENGTH: 21
<212> TYPE: DNA
<213> ORGANISM: artificial
<220> FEATURE:
<223> OTHER INFORMATION: synthetic oligonucleotide primer

<400> SEQUENCE: 16
ctccaacgtc atctcgttct c                                              21

<210> SEQ ID NO 17
<211> LENGTH: 23
<212> TYPE: DNA
<213> ORGANISM: artificial
<220> FEATURE:
<223> OTHER INFORMATION: synthetic oligonucleotide primer

<400> SEQUENCE: 17
tagtcttgat gcttcactga tag                                            23

<210> SEQ ID NO 18
<211> LENGTH: 19
<212> TYPE: DNA
<213> ORGANISM: artificial
<220> FEATURE:
<223> OTHER INFORMATION: synthetic oligonucleotide primer

```
<400> SEQUENCE: 18
cgctaacgga ttcaccact                                                    19

<210> SEQ ID NO 19
<211> LENGTH: 20
<212> TYPE: DNA
<213> ORGANISM: artificial
<220> FEATURE:
<223> OTHER INFORMATION: synthetic oligonucleotide primer

<400> SEQUENCE: 19
atccgttgat cttcctgcat                                                   20

<210> SEQ ID NO 20
<211> LENGTH: 23
<212> TYPE: DNA
<213> ORGANISM: artificial
<220> FEATURE:
<223> OTHER INFORMATION: synthetic oligonucleotide primer

<400> SEQUENCE: 20
aggatctgag gttcttatgg ctc                                               23

<210> SEQ ID NO 21
<211> LENGTH: 24
<212> TYPE: DNA
<213> ORGANISM: artificial
<220> FEATURE:
<223> OTHER INFORMATION: synthetic oligonucleotide primer

<400> SEQUENCE: 21
accagcctaa cttcgatcat tgga                                              24

<210> SEQ ID NO 22
<211> LENGTH: 21
<212> TYPE: DNA
<213> ORGANISM: artificial
<220> FEATURE:
<223> OTHER INFORMATION: synthetic oligonucleotide primer

<400> SEQUENCE: 22
tctgacgctc agtggaacga a                                                 21

<210> SEQ ID NO 23
<211> LENGTH: 31
<212> TYPE: DNA
<213> ORGANISM: artificial
<220> FEATURE:
<223> OTHER INFORMATION: synthetic oligonucleotide primer

<400> SEQUENCE: 23
tctgctagct caggtcctgc tataaagcca a                                      31

<210> SEQ ID NO 24
<211> LENGTH: 22
<212> TYPE: DNA
<213> ORGANISM: artificial
<220> FEATURE:
<223> OTHER INFORMATION: synthetic oligonucleotide primer

<400> SEQUENCE: 24
tcacacgtac cagaaggcag ac                                                22

<210> SEQ ID NO 25
```

```
<211> LENGTH: 19
<212> TYPE: DNA
<213> ORGANISM: artificial
<220> FEATURE:
<223> OTHER INFORMATION: synthetic oligonucleotide primer

<400> SEQUENCE: 25
cgctaacgga ttcaccact                                               19

<210> SEQ ID NO 26
<211> LENGTH: 20
<212> TYPE: DNA
<213> ORGANISM: artificial
<220> FEATURE:
<223> OTHER INFORMATION: synthetic oligonucleotide primer

<400> SEQUENCE: 26
tcatctgtgc atatggacag                                              20

<210> SEQ ID NO 27
<211> LENGTH: 20
<212> TYPE: DNA
<213> ORGANISM: artificial
<220> FEATURE:
<223> OTHER INFORMATION: synthetic oligonucleotide primer

<400> SEQUENCE: 27
tccaacgtca tctcgttctc                                              20

<210> SEQ ID NO 28
<211> LENGTH: 30
<212> TYPE: DNA
<213> ORGANISM: artificial
<220> FEATURE:
<223> OTHER INFORMATION: synthetic oligonucleotide primer

<400> SEQUENCE: 28
aagagacgtc tcatctgtgc atatggacag                                   30

<210> SEQ ID NO 29
<211> LENGTH: 29
<212> TYPE: DNA
<213> ORGANISM: artificial
<220> FEATURE:
<223> OTHER INFORMATION: synthetic oligonucleotide primer

<400> SEQUENCE: 29
tctgctagct ccaacgtcat ctcgttctc                                    29

<210> SEQ ID NO 30
<211> LENGTH: 33
<212> TYPE: DNA
<213> ORGANISM: artificial
<220> FEATURE:
<223> OTHER INFORMATION: synthetic oligonucleotide primer

<400> SEQUENCE: 30
agagctagct tcaacaacca gagacacttg gga                               33

<210> SEQ ID NO 31
<211> LENGTH: 51
<212> TYPE: DNA
<213> ORGANISM: artificial
<220> FEATURE:
<223> OTHER INFORMATION: synthetic oligonucleotide primer

<400> SEQUENCE: 31
```
agcctatcag agaagttcaa caatctagag accatccttt ctatgtagaa a        51

<210> SEQ ID NO 32
<211> LENGTH: 51
<212> TYPE: DNA
<213> ORGANISM: artificial
<220> FEATURE:
<223> OTHER INFORMATION: synthetic oligonucleotide primer

<400> SEQUENCE: 32
tttctacata gaaaggatgg tctctagatt gttgaacttc tctgataggc t        51

<210> SEQ ID NO 33
<211> LENGTH: 31
<212> TYPE: DNA
<213> ORGANISM: artificial
<220> FEATURE:
<223> OTHER INFORMATION: synthetic oligonucleotide primer

<400> SEQUENCE: 33
agagacgtct taagagattg ctgcgttgat a                              31

<210> SEQ ID NO 34
<211> LENGTH: 31
<212> TYPE: DNA
<213> ORGANISM: artificial
<220> FEATURE:
<223> OTHER INFORMATION: synthetic oligonucleotide primer

<400> SEQUENCE: 34
tctggtacca ccgtgagcat tctggacagg t                              31

<210> SEQ ID NO 35
<211> LENGTH: 32
<212> TYPE: DNA
<213> ORGANISM: artificial
<220> FEATURE:
<223> OTHER INFORMATION: synthetic oligonucleotide primer

<400> SEQUENCE: 35
agactcgaga ttcccatgag cccacgaaca gt                             32

<210> SEQ ID NO 36
<211> LENGTH: 33
<212> TYPE: DNA
<213> ORGANISM: artificial
<220> FEATURE:
<223> OTHER INFORMATION: synthetic oligonucleotide primer

<400> SEQUENCE: 36
agactcgagt cttctgacgc tcagtggaac gaa                            33

<210> SEQ ID NO 37
<211> LENGTH: 34
<212> TYPE: DNA
<213> ORGANISM: artificial
<220> FEATURE:
<223> OTHER INFORMATION: synthetic oligonucleotide primer

<400> SEQUENCE: 37
tctggtacca ccagcctaac ttcgatcatt ggac                           34

<210> SEQ ID NO 38
<211> LENGTH: 56
<212> TYPE: DNA

```
<213> ORGANISM: artificial
<220> FEATURE:
<223> OTHER INFORMATION: synthetic oligonucleotide primer

<400> SEQUENCE: 38
agagcatgcg aaaacttgta tttccagggc catcaccatc accatcacta atttcc        56

<210> SEQ ID NO 39
<211> LENGTH: 55
<212> TYPE: DNA
<213> ORGANISM: artificial
<220> FEATURE:
<223> OTHER INFORMATION: synthetic oligonucleotide primer

<400> SEQUENCE: 39
tctggatcca atcctccttt tgggattata actgtccata tgcacagatg agacg         55

<210> SEQ ID NO 40
<211> LENGTH: 39
<212> TYPE: DNA
<213> ORGANISM: artificial
<220> FEATURE:
<223> OTHER INFORMATION: synthetic oligonucleotide primer

<400> SEQUENCE: 40
agaggatcca tgcagataaa ggtattgtat gctaacaag                           39

<210> SEQ ID NO 41
<211> LENGTH: 30
<212> TYPE: DNA
<213> ORGANISM: artificial
<220> FEATURE:
<223> OTHER INFORMATION: synthetic oligonucleotide primer

<400> SEQUENCE: 41
agacagaggt ttatgtggtt atgggcatgc                                     30

<210> SEQ ID NO 42
<211> LENGTH: 37
<212> TYPE: DNA
<213> ORGANISM: artificial
<220> FEATURE:
<223> OTHER INFORMATION: synthetic oligonucleotide primer

<400> SEQUENCE: 42
tctggtacct ctttatcttc cattatgagt ttgatag                             37

<210> SEQ ID NO 43
<211> LENGTH: 24
<212> TYPE: DNA
<213> ORGANISM: artificial
<220> FEATURE:
<223> OTHER INFORMATION: synthetic oligonucleotide primer

<400> SEQUENCE: 43
acgttagtca gctgttgtta gttc                                           24

<210> SEQ ID NO 44
<211> LENGTH: 34
<212> TYPE: DNA
<213> ORGANISM: artificial
<220> FEATURE:
<223> OTHER INFORMATION: synthetic oligonucleotide primer

<400> SEQUENCE: 44
agaagaacag ctgtctgacg ctcagtggaa cgaa                                34
```

<210> SEQ ID NO 45
<211> LENGTH: 33
<212> TYPE: DNA
<213> ORGANISM: artificial
<220> FEATURE:
<223> OTHER INFORMATION: synthetic oligonucleotide primer

<400> SEQUENCE: 45
agaggtacca ccagcctaac ttcgatcatt gga                          33

<210> SEQ ID NO 46
<211> LENGTH: 35
<212> TYPE: DNA
<213> ORGANISM: artificial
<220> FEATURE:
<223> OTHER INFORMATION: synthetic oligonucleotide primer

<400> SEQUENCE: 46
tctggtacca gttcctgctt tgttaacatt ccttg                        35

<210> SEQ ID NO 47
<211> LENGTH: 29
<212> TYPE: DNA
<213> ORGANISM: artificial
<220> FEATURE:
<223> OTHER INFORMATION: synthetic oligonucleotide primer

<400> SEQUENCE: 47
agtgttctta tagctggaat tgatacgag                               29

<210> SEQ ID NO 48
<211> LENGTH: 23
<212> TYPE: DNA
<213> ORGANISM: artificial
<220> FEATURE:
<223> OTHER INFORMATION: synthetic oligonucleotide primer

<400> SEQUENCE: 48
agcgtttgag tatcctttg cag                                      23

<210> SEQ ID NO 49
<211> LENGTH: 20
<212> TYPE: DNA
<213> ORGANISM: artificial
<220> FEATURE:
<223> OTHER INFORMATION: synthetic oligonucleotide primer

<400> SEQUENCE: 49
atccgttgat cttcctgcat                                         20

<210> SEQ ID NO 50
<211> LENGTH: 23
<212> TYPE: DNA
<213> ORGANISM: artificial
<220> FEATURE:
<223> OTHER INFORMATION: synthetic oligonucleotide primer

<400> SEQUENCE: 50
aggatctgag gttcttatgg ctc                                     23

<210> SEQ ID NO 51
<211> LENGTH: 20
<212> TYPE: DNA
<213> ORGANISM: artificial
<220> FEATURE:

```
<223> OTHER INFORMATION: synthetic oligonucleotide primer

<400> SEQUENCE: 51
tgggaaagcc gtccataatc                                                    20

<210> SEQ ID NO 52
<211> LENGTH: 20
<212> TYPE: DNA
<213> ORGANISM: artificial
<220> FEATURE:
<223> OTHER INFORMATION: synthetic oligonucleotide primer

<400> SEQUENCE: 52
tctcccgctc ttctctcttt                                                    20

<210> SEQ ID NO 53
<211> LENGTH: 22
<212> TYPE: DNA
<213> ORGANISM: artificial
<220> FEATURE:
<223> OTHER INFORMATION: synthetic oligonucleotide primer

<400> SEQUENCE: 53
gtgcgtctac aggaccttat tt                                                 22

<210> SEQ ID NO 54
<211> LENGTH: 21
<212> TYPE: DNA
<213> ORGANISM: artificial
<220> FEATURE:
<223> OTHER INFORMATION: synthetic oligonucleotide primer

<400> SEQUENCE: 54
ggcaagattc tacaggcaag a                                                  21

<210> SEQ ID NO 55
<211> LENGTH: 21
<212> TYPE: DNA
<213> ORGANISM: artificial
<220> FEATURE:
<223> OTHER INFORMATION: synthetic oligonucleotide primer

<400> SEQUENCE: 55
tgagcgccaa tcaggtataa g                                                  21

<210> SEQ ID NO 56
<211> LENGTH: 21
<212> TYPE: DNA
<213> ORGANISM: artificial
<220> FEATURE:
<223> OTHER INFORMATION: synthetic oligonucleotide primer

<400> SEQUENCE: 56
ggaagggaga tagcggatag a                                                  21

<210> SEQ ID NO 57
<211> LENGTH: 22
<212> TYPE: DNA
<213> ORGANISM: artificial
<220> FEATURE:
<223> OTHER INFORMATION: synthetic oligonucleotide primer

<400> SEQUENCE: 57
gcatctggtg gctatggata tt                                                 22
```

```
<210> SEQ ID NO 58
<211> LENGTH: 20
<212> TYPE: DNA
<213> ORGANISM: artificial
<220> FEATURE:
<223> OTHER INFORMATION: synthetic oligonucleotide primer

<400> SEQUENCE: 58
acctttgctc cacaccttac                                               20

<210> SEQ ID NO 59
<211> LENGTH: 24
<212> TYPE: DNA
<213> ORGANISM: artificial
<220> FEATURE:
<223> OTHER INFORMATION: synthetic oligonucleotide primer

<400> SEQUENCE: 59
tccaatgatc gaagttaggc tggt                                          24

<210> SEQ ID NO 60
<211> LENGTH: 30
<212> TYPE: DNA
<213> ORGANISM: artificial
<220> FEATURE:
<223> OTHER INFORMATION: synthetic oligonucleotide primer

<400> SEQUENCE: 60
tctgaattct ctgacgctca gtggaacgaa                                    30

<210> SEQ ID NO 61
<211> LENGTH: 32
<212> TYPE: DNA
<213> ORGANISM: artificial
<220> FEATURE:
<223> OTHER INFORMATION: synthetic oligonucleotide primer

<400> SEQUENCE: 61
agaggtacct gtgagggcat gtcaatttac ga                                 32

<210> SEQ ID NO 62
<211> LENGTH: 34
<212> TYPE: DNA
<213> ORGANISM: artificial
<220> FEATURE:
<223> OTHER INFORMATION: synthetic oligonucleotide primer

<400> SEQUENCE: 62
agagaattct cttttcgatg gaatcttctt cgga                               34

<210> SEQ ID NO 63
<211> LENGTH: 38
<212> TYPE: DNA
<213> ORGANISM: artificial
<220> FEATURE:
<223> OTHER INFORMATION: synthetic oligonucleotide primer

<400> SEQUENCE: 63
agagagcgat cgtctattgt aactttcact tcagtgca                           38

<210> SEQ ID NO 64
<211> LENGTH: 38
<212> TYPE: DNA
<213> ORGANISM: artificial
<220> FEATURE:
<223> OTHER INFORMATION: synthetic oligonucleotide primer
```

<400> SEQUENCE: 64
agaagaaggc ggccgctgga agaacttgaa agcaggct                                38

<210> SEQ ID NO 65
<211> LENGTH: 40
<212> TYPE: DNA
<213> ORGANISM: artificial
<220> FEATURE:
<223> OTHER INFORMATION: synthetic oligonucleotide primer

<400> SEQUENCE: 65
agagagcgat cgacagtttg attacagttt agtcagagct                              40

<210> SEQ ID NO 66
<211> LENGTH: 43
<212> TYPE: DNA
<213> ORGANISM: artificial
<220> FEATURE:
<223> OTHER INFORMATION: synthetic oligonucleotide primer

<400> SEQUENCE: 66
agaagaaggc ggccgcttgg ttccttaaat ctaagaggta tga                          43

<210> SEQ ID NO 67
<211> LENGTH: 21
<212> TYPE: DNA
<213> ORGANISM: artificial
<220> FEATURE:
<223> OTHER INFORMATION: synthetic oligonucleotide primer

<400> SEQUENCE: 67
tgctggcaga gaagagcgaa a                                                  21

<210> SEQ ID NO 68
<211> LENGTH: 23
<212> TYPE: DNA
<213> ORGANISM: artificial
<220> FEATURE:
<223> OTHER INFORMATION: synthetic oligonucleotide primer

<400> SEQUENCE: 68
tcttcatccc aatcttcaac ttc                                                23

<210> SEQ ID NO 69
<211> LENGTH: 32
<212> TYPE: DNA
<213> ORGANISM: artificial
<220> FEATURE:
<223> OTHER INFORMATION: synthetic oligonucleotide primer

<400> SEQUENCE: 69
actggatccc tcaccaaacc tccttgtatg at                                      32

<210> SEQ ID NO 70
<211> LENGTH: 59
<212> TYPE: DNA
<213> ORGANISM: artificial
<220> FEATURE:
<223> OTHER INFORMATION: synthetic oligonucleotide primer

<400> SEQUENCE: 70
agagcatgcc atcaccatca ccatcactaa taataaagct gaaataaaag agggtgaga         59

<210> SEQ ID NO 71
<211> LENGTH: 38

```
<212> TYPE: DNA
<213> ORGANISM: artificial
<220> FEATURE:
<223> OTHER INFORMATION: synthetic oligonucleotide primer

<400> SEQUENCE: 71
actggatcca tgacgaaaat agcgaataaa tacgaagt                             38

<210> SEQ ID NO 72
<211> LENGTH: 40
<212> TYPE: DNA
<213> ORGANISM: artificial
<220> FEATURE:
<223> OTHER INFORMATION: synthetic oligonucleotide primer

<400> SEQUENCE: 72
agagcatgct ttcttcgcac ctccgtaata agcgttcaga                           40

<210> SEQ ID NO 73
<211> LENGTH: 21
<212> TYPE: DNA
<213> ORGANISM: artificial
<220> FEATURE:
<223> OTHER INFORMATION: synthetic oligonucleotide primer

<400> SEQUENCE: 73
tggtaatgag agaagcagat g                                              21

<210> SEQ ID NO 74
<211> LENGTH: 22
<212> TYPE: DNA
<213> ORGANISM: artificial
<220> FEATURE:
<223> OTHER INFORMATION: synthetic oligonucleotide primer

<400> SEQUENCE: 74
tgataaaaag cacccagttt gt                                             22

<210> SEQ ID NO 75
<211> LENGTH: 25
<212> TYPE: DNA
<213> ORGANISM: artificial
<220> FEATURE:
<223> OTHER INFORMATION: synthetic oligonucleotide primer

<400> SEQUENCE: 75
tggttgacca ggagaatttt acaca                                          25

<210> SEQ ID NO 76
<211> LENGTH: 23
<212> TYPE: DNA
<213> ORGANISM: artificial
<220> FEATURE:
<223> OTHER INFORMATION: synthetic oligonucleotide primer

<400> SEQUENCE: 76
agcaacaatc ctgcatttgt aag                                            23
```